US008324210B2

(12) United States Patent
Kakkis

(10) Patent No.: US 8,324,210 B2
(45) Date of Patent: Dec. 4, 2012

(54) PTERIN ANALOGS

(75) Inventor: Emil D. Kakkis, Novato, CA (US)

(73) Assignee: BioMarin Pharmaceutical, Inc., Novato, CA (US)

(*) Notice: Subject to any disclaimer, the term of this patent is extended or adjusted under 35 U.S.C. 154(b) by 101 days.

(21) Appl. No.: 12/577,680

(22) Filed: Oct. 12, 2009

(65) Prior Publication Data

US 2010/0093742 A1 Apr. 15, 2010

Related U.S. Application Data

(63) Continuation of application No. 12/260,855, filed on Oct. 29, 2008, now Pat. No. 7,601,717, which is a continuation of application No. PCT/US2008/069319, filed on Jul. 7, 2008.

(60) Provisional application No. 61/018,735, filed on Jan. 3, 2008, provisional application No. 61/019,753, filed on Jan. 8, 2008.

(51) Int. Cl.
A61K 31/5025 (2006.01)
A61P 9/12 (2006.01)

(52) U.S. Cl. ........................................ 514/249; 544/258

(58) Field of Classification Search .................. 514/248
See application file for complete search history.

(56) References Cited

U.S. PATENT DOCUMENTS

| 2,601,215 | A | 6/1952 | Waller et al. |
| 3,505,329 | A | 4/1970 | Weinstock |
| 4,540,783 | A | 9/1985 | Viscontini |
| 4,550,109 | A | 10/1985 | Folkers et al. |
| 4,587,340 | A | 5/1986 | Nichol et al. |
| 4,595,752 | A | 6/1986 | Azuma et al. |
| 4,649,197 | A | 3/1987 | Uchino et al. |
| 4,665,182 | A | 5/1987 | Nichol et al. |
| 4,701,455 | A | 10/1987 | Nichol et al. |
| 4,713,454 | A | 12/1987 | Sakai et al. |
| 4,937,342 | A | 6/1990 | Kurono et al. |
| 4,957,924 | A | 9/1990 | Beauchamp |
| 5,037,981 | A | 8/1991 | Kurono et al. |
| 5,043,339 | A | 8/1991 | Beauchamp |
| 5,198,547 | A | 3/1993 | Bailey et al. |
| 5,350,851 | A | 9/1994 | Bailey et al. |
| 5,401,844 | A | 3/1995 | Ayling et al. |
| 5,698,408 | A | 12/1997 | Rokos |
| 5,753,656 | A | 5/1998 | Sakai et al. |
| 6,162,806 | A | 12/2000 | Arai et al. |
| 6,410,535 | B1 | 6/2002 | Kashiwagi et al. |
| 6,844,343 | B1 | 1/2005 | Pfleiderer et al. |
| 6,858,612 | B1 | 2/2005 | Pfleiderer et al. |
| 2003/0078231 | A1 | 4/2003 | Wilburn |
| 2005/0137141 | A1 | 6/2005 | Hilfinger |
| 2005/0239807 | A1 | 10/2005 | Stamler et al. |
| 2006/0009458 | A1 | 1/2006 | Ishibara et al. |
| 2006/0040946 | A1 | 2/2006 | Oppenheimer et al. |
| 2006/0194800 | A1 | 8/2006 | Wadsworth et al. |
| 2006/0194808 | A1 | 8/2006 | Richardson et al. |
| 2007/0167353 | A1 | 7/2007 | Hilfinger et al. |
| 2007/0244322 | A1 | 10/2007 | Moser et al. |
| 2007/0270581 | A1 | 11/2007 | Jungles et al. |

FOREIGN PATENT DOCUMENTS

| CA | 2420374 | 2/2003 |
| CH | 651755 | 10/1985 |
| EP | 0079574 | 5/1983 |
| EP | 0165595 | 12/1985 |
| EP | 0209689 | 1/1987 |
| EP | 0722731 | 7/1996 |
| JP | 5704990 | 1/1982 |
| JP | 59112987 | 6/1984 |
| JP | 61293983 | 12/1986 |
| JP | 1221380 | 9/1989 |
| WO | WO 2004/058268 | 7/2004 |
| WO | WO 2005/049614 | 6/2005 |
| WO | WO 2006/004719 | 1/2006 |
| WO | WO 2006/063215 | 6/2006 |
| WO | WO 2007/067570 | 6/2007 |
| WO | WO 2008/089008 | 7/2008 |

OTHER PUBLICATIONS

Shen, et al., BioMarin Pharmaceuticals Inc., Feb. 3, 2009, downloaded Jan. 11, 2011, http://www.drugs.com/clinical_trials/results-phase-2-clinical-study-6r-bh4-peripheral-arterial-not-statistically-significant-6687.html.*
Robbins, et al., Exp. Lung. Res. Nov. 15, 2010.*
Silberman, et al., Circulation 121: 519-528, 2010.*
Rao, et al., J Am. Coll. Cardiol., 2008, vol. 52, #2, 166-168.*
Noguchi, et al., Eur J Pharmacol. Apr. 10, 2010;631(1-3):28-35.*
Yim, et al., Current Diab. Rep., vol. 7, #1, 8-13, 2007.*
Tarpey, Arterioscler. Throm. Basc. Biol., 2002:22:1519-1521.*
Dumitrescu, et al., Proc. Natl. Acad. Sci. USA (2007), downloaded Jan. 11, 2011, http://www.ischemic.net/showabstract.php?pmid=17848522.*
Vasquez-Vivar, et al., Arterioscler. Thromb. Vasc. Biol., Oct. 2002, 1655-1661.*
Linscheid, et al., Biochem. Pharmacol., 65 (2003) 593-598.*
DeBraun, speaking at the 50th Annual Meeting of the Am. Soc. of Hematology, Dec. 7, 2008, http://www.hemonctoday.com/article.aspx?rid=33385, downloaded Jan. 11, 2011.*
Ataga, Am. Soc. Hematol., 2009, 54-61.*
Choi, et al., Neurochem Int. Mar. 2006;48(4):255-62.*
Wikipedia, Tetrahydrobiopterin, http://en.wikipedia.org/wiki/Tetrahydrobiopterin, downloaded Jan. 12, 2011.*
Richardson, et al., Neurochem Res. Jan. 2007;32(1):107-13.*
Aizpurua et al., "Reaction of hindered trialkylsilyl esters and trialkylsilyl ethers with triphenylphosphine dibromide: preparation of carboxylic acid bromides and alkyl bromides under mild neutral conditions," *J. Org. Chem.*, 51(25), 4941-4943 (1986).
Anand et al., "Current prodrug strategies via membrane transporters/receptors," *Expert Opin. Biol. Ther.*, 2(6), 607-620 (2002).
Artusson et al., "Intestinal drug absorption and metabolism in cell cultures: Caco-2 and beyond," *Pharm. Res.*, 14(12), 1655-1657 (1997).
Ashton et al., "Amino acid derivatives of β-cyclodextrin," *J. Org. Chem.*, 61(3), 903-908 (1996).
Aungst et al., *Prodrug to reduce presystemic metabolism*, 339-355 (2007).
Bell et al., "The reduction of organic halogen compounds by sodium borohydride," *J. Org. Chem.*, 34, 3923-3926 (1969).
Bjelakovic et al., "Biochemical functions and clinical importance of unconjugated pteridines," *Medicine and Biology*, 11(2), 49-54 (2004).

(Continued)

Primary Examiner — Susanna Moore
Assistant Examiner — Cecilia M Jaisle
(74) Attorney, Agent, or Firm — Jones Day

(57) ABSTRACT

Disclosed herein are analogs of tetrahydrobiopterin, compositions containing the same, and methods of treating an individual suffering from a condition responsive to tetrahydrobiopterin by administration of the analog. These analogs are contemplated for use wherever tetrahydrobiopterin is currently used to treat conditions responsive to tetrahydrobiopterin therapies.

7 Claims, 18 Drawing Sheets

OTHER PUBLICATIONS

Bjorge et al., "Evidence for glucuronide conjugation of p-nitrophenol in the caco-2 cell model," *Pharm. Res.*, 8, 1441-1443 (1991).

Blau et al., "Disorders of tetrahydrobiopterin and related biogenic amines" in *The metabolic and molecular bases of inherited disease*, 8th Ed., Scriver et al. Eds. New York, McGraw-Hill, 1725-1776 (2001).

Bradshaw et al., "Synthesis of the organic ligand of the molybdenum cofactor, in protected form," *J. Chem. Soc. Perkin Trans. 1*, 3239-3244 (2001).

Bredereck et al., "Darstellung und eigenschaften der amidacetale und aminalester," *Chem. Ber.*, 101, 41-50 (1968).

Chaudhary et al., "4-Dimethylaminopyridine: an efficient and selective catalyst for the silyation of alcohols," *Tetrahedron Lett.*, 2, 99-102 (1979).

Cho et al., "Tepidopterin, 1-O-(L-threo-biopterin-2'-yl)-β-N-acetylglucosamine from *Chlorobium tepidum*," *Biochim. Biophys. Acta*, 1379, 53-60 (1998).

Corey et al., "Protection of Hydroxyl groups as tert-butyldimethylsilyl derivatives," *J. Am. Chem. Soc.*, 94(17), 6190-9191 (1972).

De Clercq et al., "Antiviral prodrugs—the development of successful prodrug strategies for antiviral chemotherapy," *Brit. J. Pharmacol.*, 147, 1-11 (2006).

Friedrichsen et al., "Synthesis of analogs of L-valacyclovir and determination of their substrate activity for the oligopeptide transporter in caco-2 cells," *Eur. J. Pharma. Sci.*, 16, 1-13 (2002).

Fukishima et al., "Analysis of reduced forms of biopterin in biological tissues and fluids," *Anal. Biochem.* 102, 176-188 (1980).

Gaucher et al., "Prodrugs of HIV protease inhibitors—saquinavir, indinavir and nelfinavir—derived from diglycerides or amino acids: synthesis, stability and anti-HIV activity," *Org. Biomol. Chem.*, 2, 345-357 (2004).

Gomes et al., "Cyclization-activated prodrugs," *Molecules*, 12, 2484-2506 (2007).

Green et al., *Protective groups in organic synthesis*, Wiley & Sons, 3rd Ed., 201-245 (1999).

Guzik et al., "Mechanisms of increased vascular superoxide production in human diabetes mellitus: Role of NAD(P)H oxidase and endothelial nitric oxide synthase," *Circulation*, 105(14), 1656-1662 (2002).

Hanaya et al., "First synthesis of tepidopterin [2'-O-(2-acetarnido-deoxy-β-D-glucopyranosyl)-L-threo-biopterin]," *Carbohydrate Res.*, 342, 2159-2162 (2007).

Hanaya et al., "Selective N(3)-and-$O^4$-alkylation of L-biopterin: a convenient synthesis of 3-and $O^4$-methyl-L-biopterin and the versatile $N^2$-(N,N-dimethylaminomethylene)-N(3)-p-nitrophenethyl-protected L-biopterin," *Pteridines*, 6(1), 1-7 (1995).

Hanessian et al., "Reactions of carbohydrates with (halomethylene)dimethyliminium halides and related reagents; synthesis of some chlorodeoxy sugars," *J. Org. Chem.*, 34(7), 2163-2170 (1969).

Hardon et al., "Prodrugs of the selective antiherpesvirus agent 9-[4-hydroxy-3-(hydroxymethyl)but-l-yl]guanine (BRL 39123) with improved gastrointestinal absorption properties," *J. Med. Chem.*, 32, 1738-1743 (1989).

Hart et al., "Asymmetric synthesis of the carbapenam core from serine," *J. Org. Chem.*, 68(1), 187-190 (2003).

He et al., "Absorption of ester prodrugs in caco-2 and rat intestine models," *Antimicrob. Agents Chemother.*, 48, 2604-2609 (2004).

Heitzer et al., "Tetrahydrobiopterin improves endothelium-dependent vasodilation by increasing nitric oxide activity in patients with Type II diabetes mellitus," *Diabetologia*, 43(11), 1435-1438 (2000).

Hutchins et al., "Sodium borohydride in dimethyl sulfoxide or sulfolane. Convenient systems for selective reductions of primary, secondary, and certain tertiary halides and tosylates," *Tetrahedron Lett.*, 40, 3495-3498 (1969).

Imai et al., "Identification of esterases expressed in taco-2 cells and effects of their hydrolyzing activity in predicting human intestinal absorption," *Drug Metabolism and Disposition*, 33, 1185-1190 (2005).

Inui et al., "Transepithelial transport of oral cephalosporins by monolayers of intestinal epithelial cell line Caco-2: specific transport systems in apical and basolateral membranes," *J. Pharmacol. Exp. Ther.*, 261, 195-201 (1992).

Kaiser et al., "80. Synthesis of biopterin from neopterin? The formation of pyrrolo[1,2-f]pteridins upon side-chain activation of neopterin," *Helv. Chim. Acta*, 70, 766-770 (1987).

Kang et al., "Synthesis of 2-ethylthio-6-(3-hydroxy-1,2-O-isopropylidenepropypl)pteridin-4(3H)-one," *Heterocycles*, 53(7), 1551-1557 (2000).

Kikuchi et al., "Synthesis of (-)-biopterin using (S)-ethyl lactate as a starting material," *Agric. Biol. Chem.*, 53(8), 2095-2100 (1989).

Kim et al., "A novel nucleoside prodrug-activating enzyme: Substrate specificity of biphenyl hydrolase-like protein," *Mol. Pharmaceut.*, 1(2), 117-127 (2004).

Kim et al., "Biophenyl hydrolase-like protein as valacyclovir hydrolase," *J. Biol. Chem.*, 278, 25348-25356 (2003).

Kim et al., "Direct conversion of silyl ethers into alkyl bromides with boron tribromide," *J. Org. Chem.*, 53, 3111-3113 (1988).

Kim et al., "Structure and specificity of a human valacyclovir activating enzyme: A homology model of BPHL," *Mol. Pharmaceut.*, 1(6), 434-446 (2004).

Larock, *Comprehensive Organic Transformations*, Wiley VCH, 2nd Ed., 681-708 (1999).

Li et al., "Prodrugs of nucleoside analogues for improved oral absorption and tissue targeting," *J. Pharm. Sci.*, 97(3), 1109-1134 (2008).

Lin et al., "Structure of solfapterin (erythro-neopterin-3'-D-2-deoxy-2-aminoglucopyranoside) isolated from the thermophilic archaebacterium *Sulfolobus solfataricus*," *J. Bacteriol.*, 1396-1398 (1988).

Lorenzi et al., "Amino acid ester prodrugs of 2-bromo-5,6-dichloro-1-(β—D-ribofuranosyl)benzimidazole enhance metabolic stability in vitro and in vivo," *J. Pharmcol. Exp. Therapeut.*, 314, 883-890 (2005).

Lu et al., "Effect of subculturing on the epithelial properties of caco-2 cells as a transport model," *Pharm. Res.*, 1 1, S-258 (1994).

Mack et al., "Sickle cell disease and nitric oxide: A paradigm shift," *Int. J. Biochem. Cell Biol.*, 38, 1237-1243 (2006).

Matsuura et al., "Studies on biologically active pteridines—VIII. Preparation of a specific antiserum against tetrahydrobiopterin, a cofactor for monoamine-synthesizing monooxygenases," *Biogenic Amines*, 1, 259-266 (1984).

Mattes et al., "Reactivity of t-butyldimethylsilyl ethers: a facile conversion into bromides," *Tetrahedron Lett.*, 28(15), 1697-1698 (1987).

Morris et al., "Hydroxyurea and arginine therapy: Impact on nitric oxide production in sickle cell disease," *J. Pediatric Hematology*, 25, 629-634 (2003).

Nystrom et al., "Tctrahydrobiopterin increases insulin sensitivity in patients with type 2 diabetes and coronary heart disease," *Am. J. Physiol. Endocrinol. Metab.*, 287(5), E919-E925 (2004).

Office Action mailed Jun. 25, 2009, U.S. Appl. No. 10/579,106.

Office Action mailed Mar. 27, 2009, U.S. Appl. No. 12/260,855.

Notice of Allowance mailed Jul. 30, 2009, U.S. Appl. No. 12/260,855.

Supplemental Notice of Allowance mailed Aug. 31, 2009, U.S. Appl. No. 12/260,855.

Patterson et al., "The synthesis of a pteridine required for the growth of crithidia fasciculate," *J Am. Chem. Soc.*, 78(58), 5868-5871 (1956).

Pellicciari et al., "Stereospecific synthesis of the enantiomers of nicotinylalaline, a neuroprotecting agent," *Tetrahedron. Lett.*, 33, 3003-3004 (1992).

Purifoy et al., "Review of research leading to new anti-herpesvirus agents in clinical development: Valaciclovir hydrochloride (256U, the L-valyl ester of acyclovir) and 882C, a specific agent for Vricella Zoster virus," *J. Med. Virol. Supp.*, 1, 139-145 (1993).

Reiter et al., "An emerging role for nitric oxide in sickle cell disease vascular homeostasis and therapy," *Curr. Opin. Hematology*, 10, 99-107 (2003).

Ross et al., "Anodic oxidations. V. The Kolbe oxidation of phenylacetic acid and 1-methylcyclohexaneacetic acid at platinum and at carbon," *J. Org. Chem.*, 24, 2923-2927 (1969).

Russell et al., "Model studies related to the cofactor of the oxomolybdoenzymes; Part 6: An improved synthesis of 6-substituted pterins from 2,4,5-triamino-6-hydroxy-pyrimidine and D-glucose," *Synlett*, 9, 711-712 (1992).

Russell et al., "Model studies related to the cofactor of the oxomolybdoenzymes; Part 5: Synthesis of 6-alkenyl- and 6-alkynylpterins," *Tetrahedron Lett.*, 33(23), 3371-3374 (1992).

Schircks et al., "Eine neue, regiospezitische synthese von L-biopterin," *Helv. Chim. Acta*, 60(24), 211-214 (1977).

Smith et al., *March's advanced organic chemistry, reactions mechanisms and structure*, Wiley & Sons, Inc., 5th Ed., 524-526 (2001).

Song et al., "Amino acid ester prodrugs of the anticancer agent gemcitabine: Synthesis, bioconversion, metabolic bioevasion, and hPEPT1-mediated transport," *Mol. Pharmaceut.*, 2(2), 157-167 (2005).

Song et al., "Amino acid ester prodrugs of the antiviral agent 2-bromo-5,6-dichloro-1-(β-D-ribofuranosyl)benzimidazole as potential substrates of hPEPT1 transporter," *J. Med. Chem.*, 48(4), 1274-1277 (2005).

Soyka et al., "Synthese und eigenschaften von 5,6-dihydro-6-(1,2,3-trihydroxypropyl)pteridinen: kovalente intromolekulare addukte," *Helv. Chim. Acta*, 73, 808-826 (1990).

Space et al., "Nitric oxide attenuates normal and sickle red blood cell adherence to pulmonary endothelium," *Am. J. Hematology*, 63, 200-204 (2000).

Stewart et al., "Comparison of intestinal permeabilities determined in multiple in vitro and in situ models: Relationship to absorption in humans," *Pharm. Res.*, 12, 693-699 (1995).

Sugimoto et al., "The convenient syntheses of biopterin and its three optical isomers," *Bull. Chem. Soc. Jpn.*, 48(12), 3767-3768 (1975).

Sugimoto et al., "Chemistry and biological function of biopterin cofactor and related compounds," *J Synth. Org. Chem. Jpn.*, 46(6), 564-573 (1988).

Taylor et al., "An unequivocal total synthesis of L-erythro-biopterin," *J. Am. Chem. Soc.*, 96(21), 6781-6782 (1974).

Thony et al., "Tetrahydrobiopterin biosynthesis, regeneration and functions," *Biochem. J.*, 347(1), 1-16 (2000).

Viscontini et al., "Eine neue synthese von D, L-biopterin," *Helv. Chim. Acta*, 55(60), 574-579 (1972).

Viscontini et al., "Synthese des naturlichen D-neopterins und L-monapterins," *Helv. Chim. Acta*, 53, 1202-1207 (1970).

Werner et al., "Contrasting effects of N(5)-substituted tetrahydrobiopterin dihydropteridine reductase and nitric oxide synthase," *Biochem. J.*, 348, 579-583 (2000).

Wood et al., "Critical role of endothelial cell-derived nitric oxide synthase in sickle cell disease-induced microvascular dysfunction," *Free Radical Biol. Med.*, 40, 1443-1453 (2006).

Wood et al., "Endothelial cell NADPH oxidase mediates the cerebral microvascular dysfunction in sickle cell transgenic mice," *FASEB J.*, 19, 989-991 (2005).

Zinner et al., "Die partielle veresterung von D-arabinose-mercaptalen mit sulfonsaurechloriden und eine einfache synthese der 5-desoxy-D-arabinose," *Chem. Ber.*, 92, 1618-1623 (1959).

Zinner et al., "Synthese und derivate der 2,5-didesoxy-D-ribose," *Chem. Ber.*, 92, 2893-2896 (1959).

Danfors et al., "Tetrahydrobiopterin in the Treatment of Children with Autistic Disorder," *J. Clin. Psychopharmacology*, 2005, 25, 485-489.

Frye et al., "Tetrahydrobiopterin as a Novel Therapeutic Intervention for Autism," *Neurotherapeutics*, 2010, 7, 241-249.

Nakane et al., "Clinical Effect of R-THBP on Infantile Autism," Naruse and Omitz eds.; Neurobiology of infantile autism; Proceedings of the International Symposium on Neurobiology of Infantile Autism; Nov. 10-11, 1990; Tokyo, Japan; Amsterdam: Elsevier Science Ltd; 1992: 337-350.

Fernell et al., "Possible effects of tetrahydrobiopterin treatment in six children with autism—clinical and positron emission tomography data: a pilot study:" *Dev. Med. Child Neurology*, 39, 313-318 (1997).

\* cited by examiner

| Assay | LC/MS/MS Determination of BH4 in Human Plasma | HPLC Determination of Biopterin in Human Plasma |
|---|---|---|
| Analyte Name | Terahydrobiopterin (BH4) | Biopterin |
| Analyte Name (Oxidation Product) | L-Biopterin | Biopterin |
| Internal Standard | Irbesartan | Biopterin |
| Analytical Method Type | LC/MS/MS | HPLC (Ex 365 nm/Em 473 nm) |
| Extraction Method | Protein Precipitation | Protein Precipitation |
| QC Concentrations | 5, 15, 150, and 800 ng/mL BH4 | 1, 10, and 40 ng/mL Biopterin |
| Standard Curve Concentrations | 5, 15, 50,100, 300, 500, and 1000 ng/mL | 0.5, 1, 2.5, 5, 10, 25, and 50 ng/mL |
| Lower Limit of Quantitation | 5 ng/mL | (5 ng/mL Biopterin) |
| Upper Limit of Quantitation | 1000 ng/mL | (50 ng/mL Biopterin) |
| Average Recovery of Drug | 65.3% | ?? |
| Average Recovery of Internal Standard | 94% | 74-94% |
| QC Intraday Precision Range | 4.7 to 14.5 %CV | 0.8 to 13 |
| QC Intraday Accuracy Range | -7.1 to 7.4 %Diff | -2.8 to 6.1 |
| QC Interday Precision Range | 7.4 to 16.4 %CV | 0.6 to 4.9 |
| QC Interday Accuracy Range | -8.3 to 3.7 %Diff | ?? |
| Stock Solution Solvent | MeOH:DMSO/50:50 (v:v) | Ammonium Phosphate Buffer |
| Benchtop Stability in Human Plasma | 4.5 hrs at RT | ?? |
| Freeze/Thaw Stability in Human Plasma | 4 Cycles at -70 °C | 2 Cycles at -20 °C |
| Conversion Ratio from BH4 to L-Biopterin | 47% (at 12 Weeks) | ?? |
| Long-term Stability in K2 EDTA Plasma | 38 Days at -70 °C | ?? (7 Days at -20 °C) |
| Dilution Integrity | 1500 ng/mL Diluted 10-Times | ?? |
| Selectivity | BH4 | Total Biopterin |

FIG. 2

***P<0.001, 2-way ANOVA without interaction
Followed by Bonferroni's post-test (###P<0.001)

PTERIN ANALOGS

CROSS REFERENCE TO RELATED APPLICATIONS

This application is a continuation of U.S. application Ser. No. 12/260,855, filed Oct. 29, 2008, which is a continuation of International Patent Application No. PCT/US08/69319, filed Jul. 7, 2008, which claims the benefit of U.S. Provisional Application Nos. 61/018,735, filed Jan. 3, 2008, and 61/019, 753, filed Jan. 8, 2008, the disclosure of each of which is incorporated herein by reference in its entirety.

BACKGROUND OF THE INVENTION

1. Field of the Disclosure

The disclosure generally relates to analogs of tetrahydrobiopterin, compositions containing the same, and methods of treating an individual suffering from a condition responsive to tetrahydrobiopterin by administration of the analog.

2. Brief Description of Related Technology

Tetrahydrobiopterin (also referred to herein as "BH4") is a naturally-occurring chemical compound and is a biologically active amine of the pterin family. One stereoisomer, sapropterin, is shown in Formula II, below:

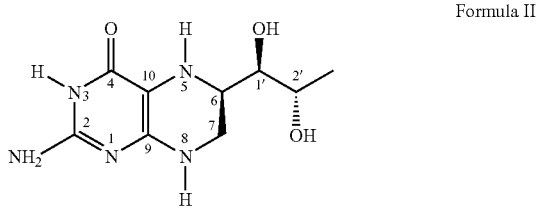

Formula II

Although naturally-occurring, tetrahydrobiopterin also may be synthesized by a variety of methods, some of which are disclosed in, for example, U.S. Pat. Nos. 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408; and, 5,698,408, and Canadian patent application No. 2,420,374.

Pterins are bicyclic compounds that include a pyrazine ring and a pyrimidine ring having a carbonyl oxygen and an amino group. Pterins function as cofactors in enzymatic catalysis. Tetrahydrobiopterin functions as a cofactor for a number of different enzymes, including phenylalanine hydroxylase (PAH), tyrosine 3-hydroxylase, tryptophan 5-hydroxylase, and all three forms of nitric oxide synthase (NOS). Tetrahydrobiopterin also is a growth factor for *Crithidia fasciculata*, has proliferative activity in haemopoietic cells, and acts as a self-protecting factor for nitric oxide toxicity. These and other cofactor and cellular functions of tetrahydrobiopterin as well as disorders relating to tetrahydrobiopterin deficiency are disclosed in Thony et al. (2000) *Biochem. J.* 347:1-16. Disorders relating to tetrahydrobiopterin deficiency also are generally described in Blau et al., *Disorders of Tetrahydrobiopterin and Related Biogenic Amines*, in *The Metabolic and Molecular Bases of Inherited Disease*, 1275-776 (8th ed., McGraw-Hill Publishing Co., New York, N.Y., 2001).

Tetrahydrobiopterin is a hydrophilic compound that has difficulty crossing membranes as well as traversing the blood-brain barrier. The blood-brain barrier generally is a membrane that controls the passage of substances from the blood into the central nervous system (CNS). It functions as a physical barrier between local blood vessels and most parts of the CNS, preventing certain (and many) compounds from reaching the CNS. The walls defining capillaries in the body are made up of endothelial cells separated by small gaps. These gaps permit soluble chemicals within tissues to pass into the blood stream, so that the chemicals can be carried throughout the body, and subsequently pass out of the blood into different tissues. In the brain, these endothelial cells are packed more tightly and, therefore, the gaps are even smaller. These smaller gaps block the passage of all molecules except those that cross cell membranes due to lipid solubility (e.g., oxygen, carbon dioxide, ethanol) and those that pass by specific transport systems (e.g., sugars, select amino acids). Many drugs do not cross the blood-brain barrier in amounts effective to provide therapy. In addition to providing a physical barrier to the CNS, endothelial cells in the brain also may metabolize certain molecules (drugs) so that they never reach the CNS.

The present invention is directed to more effective ways of delivering tetrahydrobiopterin to the body as well as to the CNS to provide effective therapy for disorders and conditions responsive to tetrahydrobiopterin.

SUMMARY OF THE INVENTION

Disclosed herein are analogs of tetrahydrobiopterin, compositions containing the same, and methods of treating an individual suffering from a condition responsive to tetrahydrobiopterin therapy by administration of one or more of the analogs.

The compounds disclosed herein are analogs, and can be prodrugs, of tetrahydrobiopterin or a tetrahydrobiopterin derivative which can generate tetrahydrobiopterin or a derivative thereof, respectively, in vivo. Tetrahydrobiopterin is a naturally-occurring chemical that also be obtained by chemical synthesis known by those skilled in the art.

It has been discovered that orally administered tetrahydrobiopterin has a low bioavailability. This low bioavailability is generally believed to be attributable to at least one of poor absorption from the gastrointestinal (GI) tract, oxidation in the GI tract and/or the bloodstream, degradation or metabolism prior to absorption, and degradation or metabolism after absorption. Furthermore, it is believed that tetrahydrobiopterin exhibits poor (lipid) solubility, potential chemical instability in the stomach and bloodstream, and inability to permeate the walls of the GI tract.

One aspect of the disclosure is directed to improving bioavailability of tetrahydrobiopterin in an individual by administering a therapeutically effective amount of an analog and/or a prodrug of tetrahydrobiopterin to an individual in need thereof, wherein, if the analog is a prodrug of BH4, endogenous enzymes can release the active tetrahydrobiopterin or tetrahydrobiopterin derivative, respectively, in vivo. The prodrug approach is suitable in the case of tetrahydrobiopterin because this compound interacts with at least six different enzymes (e.g., phenylalanine hydroxylase, tyrosine hydroxylase, tryptophan hydroxylase, endothelial nitric oxide synthase, neuronal nitric oxide synthase, and inducible nitric oxide synthase). In addition, tetrahydrobiopterin undergoes recycling after participating in a hydroxylation reaction that requires two other enzymes. Therefore, an analog of tetrahydrobiopterin that does not both properly interact with these six enzymes and be recycled by two additional enzymes, may not function well as a cofactor and could not be used stoichiometrically, especially if not recycled properly. For these reasons, an analog that generates the natural tetrahydrobiopterin compound is far superior to a compound that has better bioavailability but cannot properly interact with all the cellular targets of tetrahydrobiopterin.

Accordingly, one aspect of the invention is directed to analogs of tetrahydrobiopterin. An analog of tetrahydrobiopterin is a compound of Formula I (shown below as one specific stereoisomer) or a pharmaceutically acceptable salt thereof:

Formula I

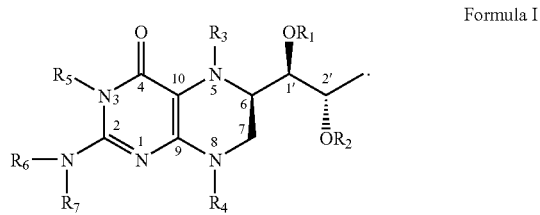

Also contemplated are the other seven possible stereoisomers of BH4. An analog of BH4 can be, but is not limited to, a prodrug which can liberate BH4 under biological conditions.

According to an embodiment of the compound of Formula I, $R_3$, $R_4$, $R_5$, $R_6$, and $R_7$ are all hydrogen, and $R_1$ and $R_2$ together are —$C(R^c)R^d$— and form a five-membered ring, or $R_1$ and $R_2$ are independently hydrogen, $C_{3-8}$cycloalkyl, $C_{1-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkylene$C_{3-8}$cycloalkyl, $C_{2-40}$alkylene$C_{3-8}$cycloalkenyl, $C_{2-40}$alkylene$C_{3-8}$heterocycloalkyl, $C_{2-40}$alkylene$C_{3-8}$heterocycloalkenyl, $C_{2-40}$alkylenearyl, $C_{2-40}$alkyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkylene$C_{3-8}$cycloalkyl, C(O)$C_{2-40}$alkylene$C_{3-8}$cycloalkenyl, C(O)$C_{2-40}$alkylene$C_{3-8}$heterocycloalkyl, C(O)$C_{2-40}$alkylene$C_{3-8}$heterocycloalkenyl, C(O)$C_{2-40}$alkylenearyl, C(O)$C_{2-40}$alkyleneheteroaryl, C(O)NR$^a$R$^b$, C(O)OR$^a$, C(O)SR$^a$, or an amino acid derivative, with the proviso that $R_1$ and $R_2$ are not both hydrogen, C(O)H, glucosyl, aminoglucosyl, or the same C(O)$C_{1-10}$alkyl. In one embodiment, $R_1$ and $R_2$ are independently selected from amino acid derivatives and hydrogen, and the non-amino acid derivatized R groups are hydrogen. In an embodiment, $R_1$ is selected from amino acid derivatives and $R_2$ is hydrogen. In another embodiment, $R_2$ is selected from amino acid derivatives and $R_1$ is hydrogen. The amino acid derivative (e.g., that at $R_1$ or $R_2$) can comprise, but is not limited to, a valyl amino acid moiety.

According to another embodiment of the compound of Formula I, $R_1$, $R_2$, $R_5$, $R_6$, and $R_7$ are all hydrogen; and, $R_3$ and $R_4$ are independently hydrogen, $C_{3-8}$cycloalkyl, $C_{2-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkylene$C_{3-8}$cycloalkyl, $C_{2-40}$alkylene$C_{3-8}$cycloalkenyl, $C_{2-40}$alkylene$C_{3-8}$heterocycloalkyl, $C_{2-40}$alkylene$C_{3-8}$heterocycloalkenyl, $C_{2-40}$alkylenearyl, $C_{2-40}$alkyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkylene$C_{3-8}$cycloalkyl, C(O)$C_{2-40}$alkylene$C_{3-8}$cycloalkenyl, C(O)$C_{2-40}$alkylene$C_{3-8}$heterocycloalkyl, C(O)$C_{2-40}$alkylene$C_{3-8}$heterocycloalkenyl, C(O)$C_{2-40}$alkylenearyl, C(O)$C_{2-40}$alkyleneheteroaryl, C(O)NR$^a$R$^b$, C(O)OR$^a$, or C(O)SR$^a$, with the proviso that when $R_3$, is hydrogen, then $R_4$ is not hydrogen or ribose, and when $R_4$ is hydrogen, then $R_3$ is not hydrogen, C(O)H, acetate, hydroxymethyl, or aminoalkyl.

According to still another embodiment of the compound of Formula I, $R_1$, $R_2$, $R_3$, $R_4$, and $R_5$ are all hydrogen; and, $R_6$, and $R_7$, are independently hydrogen, $C_{3-8}$cycloalkyl, $C_{1-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkylene$C_{3-8}$cycloalkyl, $C_{2-40}$alkylene$C_{3-8}$cycloalkenyl, $C_{2-40}$alkylene$C_{3-8}$heterocycloalkyl, $C_{2-40}$alkylene$C_{3-8}$heterocycloalkenyl, $C_{2-40}$alkylenearyl, $C_{2-40}$alkyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkylene$C_{3-8}$cycloalkyl, C(O)$C_{2-40}$alkylene$C_{3-8}$cycloalkenyl, C(O)$C_{2-40}$alkylene$C_{3-8}$heterocycloalkyl, C(O)$C_{2-40}$alkylene$C_{3-8}$heterocycloalkenyl, C(O)$C_{2-40}$alkylenearyl, C(O)$C_{2-40}$alkyleneheteroaryl, C(O)NR$^a$R$^b$, C(O)OR$^a$, or C(O)SR$^a$, with the proviso that when $R_6$ is hydrogen, then $R_7$ is not hydrogen, methyl, CH$_2$(CH$_2$)$_4$ CO$_2$H, or CH$_2$CH$_2$-aryl, and that when $R_7$ is hydrogen, then $R_6$ is not hydrogen.

According to yet another embodiment of the compound of Formula I, $R_1$, $R_2$, $R_3$, $R_4$, $R_6$, and $R_7$ are all hydrogen; and, $R_5$, is $C_{3-8}$cycloalkyl, $C_{1-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkylene$C_{3-8}$cycloalkyl, $C_{2-40}$alkylene$C_{3-8}$cycloalkenyl, $C_{2-40}$alkylene$C_{3-8}$heterocycloalkyl, $C_{2-40}$alkylene$C_{3-8}$heterocycloalkenyl, $C_{2-40}$alkylenearyl, $C_{2-40}$alkyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkylene$C_{3-8}$cycloalkyl, C(O)$C_{2-40}$alkylene$C_{3-8}$cycloalkenyl, C(O)$C_{2-40}$alkylene$C_{3-8}$ heterocycloalkyl, C(O)$C_{2-40}$alkylene$C_{3-8}$ heterocycloalkenyl, C(O)$C_{2-40}$alkylenearyl, C(O)$C_{2-40}$alkyleneheteroaryl, C(O)NR$^a$R$^b$, C(O)OR$^a$, or C(O)SR$^a$.

In another contemplated type of embodiment of the compound of formula I, $R_3$, $R_4$, $R_5$, $R_6$, and $R_7$ are all hydrogen, and $R_1$ and $R_2$ are each independently selected from hydrogen and an amino acid derivative, wherein $R_1$ and $R_2$ cannot both be hydrogen. In one such type of embodiment, the amino acid derivative is part of the compound of formula I via an ester bond. In specific embodiments, the amino acid derivative is a single amino acid, while in other embodiments, the amino acid derivative is two, three, four, or more amino acids covalently linked together via amide bonds or ester bonds or both. For example, in specific contemplated embodiments, $R_1$ is hydrogen and $R_2$ comprises alanine, valine, or a dipeptide comprising glutamic acid and alanine. In other specific embodiments, $R_1$ and $R_2$ both comprise valine.

In another contemplated type of embodiment of the compound of formula I, $R_1$, $R_2$, $R_4$, $R_5$, $R_6$, and $R_7$ are all hydrogen, and $R_3$ is an amino acid derivative. In one such type of embodiment, the amino acid derivative is a single amino acid, while in other embodiments, the amino acid derivative is two, three, four, or more amino acids covalently linked together via amide bonds or ester bonds or both.

In each of the aforementioned embodiments of the compound of Formula I, $R^a$ and $R^b$ are independently hydrogen, $C_{3-8}$cycloalkyl, $C_{1-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenylene$C_{3-8}$cycloalkyl, $C_{2-40}$alkenylene$C_{3-8}$cycloalkenyl, $C_{2-40}$alkenylene$C_{3-8}$heterocycloalkyl, $C_{2-40}$alkenylene$C_{3-8}$heterocycloalkenyl, $C_{2-40}$alkenylenearyl, $C_{2-40}$alkenyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkenylene$C_{3-8}$cycloalkyl, C(O)$C_{2-40}$alkenylene$C_{3-8}$cycloalkenyl, C(O)$C_{2-40}$alkenylene$C_{3-8}$heterocycloalkyl, C(O)$C_{2-40}$alkenylene$C_{3-8}$heterocycloalkenyl, polyethylene glycol, C(O)$C_{2-40}$alkenylenearyl, or C(O)$C_{2-40}$alkenyleneheteroaryl.

Also, in each of the aforementioned embodiments of the compound of Formula I, $R^c$ and $R^d$ together are oxo, or $R^c$ and $R^d$ are independently hydrogen, $C_{3-8}$cycloalkyl, $C_{1-40}$alkyl, $C_{1-40}$substituted alkyl, $C_{3-8}$heterocycloalkyl, $C_{1-40}$alkylene$C_{3-8}$cycloalkyl, $C_{1-40}$alkylene$C_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenylene$C_{3-8}$cycloalkyl, $C_{2-40}$alkenylene$C_{3-8}$cycloalkenyl, $C_{2-40}$alkenylene$C_{3-8}$heterocycloalkyl, $C_{2-40}$alkenylene$C_{3-8}$heterocycloalkenyl, $C_{2-40}$alkenylenearyl, $C_{2-40}$alkenyleneheteroaryl, C(O)H, C(O)$C_{3-8}$cycloalkyl, C(O)$C_{1-40}$alkyl, C(O)$C_{1-40}$substituted alkyl, C(O)$C_{3-8}$heterocycloalkyl, C(O)$C_{1-40}$alkylene$C_{3-8}$cycloalkyl, C(O)$C_{1-40}$alkylene$C_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$alkenyl, C(O)$C_{2-40}$substituted alkenyl, C(O)$C_{3-8}$heterocycloalkenyl, C(O)$C_{2-40}$alkenylene$C_{3-8}$cycloalkyl, C(O)$C_{2-40}$alkenylene$C_{3-8}$cycloalkenyl, C(O)$C_{2-40}$alkenylene$C_{3-8}$heterocycloalkyl, C(O)$C_{2-40}$alkenylene$C_{3-8}$heterocycloalkenyl, C(O)$C_{2-40}$alkenylenearyl, or C(O)$C_{2-40}$alkenyleneheteroaryl.

The present invention also is directed to providing a composition for treating an individual suffering from a condition responsive to tetrahydrobiopterin therapy. The compositions generally can include any one of the aforementioned embodiments of the compound of Formula I and, optionally, a pharmaceutically acceptable excipient such as a diluent or carrier therefor.

Yet another aspect of the invention is to provide a method of treating an individual suffering from a BH4-responsive condition by administration of any one of the aforementioned compositions. The method includes administering to the individual a therapeutically effective amount of a compound of Formula I. BH4-responsive conditions generally include those sensitive to BH4 or a derivative thereof. BH4-responsive conditions include diabetes-related vascular complications including but not limited to disorders of general vascular functions (abnormal vascular compliance, endothelial dysfunction and hypertension); recalcitrant hypertension; insulin sensitivity/glucose control disorders; abnormal peripheral perfusion (intermittent claudication, reduced peripheral perfusion, decreased skin blood flow and defective wound healing); cardiac disease (congestive heart failure, pulmonary hypertension with or without congestive heart failure, exercise-associated angina, coronary artery disease, related atherosclerosis); ophthalmic disease (optic atrophy, diabetic retinal disease); and renal disease (microalbuminuria in diabetic renal disease, renal failure, decreased glomerular filtration rate).

BH4-response conditions also include vascular disease unrelated to diabetes selected from the group consisting of pulmonary vascular disease, hemolytic anemias, stroke and related ischemic vascular disease (such as stroke, cardiac or coronary disease, arteriosclerosis, or peripheral vascular disease), thrombosis, transplant-related endothelial dysfunction, and cardiac or coronary disease. In one embodiment, pulmonary vascular disease includes but is not limited to pulmonary tension in sickle cell anemia and other hemoglobinopathies, idiopathic pulmonary hypertension, persistent pulmonary hypertension of the newborn (PPHN). In a further embodiment, hemolytic anemias include hereditary hemolytic anemias and acquired hemolytic anemia. Hereditary hemolytic anemias include but are not limited to sickle-cell anemia, thalassemia, hemolytic anemia due to G6PD deficiency or associated with hemolysis, pyruvate kinase deficiency, hereditary elliptocytosis, hereditary spherocytosis, hereditary stomatocytosis, hereditary ovalocytosis, paroxysmal nocturnal hemoglobinuria, and hemoglobin SC disease. Acquired hemolytic anemias include but are not limited to microangiopathic hemolytic anemia, idiopathic autoimmune hemolytic anemia, non-immune hemolytic anemia caused by chemical or physical agents or devices (left ventricular assist devices), mechanical heart valves and bypass devices), and secondary immune hemolytic anemia.

In another embodiment, stroke and related ischemic vascular disease includes but is not limited to vasospasm, such as post-stroke cerebrovascular spasm. Thrombosis includes but is not limited to thrombogenesis, thrombosis, clotting, and coagulation. In a further embodiment, transplant-related endothelial dysfunction includes but is not limited to vascular dysfunction after solid organ transplantation and cyclosporine A induced endothelial dysfunction. In yet another embodiment, cardiac or coronary disease includes but is not limited to congestive heart failure, vascular dysfunction and angina associated with hypercholesterolemia, and vascular dysfunction and angina associated with tobacco smoking.

For the compositions and methods described herein, preferred features, such as components, compositional ranges thereof, conditions, and steps, can be selected from the various examples provided herein.

Additional features of the invention may become apparent to those having ordinary skill in the art from a review of the following detailed description, taken in conjunction with the appended claims.

BRIEF DESCRIPTION OF THE DRAWINGS

FIG. 2 shows a summary of results from the validation of the assay to measure biopterin in body fluids and tissues.

DETAILED DESCRIPTION OF THE INVENTION

Figure 1:
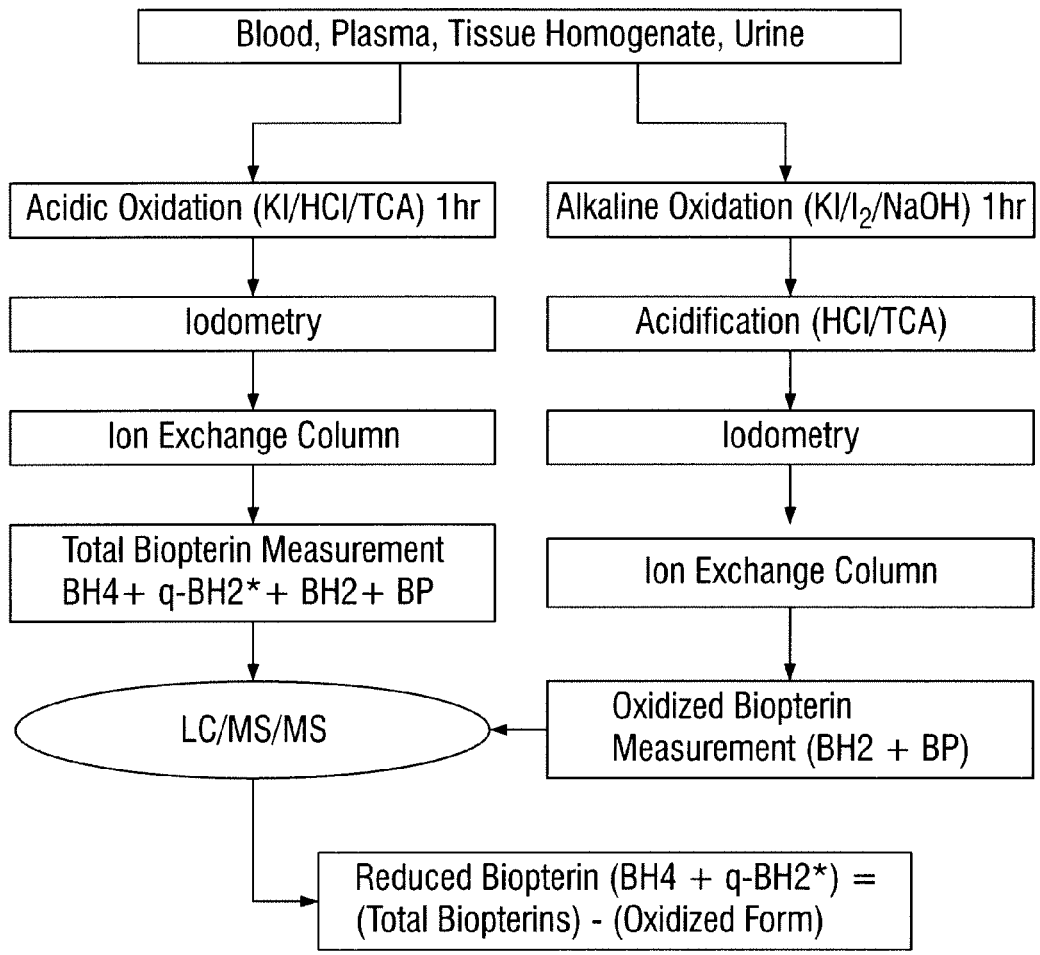
FIG. 1 shows a flow chart for the measurement of biopterin.

Orally administered tetrahydrobiopterin exhibits poor bioavailability in that the amount of drug entering the bloodstream oftentimes does not lead to effective therapy or requires administration of larger doses of the compound in order to achieve significant clinical benefit. Furthermore, while the blood-brain barrier is generally permeable to small molecules, for example, it is a natural barrier to the uptake of tetrahydrobiopterin. The present invention addresses the poor bioavailability of orally administered tetrahydrobiopterin and the difficulties in providing tetrahydrobiopterin to both the body and the CNS in amounts effective to provide therapy for conditions responsive to tetrahydrobiopterin.

The invention generally relates to analogs of tetrahydrobiopterin, pharmaceutical compositions containing the same, and methods of treating an individual suffering from a condition responsive to tetrahydrobiopterin by administration of the analog, all of which are described in more detail below.

The analogs can be particularly useful because BH4 is a natural product with multiple actions for which it is difficult to produce an analog that not only would be required to have improved bioavailability properties but also must retain ability to function with multiple cellular targets. Avoiding both inhibitory or unexpected toxic effects of an analog can be achieved with an analog (e.g., a prodrug) that converts to the natural compound after achieving entry into the bloodstream from the gastrointestinal tract.

Terminology

As used herein, the term "bioavailability" refers to the fraction of an administered dose of a drug entering systemic circulation. If the drug were administered intravenously, then its bioavailability theoretically would be 100%. However, if the drug were administered via other routes (such as orally), then its bioavailability typically would be less than 100% as a result of, for example, incomplete absorption in the GI tract, degradation or metabolism prior to absorption, and/or hepatic first pass effect.

As used herein, the term "alkyl" refers to straight chained and branched hydrocarbon groups, nonlimiting examples of which include methyl, ethyl, and straight chain and branched propyl and butyl groups. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, aryl, heteroaryl, cycloalkyl, heterocycloalkyl, and amino. It is specifically contemplated that in the analogs described herein according to Formula I, including any of the embodiments described herein, the alkyl group consists of 1-40 carbon atoms, or 1-25 carbon atoms, or 1-15 carbon atoms, or 1-12 carbon atoms, or 1-10 carbon atoms, or 1-8 carbon atoms, or 1-6 carbon atoms.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperidinyl, tetrahydrofuranyl, tetrahydropyranyl, dihydrofuranyl, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

As used herein, the term "alkenyl" is defined identically as "alkyl," except the group contains at least one carbon-carbon double bond.

As used herein, the term "alkylene" refers to an alkyl group having a substituent. For example, the term "alkylene heterocycloalkyl" refers to an alkyl group substituted with a heterocycloalkyl group. The alkylene group is optionally substituted with one or more substituent previously listed as an optional alkyl substituent.

As used herein, the term "alkenylene" is defined identical as "alkylene," except the group contains at least one carbon-carbon double bond.

As used herein, the term "aryl" refers to a monocyclic or polycyclic aromatic group. The aryl group can be, but is not limited to, a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "amino acid derivative" refers to a moiety having both a amine functional group, either as NH$_2$, NHR, or NR$_2$, and a carboxylic acid functional group. Amino acids can be alpha-amino acids, beta-amino acids, or gamma-amino acids. Unless specified otherwise, an amino acid structure referred to herein can be any possible stereoisomer, e.g., the D or L enantiomer. The amino acids can be naturally occurring amino acid such as L enantiomers of glycine, alanine, beta-alanine, leucine, isoleucine, aspartic acid, glutamic acid, glutamine, asparagine, arginine, cysteine, methionine, phenylalanine, tyrosine, tryptophan, histidine, lysine, proline, serine, threonine, or valine. Other amino acids can be used, such as the D enantiomers of glycine, alanine, beta-alanine, leucine, isoleucine, aspartic acid, glutamic acid, glutamine, asparagine, arginine, cysteine, methionine, phenylalanine, tyrosine, tryptophan, histidine, lysine, proline, serine, threonine, or valine, or other amino acids such as ornithine, substituted phenylalanines (e.g., 4-methoxyphenylaline), pyridiyl alanines, and the like. Amino acids can be synthesized according to known techniques, or can be purchased from suppliers, e.g., Sigma-Aldrich (Milwaukee, Wis.) or Chem-Impex International, Inc (Wood Dale, Ill.). The amino acid derivative can be, but is not limited to, valine, alanine, leucine, or isoleucine. For example, one class of embodiments is contemplated wherein the amino acid derivative can have two or more amino acids, e.g., as shown in the below compound of formula I, where R$_2$ is a γ-D-glutamic acid-D-alanine derivative:

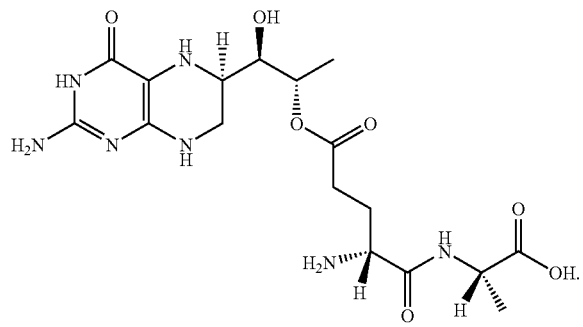

As used herein, the term "polyethylene glycol" refers to a chemical group of the formula RO(CH$_2$CH$_2$O—)$_n$, where R is an alkyl group and n is an integer of 1 to 1000, e.g., 10 to 500, 20 to 300, 25 to 250, or 30 to 200.

As used herein, the term "protecting group" refers to a chemical group that exhibits the following characteristics: (1) reacts selectively with the desired functionality in good yield to give a protected substrate that is stable to the projected reactions for which protection is desired; (2) is selectively removable from the protected substrate to yield the desired functionality; and (3) is removable in good yield by reagents compatible with the other functional group(s) generated in such protection reactions. Examples of protecting groups can be found in Greene et al., "Protective Groups in Organic Synthesis," 2d Ed. (John Wiley & Sons, Inc., New York, 1991).

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Analogs of Tetrahydrobiopterin

One embodiment of the invention is directed to analogs of tetrahydrobiopterin. The analogs of tetrahydrobiopterin can be, but are not limited to, prodrugs of tetrahydrobiopterin. An analog (e.g., a prodrug) of tetrahydrobiopterin can be a compound of Formula I (shown below) or a pharmaceutically acceptable salt thereof which, under various conditions, can be metabolized or transformed to provide tetrahydrobiopterin:

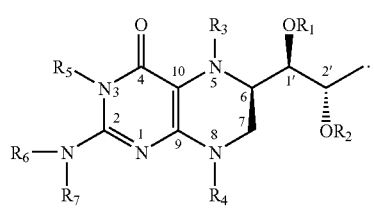

Formula I

Modifications at the C-1' and/or C-2' Positions

In an embodiment of the compound of Formula I, the compound is modified only at one or both of the C-1' and C-2' positions. In such an embodiment, $R_3$, $R_4$, $R_5$, $R_6$, and $R_7$ are all hydrogen, and $R_1$ and $R_2$ together are —C($R^c$)$R^d$— and form a five-membered ring, or $R_1$ and $R_2$ are independently hydrogen, $C_{3-8}$cycloalkyl, $C_{1-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkenyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$heterocycloalkyl, C(O)C$_{2-40}$alkenyleneC$_{3-8}$ heterocycloalkenyl, C(O)C$_{2-40}$alkenylenearyl, C(O)C$_{2-40}$alkenyleneheteroaryl, C(O)NR$^a$R$^b$, C(O)OR$^a$, or C(O)SR$^a$, with the proviso that $R_1$ and $R_2$ are not both hydrogen, C(O)H, glucosyl, aminoglucosyl, or the same C(O)C$_{1-10}$alkyl.

$R^a$ and $R^b$ are independently hydrogen, $C_{3-8}$cycloalkyl, $C_{1-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkenyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$heterocycloalkyl, C(O)C$_{2-40}$alkenyleneC$_{3-8}$heterocycloalkenyl, polyethylene glycol, C(O)C$_{2-40}$alkenylenearyl, or C(O)C$_{2-40}$alkenyleneheteroaryl.

$R^c$ and $R^d$ together are oxo, or $R^c$ and $R^d$ are independently hydrogen, $C_{3-8}$cycloalkyl, $C_{1-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkenyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$ heterocycloalkyl, C(O)C$_{2-40}$alkenyleneC$_{3-8}$ heterocycloalkenyl, C(O)C$_{2-40}$alkenylenearyl, or C(O)C$_{2-40}$alkenyleneheteroaryl.

Esters and diesters of BH4 are contemplated as analogs, and can be prodrugs, as disclosed herein. Primary and secondary alcohols are readily converted into esters by a variety of chemical reagents, such as, for example, acid chlorides (e.g., acetyl chloride) and acid anhydrides. An acid chloride (e.g., acetyl chloride) can react with the alcohol moiety in the presence of an acid scavenger (e.g., triethylamine) to form the corresponding ester and hydrochloric acid. Similarly, an acid anhydride (e.g., acetic anhydride) can react with the alcohol moiety to form the corresponding ester and acetic acid. Reactions with an acid anhydride are generally milder as the byproduct is the corresponding organic acid (e.g., acetic acid for acetic anhydride) as opposed to a mineral acid (e.g., hydrochloric acid for acetyl chloride). See e.g., Harden et al. (1989) J. Med. Chem. 32:1738-43. Tetrahydrobiopterin (a diol) can be converted by these and other reagents, as is known in the art. To selectively derivatize one or more hydroxyl groups in the presence of amine functionalities in tetrahydrobiopterin, the electronic nature and steric environment of these groups and functionalities can be exploited, with protection of these groups and functionalities as appropriate, as described in detail below.

Modifications at one or both of the C-1' and C-2' positions can be accomplished in a variety of ways. For example, tetrahydrobiopterin (also referred to hereinafter as "BH4") may be dissolved in a base-capturing solvent, such as, for example, pyridine or triethylamine. The dissolved BH4 may be reacted with a molar excess of an anhydride to form a monoester of BH4, and continuing the reaction to completion such that both hydroxyls at the C-1' and C-2' positions are converted to the diester analog (e.g., prodrug). Reaction Scheme (I) shown below depicts a representative synthesis suitable for modifying one or both of the C-1' and C-2' positions by use of an anhydride:

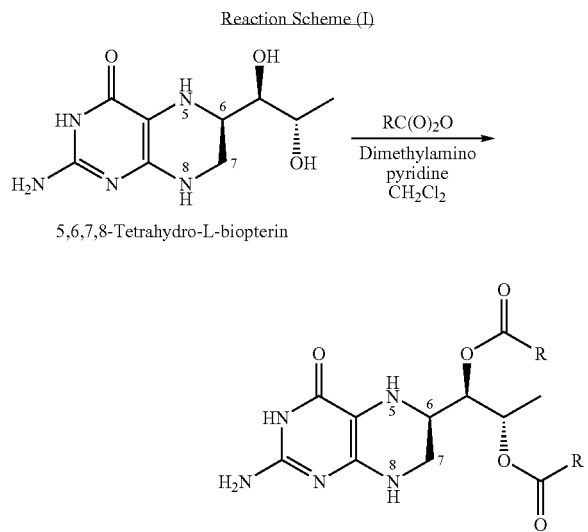

Alternative syntheses can include employing protecting groups to protect potentially reactive amines at the C-2, N-3, N-5, and N-8 positions.

The esters and diesters of BH4 contemplated as analogs as disclosed can be derived from amino acids, e.g., the 1',2'-diol of BH4 also can be converted into amino acid esters. The alcohol of acyclovir is converted into the L-valine amino acid ester, resulting in a significant increase in bioavailability, attributed to active transport thru the gut via human intestinal peptide transported hPEPT1. Other amino acids may work as well. Byproducts are biologically benign. Examples of amino acid (AA) derivatives that can be prepared are outlined in Reaction Schemes (IA), (IA'), and (IB). Reaction Scheme (IA) shows a method of preparing amino acid analogs of BH4, where the amino acid is at the C1', C2', or both positions. Reaction Scheme (IA') shows a particular example of an alternative involving direct deprotection of a di-Boc imine to final product using 4N HCl/dioxane. Reaction Scheme (IB) shows a method of preparing peptidyl derivatives of BH4, where C1', C2', or both are modified with a dipeptide, tripeptide, or tetrapeptide moiety. Longer peptide modifications can also be made using similar synthetic methods. Differentially protected amino acid derivatives can be obtained via known synthetic techniques or through commercial sources, such as Sigma-Aldrich (Milwaukee, Wis.) or Chem Impex (Wood Dale, Ill.).

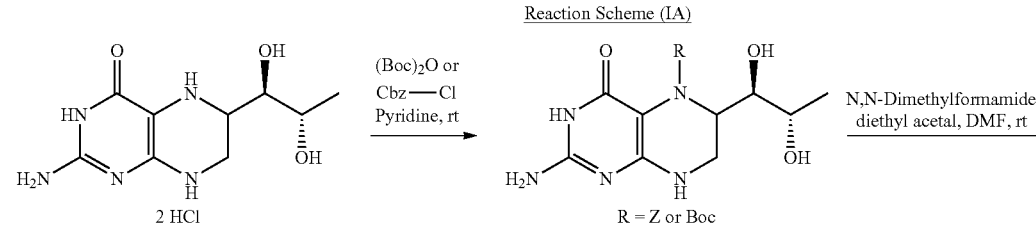

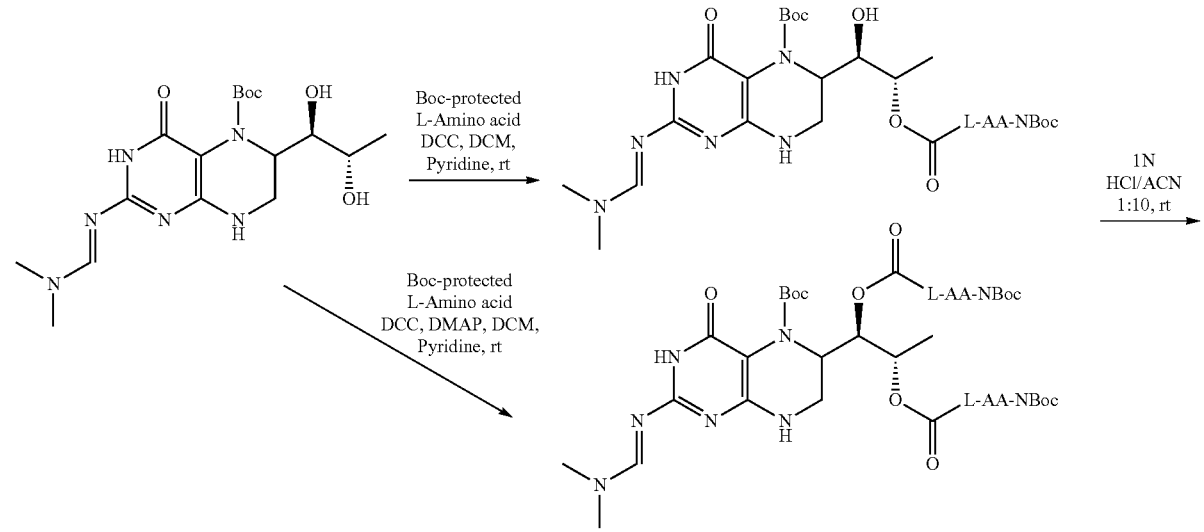

15 16
-continued
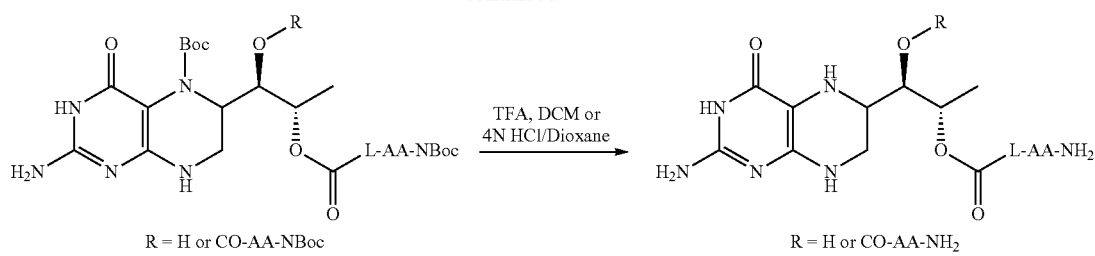
R = H or CO-AA-NBoc → R = H or CO-AA-NH₂
Reaction Scheme (IA')
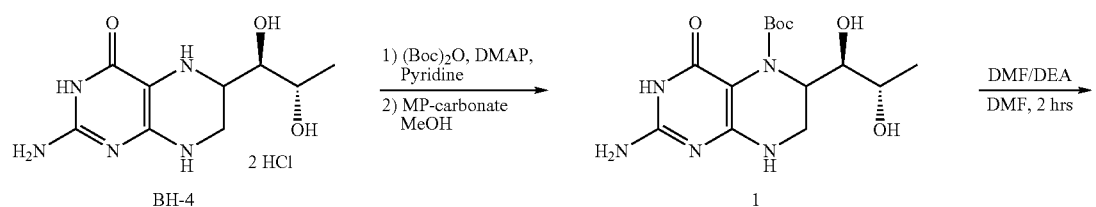
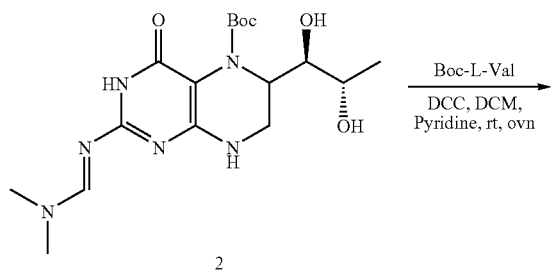
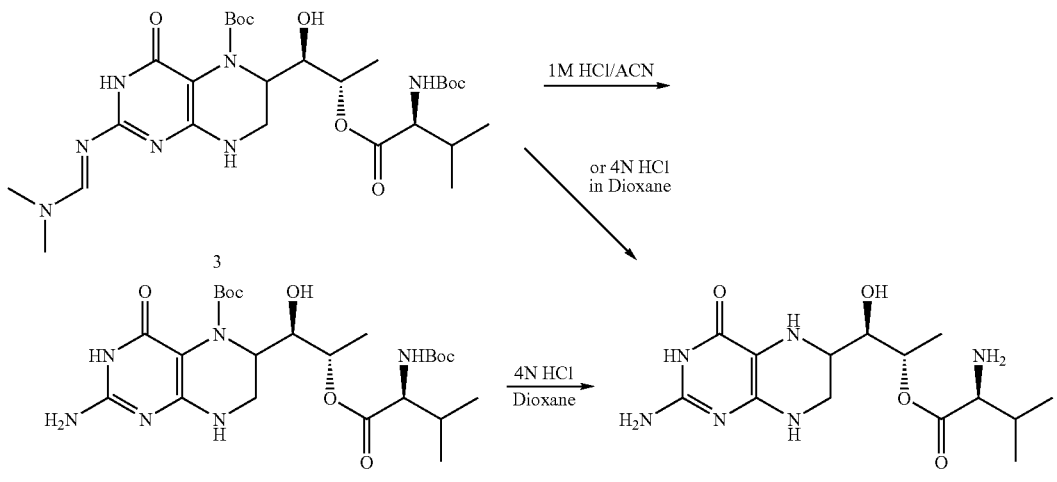

Reaction Scheme (IB)

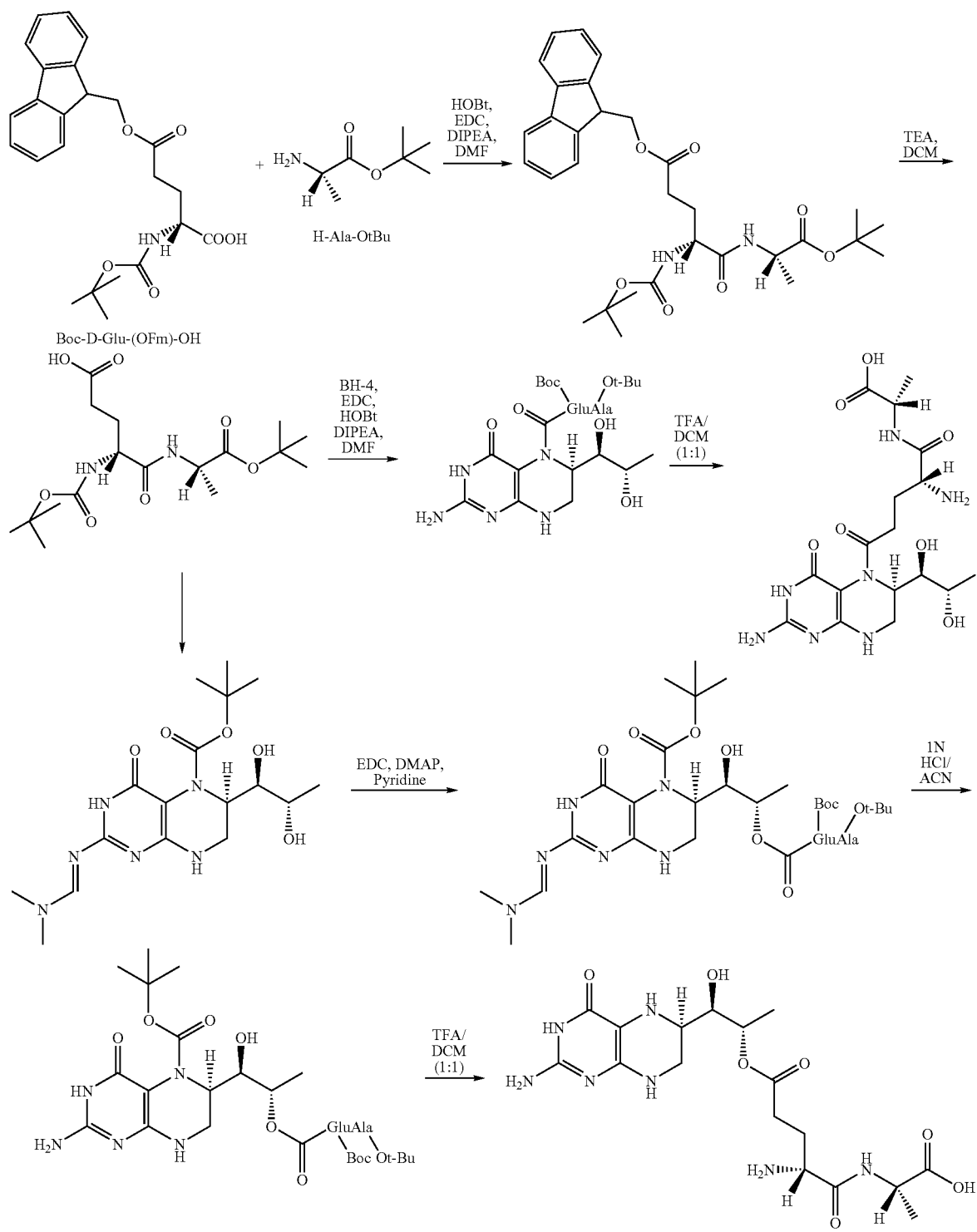

Cyclic ketals and acetals can be formed by reacting a diol with ketones and aldehydes, respectively. See e.g., See e.g., Harden et al. (1989) *J. Med. Chem.* 32:1738-43; Song et al. (2005) *J. Med. Chem.* 48:1274-77. Cyclic ketals and acetals can be converted either hydrolytically or enzymatically in vivo back into the diol. Modifications wherein $R_1$ and $R_2$ together are —$C(R^c)R^d$— and form a five-membered ring to form a ketal analog of BH4 can be achieved by reacting the 1',2'-diol of BH4 with an aldehyde (e.g., N,N-dimethylformamide (DMF)) with 2,2-dimethoxypropane and p-toluenesulfonic acid monohydrate (pTSA) to form a ketal analog of BH4, as set out in Reaction Scheme (II), shown below:

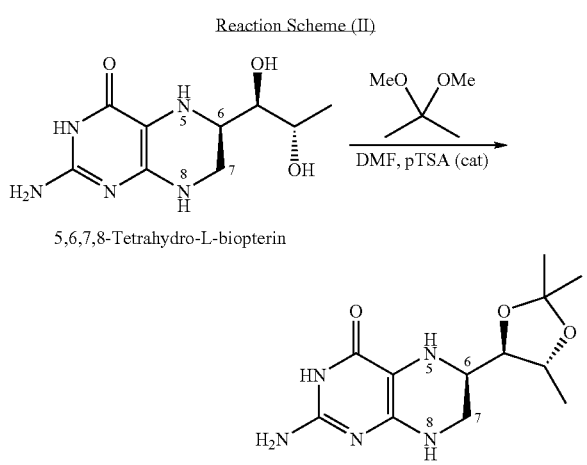

Modifications wherein $R_1$ and $R_2$ together are —$C(R^c)R^d$— and form a five-membered ring to form a ketal analog of BH4 can be achieved by reacting the 1',2'-diol of BH4 with a ketal or a ketone, and in the presence of a catalyst, as set out in Reaction Scheme (III), shown below:

Modifications at the N-5 and/or N-8 Positions

In another embodiment of the compound of Formula I, the compound is modified only at one or both of the N-5 and N-8 positions. In such an embodiment, $R_1$, $R_2$, $R_5$, $R_6$, and $R_7$ are all hydrogen; and, $R_3$ and $R_4$ are independently hydrogen, $C_{3-8}$cycloalkyl, $C_{2-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkenyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$heterocycloalkyl, C(O)C$_{2-40}$alkenyleneC$_{3-8}$heterocycloalkenyl, C(O)C$_{2-40}$alkenylenearyl, C(O)C$_{2-40}$alkenyleneheteroaryl, C(O)NR$^a$R$^b$, C(O)OR$^a$, or C(O)SR$^a$, with the proviso that when $R_3$, is hydrogen, then $R_4$ is not hydrogen or ribose, and when $R_4$, is hydrogen, then $R_3$ is not hydrogen, C(O)H, acetate, hydroxymethyl, or aminoalkyl. In one class of embodiments, $R_3$, is an amino acid derivative.

Modifications at one or both of the N-5 and N-8 positions can be accomplished in a variety of ways. For example, an amide (or di-amide) analog of BH4 may be obtained by treating BH4 with a molar excess of a suitable alcohol protecting group, such as t-butyldimethylsilyl chloride (TBDMSCl) in the presence of imidazole, to protect the reactive diol positions. Thereafter, the protected BH4 may be reacted with a base followed by reaction with an acid chloride to generate a protected N-5 and/or N-8 intermediate. Following these reactions, the diol positions on the intermediate are de-protected by treating the intermediate with a suitable de-protecting agent, e.g., in the case of TBDMSCl, tetra-n-butyl ammonium fluoride (TBAF), to produce an amide analog of BH4. The synthesis generally follows Reaction Scheme (IV), shown below:

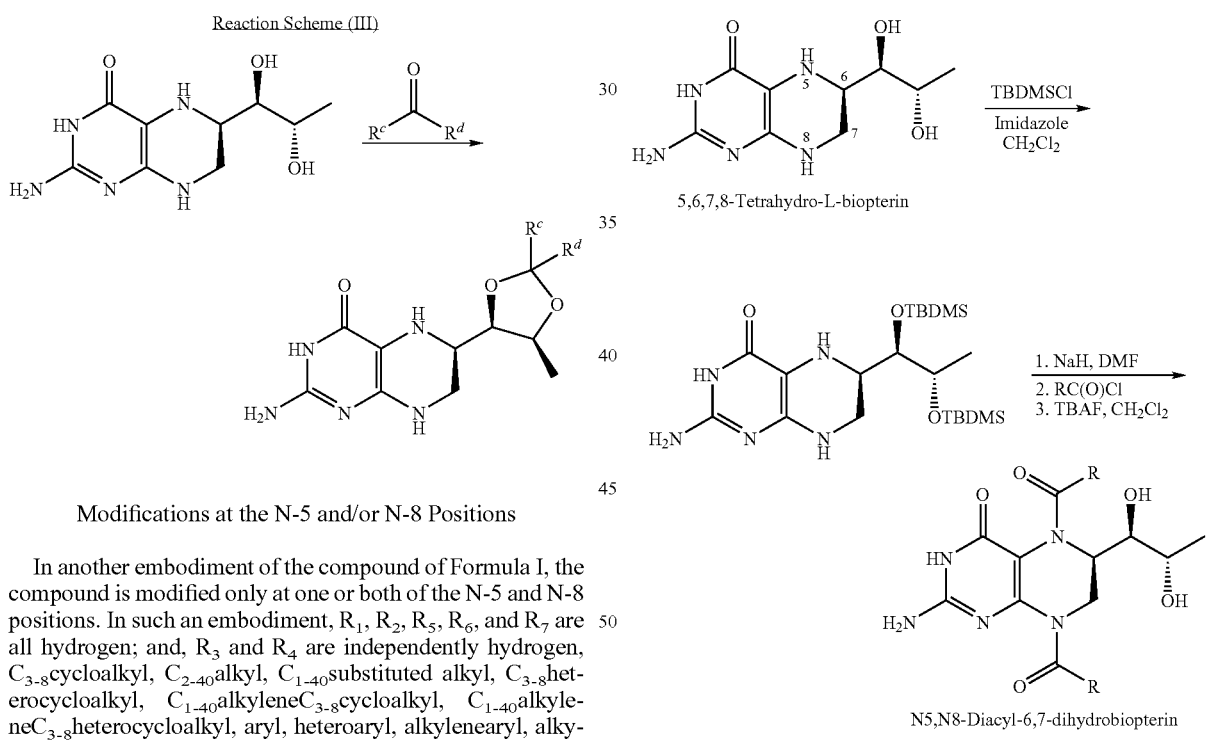

In another embodiment, a carbamoyl (or di-carbamoyl) analog of BH4 may be obtained by treating BH4 with a molar excess of an alcohol protecting group, such as TBDMSCl in the presence of imidazole, to protect the reactive diol positions. Thereafter, the protected BH4 may be reacted with a base followed by reaction with a chloroformate (e.g., butyryl chloroformate). Following these reactions, the diol positions on the intermediate are de-protected, e.g., by treating the intermediate with TBAF, to produce the di-carbamoyl analog of BH4. The synthesis generally follows Reaction Scheme (V), shown below:

Reaction Scheme (V)

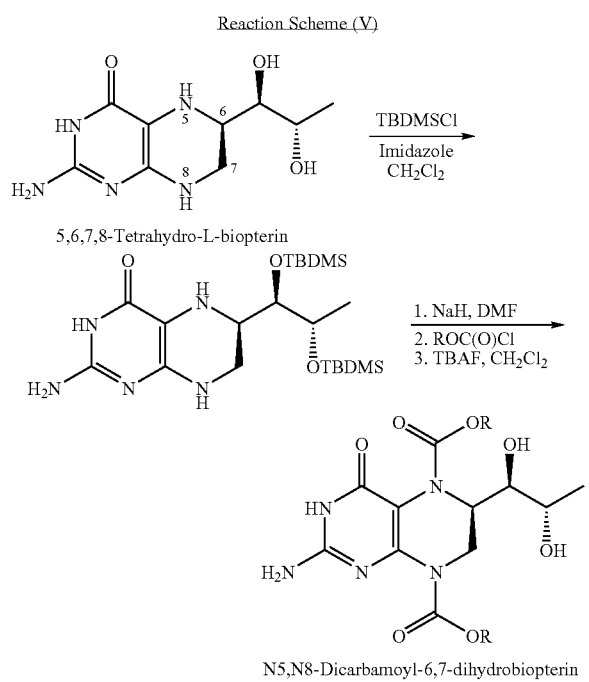

In yet another class of embodiments, the compound of Formula I is modified at the N-5 position with an amino acid or peptidyl moiety. Such derivatives can be prepared according to Reaction Scheme (VI), below.

Reaction Scheme (VI)

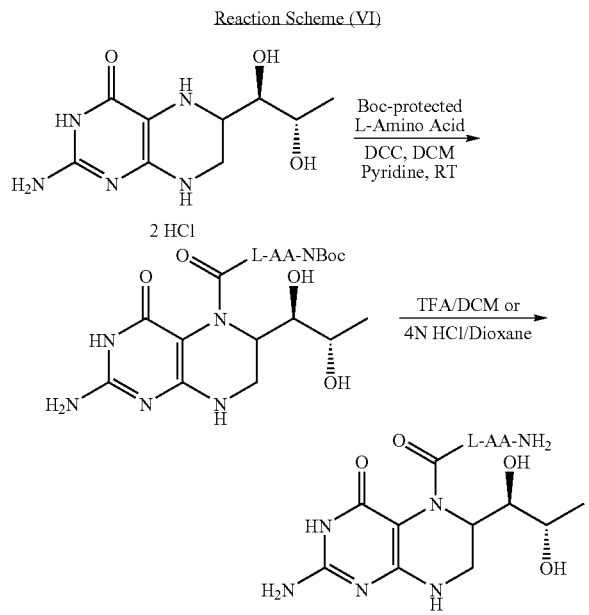

Modifications at the C-2 Position

In still another embodiment of the compound of Formula I, the compound is modified only at the C-2 position. In such an embodiment, $R_1$, $R_2$, $R_3$, $R_4$, and $R_5$ are all hydrogen; and, $R_6$, and $R_7$, are independently hydrogen, $C_{3-8}$cycloalkyl, $C_{1-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$heterocycloalkyl, C(O)C$_{2-40}$alkenyleneC$_{3-8}$heterocycloalkyl, C(O)C$_{2-40}$alkenylenearyl, C(O)C$_{2-40}$alkenyleneheteroaryl, C(O)NR$^a$R$^b$, C(O)OR$^a$, or C(O)SR$^a$, with the proviso that when $R_6$ is hydrogen, then $R_7$ is not hydrogen, methyl, CH$_2$(CH$_2$)$_4$ CO$_2$H, or CH$_2$CH$_2$-aryl, and when $R_7$ is hydrogen then $R_6$ is not hydrogen.

The modifications at C-2 can occur via a number of typical organic chemistry techniques, including protecting group manipulation of the diol portion of BH4 prior to modification of the NH$_2$ group at C-2, using known reactions for e.g., conversion of amines to amides, alkylation of amines, arylation of amines, and the like. The protected diol portion can optionally then be deprotected for provide analogs of BH4 modified at the C-2 position only.

Modifications at the N-3 Position

In yet another embodiment of the compound of Formula I, the compound is modified only at the N-3 position. In such an embodiment, $R_1$, $R_2$, $R_3$, $R_4$, $R_6$, and $R_7$ are all hydrogen; and, $R_5$, is $C_{3-8}$cycloalkyl, $C_{1-40}$alkyl, $C_{1-40}$substituted alkyl, $C_{3-8}$heterocycloalkyl, $C_{1-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)C$_{3-8}$cycloalkenyl, C(O)C$_{2-40}$alkenyl, C(O)C$_{2-40}$substituted alkenyl, C(O)C$_{3-8}$heterocycloalkenyl, C(O)C$_{2-40}$alkenyleneC$_{3-8}$cycloalkyl, C(O)C$_{2-40}$alkenyleneC$_{3-8}$cycloalkenyl, C(O)C$_{2-40}$alkenyleneC$_{3-8}$heterocycloalkyl, C(O)C$_{2-40}$alkenyleneC$_{3-8}$heterocycloalkyl, C(O)C$_{2-40}$alkenylenearyl, C(O)C$_{2-40}$alkenyleneheteroaryl, C(O)NR$^a$R$^b$, C(O)OR$^a$, or C(O)SR$^a$.

In each of the aforementioned embodiments of the compound of Formula I, R$^a$ and R$^b$ are independently hydrogen, $C_{3-8}$cycloalkyl, $C_{1-40}$alkyl, $C_{1-40}$substituted alkyl, $C_{3-8}$heterocycloalkyl, $C_{2-40}$alkyleneC$_{3-8}$cycloalkyl, $C_{1-40}$alkyleneC$_{3-8}$heterocycloalkyl, aryl, heteroaryl, alkylenearyl, alkyleneheteroaryl, $C_{3-8}$cycloalkenyl, $C_{2-40}$alkenyl, $C_{2-40}$substituted alkenyl, $C_{3-8}$heterocycloalkenyl, $C_{2-40}$alkenyleneC$_{3-8}$cycloalkyl, $C_{2-40}$alkenyleneC$_{3-8}$cycloalkenyl, $C_{2-40}$alkenyleneC$_{3-8}$heterocycloalkyl, $C_{2-40}$alkenyleneC$_{3-8}$heterocycloalkyl, $C_{2-40}$alkenylenearyl, $C_{2-40}$alkenyleneheteroaryl, C(O)H, C(O)C$_{3-8}$cycloalkyl, C(O)C$_{1-40}$alkyl, C(O)C$_{1-40}$substituted alkyl, C(O)C$_{3-8}$heterocycloalkyl, C(O)C$_{1-40}$alkyleneC$_{3-8}$cycloalkyl, C(O)C$_{1-40}$alkyleneC$_{3-8}$heterocycloalkyl, C(O)aryl, C(O)heteroaryl, C(O)alkylenearyl, C(O)alkyleneheteroaryl, C(O)$C_{3-8}$cycloalkenyl, C(O)$C_{2-40}$ alkenyl, C(O)$C_{2-40}$substituted alkenyl, C(O)$C_{3-8}$heterocycloalkenyl, C(O)$C_{2-40}$alkylene$C_{3-8}$cycloalkyl, C(O)$C_{2-40}$alkylene$C_{3-8}$cycloalkenyl, C(O)$C_{2-40}$alkylene$C_{3-8}$ heterocycloalkyl, C(O)$C_{2-40}$alkylene$C_{3-8}$ heterocycloalkenyl, polyethylene glycol, C(O)$C_{2-40}$alkenylenearyl, or C(O)$C_{2-40}$alkenyleneheteroaryl.

The modifications at the N-3 position can occur via a number of typical organic chemistry techniques, including protecting group manipulation of the diol portion of BH4 prior to modification of the amine, using known reactions for e.g., conversion of amines to amides, alkylation of amines, arylation of amines, and the like.

Acyl Derivatives of BH4

Also contemplated are modification of BH4 at C1', C2', and N5 to provide triacyl derivatives. Such compounds can be prepared as outlined in the below in Reaction Scheme (VII).

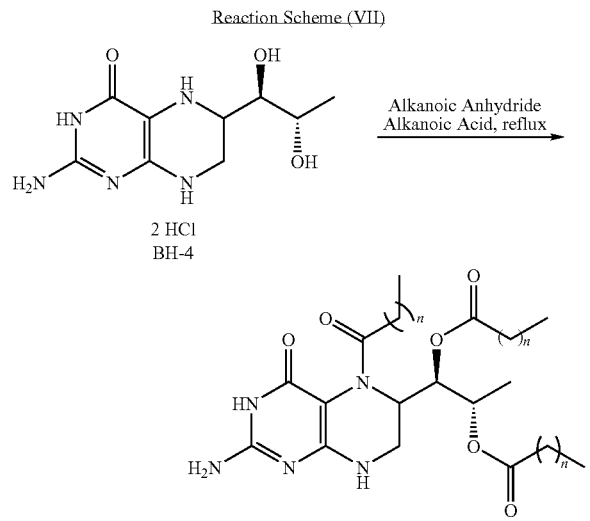

Methods of Evaluating Analogs of Tetrahydrobiopterin

The analogs of tetrahydrobiopterin disclosed herein may be evaluated in a variety of ways. For example, these analogs can be evaluated for metabolic stability. Drug metabolism is achieved via two major enzyme reactions with the liver. Phase 1 enzymes include the cytochrome 450 (CYP) family of enzymes located in the smooth endoplasmic reticulum. Phase I reactions include oxidation, reduction and/or hydrolysis, many of which are mediated by the CYP enzymes and require NADPH as a cofactor. Phase II reactions are located in the cytoplasm and endoplasmic reticulum and involve conjugation such as with glucuronic acid, glutathione, sulfate and glutamine. Phase II reactions may inactivate a drug and/or cause the drug molecule to be better eliminated by the body. Drugs may be metabolized by either the Phase I or Phase II reactions or by both. The metabolic stability of a test compound is determined to assess the ability of the compound to generate potentially toxic or pharmacologically inactive metabolites during phase 1 metabolism or to accumulate because of inadequate metabolic degradation. Liver microsomes are subcellular fractions (endoplasmic reticulum) that contain many drug-metabolizing enzymes, including CYPs. Liver microsomes are commonly used as an in vitro model system to evaluate the metabolic fate of test compounds. Other aspects of metabolic stability could relate to oxidation of tetrahydrobiopterin or derivatives. Tetrahydrobiopterin is sensitive to oxidation which can occur via metabolism or via physical action under the conditions of mammalian body in terms of temperature and redox potential. In addition, the analog may be tested for its metabolism via esterases and other enzymes that may cleave the analog and can be found in the tissues as well as in the bloodstream.

These analogs also can be evaluated for aqueous solubility as well as lipophilicity. Aqueous solubility is an important determinant of the bioavailability and usefulness of a drug candidate. Nephelometry (light scattering) is an accepted technique to rapidly determine the apparent solubilities of a large number of lead compounds. Lipophilicity can be determined using the octanol:water partition coefficient as model of membranes. The octanol:water partition coefficient can also be estimated using computer calculated fragment methods. A log of the partition coefficient (log P) of about 2 is thought to represent an optimal log P for membrane penetration.

Furthermore, these analogs can be evaluated for membrane permeability. CaCO-2 cells are commonly used to evaluate membrane permeability and, thus, potential oral bioavailability. CaCO-2 cells are derived from a human colon carcinoma cell line and are typically grown in confluent monolayer or porous membrane filters which are mounted in diffusion chambers. Membrane permeability is measured based on the rate of appearance of the test compound in the receiver compartment. The apical (donor) surface of the monolayer consists of microvillus and hence retains characteristics of the intestinal brush border. In addition, the cells can also express functional transport proteins and metabolic enzymes (Inui, et al., J. Pharmacol. Exp. Ther. 261:195-201 (1992); Lu, et al., Pharm. Res. 11:S-258 (1994); Jorge, et al., Pharm. Res. 8:1441-1443 (1991)). In vitro assessments using CaCO-2 cells are thought to be predictive for gastrointestinal absorption in humans (Stewart, et al., Pharm. Res. 12:693-699 (1995)). It has also been determined that Caco-2 cells derived from human intestine express a variety of esterases that can release parent drugs from prodrugs during passage across the intestinal membrane. (Imai et al., Drug Metabolism and Disposition 2005, 33, 1185-1190; Miyazaki et al., Antimicrobial Agents and Chemotherapy 2004, 48, 2604-2609). For example, a biphenyl hydroxlase-like protein that hydrolyzes valine esters of certain alcohols has been identified from CaCO-2 cells derived from human intestine. (Amidon, et al., J. Biol. Chem. 2003, 273, 25348-25356.)

Still further, these analogs can be evaluated for intestinal permeability. Assessment of the intestinal permeability of compounds intended for oral administration plays an important role in selecting candidates for commercial drug development. Ranking a series of lead compounds in order of absorption potential facilitates compound selection and optimization. A currently accepted method for investigation of the absorption potential of compounds within a series is by comparison of the apparent permeabilities through CaCO-2 or MDCK monolayer cultures (Artusson and Borchardt, Pharm. Res. 1997, 14, 1655-1657). These absorption models are also useful for understanding any absorption issues associated with compounds further advanced in development, including those involved with active transport mechanisms.

One can further evaluate analogs for their bioavailability and conversion to BH4 using animal models such as rats or dogs. In these situation, the orally administered drug is compared with that provided intravenously, and the pharmacokinetics of both routes are analyzed for drug concentration. The tissues of interest including the liver, the heart, the vascular system and the brain may be analyzed for tissue levels of tetrahydrobiopterin and compared with the concentrations achieved after administration of both analog and native forms.

Compositions Containing the Compound of Formula I

A further aspect of the invention is directed to a pharmaceutical composition that includes a compound of the present invention, together with a pharmaceutically acceptable excipient such as a diluent or carrier therefor. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., *Remington's Pharmaceutical Sciences*, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin. The amino acids, minerals and vitamins in the supplement should be provided in amounts that provide the recommended daily doses of each of the components.

As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Analog salts can be formed with inorganic or organic acids. Nonlimiting examples of alternative analog salt forms includes analog salts of acetic acid, citric acid, oxalic acid, tartaric acid, fumaric acid, and mandelic acid. In a specific embodiment, the analogs used in a composition described herein are formulated as a dihydrochloride salt.

Pharmaceutical compositions containing the analogs of the present invention can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a analog of the present invention is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% analog of the invention, e.g., from about 25 to about 90% analog of the invention.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. A particular embodiment is drawn to sugar alcohol solutions. When administered in liquid or suspension form, the composition can contain about 0.5 to about 90% by weight of a analog of the present invention, e.g., about 1 to about 50% of an analog of the present invention. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of an analog of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. In an embodiment, a composition for intravenous, cutaneous, or subcutaneous injection typically contains, in addition to a compound of the present invention, an isotonic vehicle. Such analog compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable analog compositions can include sterile aqueous solutions, suspensions, or dispersions and sterile powders for the extemporaneous preparation of sterile injectable solutions, suspensions, or dispersions. In all cases the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (for example, glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the analog in the case of dispersion and by the use of surfactants. The prevention of the action of microorganisms can be brought about by various antibacterial an antifungal agents, for example, parabens, chlorobutanol, phenol, sorbic acid, thimerosal, and the like. The compositions of the invention can contain isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

For oral administration, suitable compositions can be formulated readily by combining an analog of the present invention with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of Formula I with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

Nonlimiting examples of binders useful in a composition described herein include gum tragacanth, acacia, starch, gelatin, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol and esters or -ethers thereof, poly-vinylimidazole, poly-vinylpyrrolidone, and natural polymers like chitosan.

Nonlimiting examples of tableting excipients useful in a composition described herein include phosphates such as dicalcium phosphate.

Surfactants for use in a composition described herein can be anionic, cationic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, sodium oleate or sodium caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Nonlimiting examples of sweetening agents useful in a composition described herein include sugar alcohols such as mannitol, xylitol, sorbitol, glycerol, erythritol, arabitol, isomalt, maltitol and lactitol, as well as saccharin, sucralose and aspartame. In one embodiment, the sweetening agents are selected from sugar alcohols, aspartame, and sucralose. In another embodiment, the sweetening agents are not sugars. Nonlimiting examples of flavoring agents for use in a composition described herein include peppermint, oil of wintergreen or fruit flavors such as cherry and orange flavor.

Nonlimiting examples of coating materials useful in a composition described herein include talc, corn starch, silicon dioxide, sodium lauryl sulfate, gelatin, wax, shellac, sugar, biological degradable polymers, and metallic stearates. In an embodiment, the coating materials are selected from talc, corn starch, silicon dioxide, sodium lauryl sulfate, gelatin, wax, biological degradable polymers, and metallic stearates. The coating material may be present in the composition in an amount of from about 0.2 wt. % to about 15 wt. %, e.g., from about 0.5 wt. % to about 5 wt. %.

Lubricants which may be employed in the composition include, but are not limited to, natural or synthetic oils, fats, magnesium stearate, calcium stearate, sodium stearate, stearic acid, sodium stearyl fumarate, hydrogenated cotton seed oil (Sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, e.g., from about 0.5 wt. % to about 5 wt. %.

Nonlimiting examples of preservatives useful in a composition described herein include sorbic acid, chlorobutanol, thimerosal, benzyl alcohol, benzalkonium chloride, phenol, m-cresol, methyl p-hydroxybenzoate, benzoic acid, phenoxyethanol, methyl paraben, and propyl paraben and combinations of any of the above.

Nonlimiting examples of adjuvants useful in a composition described herein include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Typically, adjuvants such as Amphigen (oil-in-water), Alhydrogel (aluminum hydroxide), or a mixture of Amphigen and Alhydrogel are used.

Nonlimiting examples of antimicrobial agents useful in a composition described herein include triclosan, phenoxyisopropanol, phenoxyethanol, PCMX, natural essential oils and their key ingredients, and mixtures thereof.

Nonlimiting examples of antioxidants useful in a composition described herein include ascorbic acid (vitamin C), alpha tocopherol (vitamin E), vitamin A, selenium, beta-carotene, carotenoids, flavones, flavonoids, folates, flavanones, isoflavones, catechins, anthocyanidins, chalcones, and combinations thereof.

Slow release or sustained release formulations may also be prepared from the analogs described herein in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the analog may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The analogs can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the analogs in water-soluble form. Additionally, suspensions of the analogs can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Analogs of the present invention also can be formulated in rectal compositions, such as suppositories or retention enemas, e.g., containing conventional suppository bases. In addition to the formulations described previously, the analogs also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, an analog of the present invention can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A analog also can be injected parenterally, for example, intravenously, intramuscularly, subcutaneously, or intracoronarily. For parenteral administration, the analog is best used in the form of a sterile aqueous solution which can contain other substances, for example, salts, or sugar alcohols, such as mannitol, or glucose, to make the solution isotonic with blood.

For veterinary use, an analog of the present invention or a nontoxic salt thereof, is administered as a suitably acceptable formulation in accordance with normal veterinary practice. The veterinarian can readily determine the dosing regimen and route of administration that is most appropriate for a particular animal.

In certain aspects of the present invention, all the necessary components for the treatment of disease using analogs of BH4 either alone or in combination with another agent or intervention traditionally used for the treatment of such disease may be packaged into a kit. Specifically, the present invention provides a kit for use in the therapeutic intervention of the disease comprising a packaged set of medicaments that include analogs of BH4 or a derivative thereof as well as buffers and other components for preparing deliverable forms of said medicaments, and/or devices for delivering such medicaments, and/or any agents that are used in combination therapy with BH4-based medicaments, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Treatment Methods Utilizing the Compound of Formula I

As noted above, an aspect of the invention includes compositions containing an analog of tetrahydrobiopterin. A further aspect of the invention includes a method of treating an individual suffering from a BH4-responsive condition by administration of any one of the aforementioned compositions. The method includes administering to the individual a therapeutically effective amount of a compound of Formula I. BH4-responsive conditions generally include those sensitive to BH4 or a derivative thereof. BH4-responsive conditions include type I diabetes, type II diabetes, diabetic retinopathy, diabetic nephropathy, a vascular disease, hemolytic anemia (e.g., associated with hemolysis), sickle cell anemia, neuropsychiatric disorder, neuropsychiatric disorder associated with BH4 deficiency, neuropsychiatric disorder associated with reduced tyrosine hydroxylase function or reduced tryptophan hydroxylase function, a metabolic disorder such as Metabolic Syndrome, hypertension, peripheral arterial disease, intermittent claudication, critical limb ischemia, heart failure, atherosclerosis, endothelial dysfunction, and hyperphenylalanemia. These conditions are described in more detail below.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally a "therapeutically effective dose" refers to that amount of the analog that results in achieving the desired effect. For example, in one embodiment, a therapeutically effective amount of an analog of BH4 as disclosed herein increases the degree of vasodilation by 50 or 100% or more in response to normal signals such as 5 minutes of ischemia in flow-mediated dilation studies. In another embodiment, a therapeutically effective amount of an analog of BH4 as disclosed herein decreases systolic blood pressure by 5 mm Hg or 10 mm Hg or, in some patients, by 15 mm Hg or more. In yet another embodiment, a therapeutically effective amount of an analog of BH4 as disclosed herein reduces endothelial dysfunction as measured by flow-mediated dilation or other aspects such as expression of cell adhesion molecules, excess oxidative species generation or the tendency to promote coagulation or thrombosis. In still another embodiment, a therapeutically effective amount of an analog of BH4 as disclosed herein increases neurotransmitter levels of L-Dopa or serotonin by at least 10% in BH4-responsive patients.

Toxicity and therapeutic efficacy of the analogs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, which is expressed as the ratio between LD50 and ED50. Compounds which exhibit high therapeutic indices are preferred. The data obtained can be used in formulating a dosage range for use in humans. The dosage of such compounds preferably lies within a range of circulating concentrations that include the ED50 with little or no toxicity. The dosage can vary within this range depending upon the dosage form employed, and the route of administration utilized.

The exact formulation, route of administration, and dosage can be chosen by the individual physician in view of the particular disease being treated and the patient's condition. Dosage amount and interval can be adjusted individually to provide plasma levels of the analog of BH4, BH4, or combinations thereof, which are sufficient to maintain the therapeutic effects.

The amount of analog administered can be dependent on the subject being treated, on the subjects age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most appropriate dosage can be tailored to the individual subject, as is understood and determinable by one of skill in the art, without undue experimentation. This typically involves adjustment of a standard dose, e.g., reduction of the dose if the patient has a low body weight.

While individual needs vary, determination of optimal ranges of effective amounts of the analog is within the skill of the art. For administration to a human in the curative or prophylactic treatment of the conditions and disorders identified herein, for example, typical dosages of the analogs of the present invention can be about 0.1 milligrams of active moiety per kilogram body weight per day (mg/kg) to about 40 mg/kg, for example at least 0.2 mg/kg, at least 0.3 mg/kg, at least 0.4 mg/kg, or at least 0.5 mg/kg, for example 30 mg/kg or less or 20 mg/kg or less, which can about 2.5 mg/day (0.5 mg/kg×5 kg) to about 2000 mg/day (20 mg/kg×100 kg), for example. Such doses may be administered in a single dose or it may be divided into multiple doses. In exemplary embodiments, the daily dose may be 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg, or any fractions thereof.

Appropriate dosages may be ascertained through the use of established assays for determining blood levels of phenylalanine (Phe) in conjunction with relevant dose response data.

The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention may be useful in fields of human medicine and veterinary medicine. Thus the individual (or subject) to be treated may be a mammal, e.g., human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

While continuous, daily administration is contemplated, it may be desirable to cease therapy when specific clinical indicators are improved to above a certain threshold level. Of course, the therapy may be reinitiated in the event that clinical improvement indicators deteriorate. In practice, the physician determines the actual dosing regimen most suitable for an individual patient, and the dosage varies with the age, weight, and response of the particular patient. The above dose range is exemplary of the average case, but there can be individual instances in which higher or lower dosages are merited, and such are within the scope of this invention.

An analog of the invention can be administered alone or in conjunction with other therapeutics directed to the disease or directed to other symptoms thereof. The analog generally is administered in admixture with a pharmaceutically acceptable carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the analogs into preparations which can be used pharmaceutically.

BH4-Responsive Conditions

As disclosed above, BH4-responsive conditions include type I diabetes, type II diabetes, diabetic retinopathy, diabetic nephropathy, a vascular disease, hemolytic anemia, sickle cell anemia, neuropsychiatric disorder, neuropsychiatric disorder associated with BH4 deficiency, neuropsychiatric disorder associated with reduced tyrosine hydroxylase function or reduced tryptophan hydroxylase function, a metabolic disorder such as Metabolic Syndrome, hypertension, peripheral arterial disease, intermittent claudication, critical limb ischemia, heart failure, atherosclerosis, endothelial dysfunction, and hyperphenylalanemia.

Among the BH4-responsive conditions are type I diabetes, type II diabetes, diabetic retinopathy, and diabetic nephropathy. Diabetes mellitus and other cardiovascular disease states are characterized by loss of nitric oxide (NO) bioactivity resulting in altering the balance between vasodilators and vasoconstrictors in the endothelium and contributing to endothelial dysfunction. Endothelial dysfunction underlies the increased vasoconstriction resulting in hypertension, inadequate dilation response to flow or other signals, increased thrombogenesis and platelet aggregation, increased cell surface adhesion molecules such as the selectins, increased coagulation factors and accelerated atherosclerosis due to excess free radical production such as reactive oxygen species (ROS), e.g., superoxide molecules. Since NO plays a central role in maintaining vascular homeostasis, loss of NO bioactivity contributes to vascular disease pathogenesis and is a marker of adverse outcome of the diseases. In addition, the production of reactive oxidative species in the absence of adequate tetrahydrobiopterin also contributes to accelerated atherosclerosis Accelerated biosynthesis and catabolism of BH4 in arteries exposed to oxidative stress may contribute to the pathogenesis of the endothelial dysfunction known to exist in the arteries of patients suffering from diabetes. Additionally, elevated glucose may prevent an increase in cellular levels of BH4 due to the suppression of the first biosynthetic enzyme in the pathway to produce BH4 called GTP cyclohydrolase. Production of excess oxidative species via uncoupled endothelial nitric oxide synthase leads to further degradation of tetrahydrobiopterin and also contributes to reduced availability of BH4 levels to eNOS. The production of oxidative species by eNOS is enhanced by a limiting deficiency of BH4 and these oxidative species (e.g., superoxide leading to peroxynitrite) further destroy BH4, leading to a self sustaining downward spiral. Fortunately, in animals and humans, experimental supplementation of BH4 has demonstrated beneficial effects on endothelial function. It is contemplated that the analogs of BH4 disclosed herein may demonstrate similar beneficial effects but at substantially lower doses than native BH4. High-concentration BH4 supplementation studies using vessel rings from animals with diabetes or atherosclerosis and in mammary artery rings from patients with diabetes support the idea that BH4 could potentially ameliorate endothelial dysfunction, reduce oxidative stress, and restore vascular function. It is contemplated that the analogs of BH4 disclosed herein may similarly ameliorate endothelial dysfunction and restore vascular function. Some examples of the positive effects on BH4 on cardiovascular and diabetic subjects include: BH4 administration appears to augment NO-mediated effects on forearm blood flow in patients with diabetes or hypercholesterolemia but not normal subjects (Heitzer et al, Diabetologia. 43(11):1435-8 (2000)). Acute BH4 restores vascular function in venous grafts and arteries in diabetic subjects undergoing coronary artery bypass graft surgery (Guzik et al, Circulation 105(14):1656-1662 (2002)). BH4 increases insulin sensitivity in patients with Type II diabetes and coronary heart disease compared to control subjects (Nystrom et al, Am J Physiol Endocrinol Metab. 2004 November; 287(5):E919-25. Epub (2004)). Supplementation of BH4 precursors in the biosynthetic pathway has also been shown to assist in increased BH4 levels intracellularly, and improve NO synthesis in vivo and improve endothelial function.

Another of the BH4 responsive conditions is vascular disease. The vascular disease can be a disease selected from the group consisting of peripheral vascular disease, intermittent claudication, coronary artery disease, vascular disease associated with hypercholesterolemia, vascular disease associated with smoking, hypertension, recalcitrant or uncontrolled hypertension, pulmonary arterial hypertension, idiopathic pulmonary hypertension, pulmonary hypertension in the newborn (PPHN), atherosclerosis, stroke, post-stroke vasospasm, myocardial infarction, ischemia-reperfusion injury, congestive heart failure, post-transplant ischemia-reperfusion injury, post-transplant vascular injury, vasospasm, thrombogenesis, thrombosis, clotting, and coagulation.

Generally, treatment of vascular disease is directed at maintaining homeostasis, providing adjuvant therapy and providing specific therapy to improve clinical relevant endpoints These effects would be mediated through improved vasodilation in response to normal signals, reduced oxidative injury to the blood vessels and a general reduction and potentially reversal of atherosclerosis or other conditions prone to obstruction or thrombosis of the vascular system. These clinical endpoints can include the reduction in the incidence of myocardial infarction, hospitalization due to angina, death due to cardiovascular disease, poor peripheral perfusion causing the loss of limbs, and skin ulcers. Improved vascular function can be measured using flow-mediated dilation assessing the dilation of the brachial artery in response to 5 minutes of ischemia, or for peripheral perfusion may be measured using a graded treadmill test to assess the ability to walk without suffering calf pain or the amount of walking time that leads to pain. A patient may also be studied on an exercise test for the onset of angina or signs of decreased cardiac perfusion or performance. In addition, an echocardiogram may be conducted to assess the ejection fraction, cardiac output, diastiolic function, heart size, tricuspid regurgitation velocity and other signs of cardiac or vascular disease. The coronary vessels maybe examined via angiography to assess the perfusion of the heart in response to acetyl choline. Homeostasis is typically maintained by correcting factors that lead to vascular dysfunction, including low levels of BH4 and inadequate NO production, without generating damaging free radicals (e.g., superoxide radicals that lead to peroxynitrite). Adjuvant therapy typically includes administering agents or interventions that increase the effectiveness of the primary therapy. Specific therapy is directed at maintaining normal clinical relevant endpoints.

It is contemplated that the analogs of BH4 disclosed herein may be used to treat that patient population comprising subjects with various forms of vascular disease, including but not limited to recalcitrant or uncontrolled hypertension, intermittent claudication, coronary artery function, heart failure, pulmonary arterial hypertension and hemolytic anemias including Sickle Cell Disease, in the presence and absence of diabetes. Such analogs of BH4 disclosed herein may be administered alone or in combination with any other therapeutic agent and/or intervention that is commonly used for the treatment of vascular disorders. Agents used to treat diabetes include, but are not limited to, agents that improve insulin sensitivity such as PPAR gamma ligands (thiazolidinedones, glitazones, troglitazones, rosiglitazone (Avandia), pioglitazone), stimulators of insulin secretion such as sulphonylureas (gliquidone, tolbutamide, glimepride, chlorpropamide, glipizide, glyburide, acetohexamide) and meglitinides (meglitinide, repaglinide, nateglinide) and agents that reduce liver production of glucose such as metformin. Agents used to treat vascular disease include, but are not limited to, endothelin receptor antagonists commonly used for the treatment of hypertension and other endothelial dysfunction-related disorders, such as bosentan, darusentan, enrasentan, tezosentan, atrasentan, ambrisentan sitaxsentan; smooth muscle relaxants such as PDE5 inhibitors (indirect-acting) and minoxidil (direct-acting); angiotensin converting enzyme (ACE) inhibitors such as captopril, enalapril, lisinopril, fosinopril, perindopril, quinapril, trandolapril, benazepril, ramipril; angiotensin II receptor blockers such as irbesartan, losartan, valsartan, eprosartan, olmesartan, candesartan, telmisartan; beta blockers such as atenolol, metoprolol, nadolol, bisoprolol, pindolol, acebutolol, betaxolol, propranolol; diuretics such as hydrochlorothiazide, furosemide, torsemide, metolazone; calcium channel blockers such as amlodipine, felodipine, nisoldipine, nifedipine, verapamil, diltiazem; alpha receptor blockers such as doxazosin, terazosin, alfuzosin, tamsulosin; and central alpha agonists such as clonidine.

Agents used to treat hyperlipidemia include, but are not limited to, agents that lower LDL such as statins (atovastatin, fluvastatin, lovastatin, pravastatin, rosuvastatin calcium, simvastatin) and nicotinic acid, agents that stimulate PPAR alpha such as fibrates, gemfibrozil, fenofibrate, bezafibrate, ciprofibrate, agents that bind and prevent readsorption of bile acids and reduce cholesterol levels such as bile acid sequestrants, cholestyramine and colestipol, and cholesterol absorption inhibitors.

As stated above, disclosed herein are methods of treating vascular disease by administering to the subject a composition comprising an analog of BH4 alone or in combination with conventional vascular treatment, wherein the administration is effective to improve clinically relevant endpoints of said subject as compared to the concentration in the absence of the analog of BH4 alone or in combination with conventional vascular therapy. One embodiment of the invention can include administering an analog of BH4 to an individual with abnormal endpoints in an amount effective to normalize values. In an embodiment, the individual is diagnosed with the specific vascular disease. The invention contemplates administering an analog of BH4 described herein to patients diagnosed with a specific vascular disease characterized by specific symptoms and/or common tests used to diagnose a specific vascular disease in an amount effective to improve endpoints to normal levels.

Also among the BH4-responsive conditions are hemolytic anemia and sickle cell anemia. Some data exists that show that endothelial dysfunction occurs in patients with hemolytic anemias and lack of NO underlies the problem. BH4 deficiency is likely caused by oxidative destruction of BH4 pool or injury to the endothelium that results in decreased ability to biosynthesize and maintain BH4 pool levels. Animal studies suggest that NO plays a compensatory role in response to chronic vascular injury associated with sickle cell disease. The combined effects of circulating plasma hemoglobin and superoxide result in the destruction of NO (Reiter, et al., Current Opinions in Hematology 10:99-107 (2003)). New therapeutic approaches that increase the bioavailability of NO or counteract the oxidative stress and uncontrolled free radical proliferation associated with sickle cell disease have been considered. The co-administration of arginine with hydroxyurea may augment the production of NO and improve use of arginine in patients with SCD at steady state. See Morris et al. (2003) *J. Pediatric Hematology* 25:629-34. In addition to hydroxyurea and arginine, other therapies such as inhaled NO to increase NO levels, allopurinol to reduce NO destruction, and statins and sildenafil to amplify the NO response have been considered. See Mack et al., (2005, in press) *Intl. J. Biochem. Cell Biol*. U.S. patent application publication 2003/0078231 describes the use of the orthomolecular sulphoadenosylmethionine derivatives as a nutritional or food supplement with antioxidant properties to treat several diseases resulting from oxidative stress and uncontrolled free radical proliferation, including sickle cell anemia. U.S. patent application publication No. 2005/0239807 A1 describes the use of an inhibitor of reactive oxygen generating enzyme which includes a group providing NO donor bioactivity (e.g. allopurinol) to treat diseases associated with oxidative stress such as sickle cell anemia.

In sickle cell disease, NO reduces the endothelial expression of adhesion molecules and subsequent adhesion of red blood cells and leukocytes, thereby preventing the development of a vaso-occlusive crises. See Space et al. (2000) *Am. J. Hematology* 63:200-04. The cell-associated NADPH oxidase was shown to be a source of superoxide. See Wood et al.

(2005) *FASEB J.* 19:989-91. The rapid generation of superoxide radicals associated with Sickle Cell Disease may trigger the production of secondary reactive oxygen and nitrogen metabolites such as OH and ONOO which are known to oxidize BH4, thereby causing a deficiency in BH4. In one study, the administration of sepiapterin, a precursor of BH4, to sickle cell transgenic ($\beta^s$) mice was associated with an attenuation of blood cell adhesion. See Wood et al. (2006) *J. Free Radical Biology & Medicine* 40:1443-53. Although consistent with the present invention, the authors specifically indicate that sepiapterin lacks the anti- and auto-oxidative properties of exogenous BH4, the use of which is contemplated in the present invention. Further, transgenic sickle cell mouse models may not accurately reflect the complex homeostatic mechanisms that control the levels of NOS, NO and BH4 observed in humans. See Reiter et al. (2003) *Current Opinion in Hematology* 10:99-107. It is contemplated that the analogs of BH4 disclosed herein may be used similarly to BH4 to treat conditions like hemolytic anemia and sickle cell.

BH4 responsive conditions also include neuropsychiatric disorder, neuropsychiatric disorder associated with BH4 deficiency, and neuropsychiatric disorder associated with reduced tyrosine hydroxylase function or reduced tryptophan hydroxylase function. In one embodiment, the neuropsychiatric disorder is a disorder selected from the group consisting of Parkinson's Disease, attention deficit hyperactivity disorder, bipolar disease, autism, depression, and dystonia.

Generally, disorders of many neuropsychiatric disorders are related to decreased or inadequate levels of neurotransmitters. In depression, inadequate levels of serotonin may underlie depression and hence the use of serotonin reuptake inhibitors to increase the serotonin levels at the nerve terminals. BH4 is a required cofactor for serotonin biosynthesis and in deficient states, addition of BH4 can stimulate the production of serotonin as observed in some work studying serotonin levels in the platelets of PKU patients. It has also been observed that schizophrenic patients may have low catecholamine levels and low biopterin levels, and therefore the addition of BH4 may enhance the production of the catecholamine neurotransmitters due to BH4's role in the biosynthesis in the hydroxylation of tyrosine in the pathway to catecholamines. In addition, some research has suggested that BH4 may bind receptors at nerve terminals that alter the release of neurotransmitters which may be yet another role for BH4 in controlling neurotransmission. BH4 has also been proposed as a treatment for ADD/ADHD or hyperactivity syndromes in children. In these patients the use of stimulants help suppress the increased activity levels and allow better concentration. BH4 may increase or improve the production or release of stimulatory neurotransmitters and so increase the suppression of hyperactive behavior. It is contemplated that the analogs of BH4 disclosed herein may similarly be used like BH4 to treat neuropsychiatric disorder, neuropsychiatric disorder associated with BH4 deficiency, and neuropsychiatric disorder associated with reduced tyrosine hydroxylase function or reduced tryptophan hydroxylase function.

It is contemplated that a therapeutically effective amount of the analogs (e.g., prodrugs) of BH4 disclosed herein would increase tyrosine hydroxylase function or tryptophan hydroxylase function.

Another of the BH4-responsive conditions is metabolic syndrome. Generally, patients with metabolic syndrome demonstrate increased blood pressure, insulin resistance, hyperlipidemia, increased body mass index and increased atherosclerosis. The exact underlying etiology of metabolic syndrome is highly debated but it is clear that high fat/high carbohydrate diets and decreased exercise lead to obesity. BH4 levels may be low in this condition and may be part of the cause and progression of this syndrome. In the fructose-fed rat model leading to insulin resistance, BH4 levels are low and the replacement of BH4 improves the vascular effects of the insulin resistant state. It is contemplated that the analogs of BH4 disclosed herein may similarly be used like BH4 to treat metabolic syndrome.

Also among the BH4-responsive conditions is hyperphenylalanemia. In an embodiment, the hyperphenylalanemia is selected from the group consisting of mild phenylketonuria, classic phenylketonuria, and severe phenylketonuria (PKU), and also atypical or malignant hyperphenylalanemia associated with genetic deficiency in the biosynthesis or recycling of BH4, hyperphenylalanemia associated with liver disorder, and hyperphenylalanemia associated with malaria.

Generally, PKU is caused by a defect in the gene or expression or activity of the phenylalanine hydroxylase enzyme, leading to high phenylalanine blood levels. These high levels result in brain damage and other neurologic and physical disease including seizures, rashes, poor concentration, decreased executive function and white matter abnormalities in the brain. High phenylalanine levels are usually controlled through a severe medical diet that restricts phenylalanine intake. BH4 has been used in numerous published cases and series of reports to reduce blood Phe levels after oral ingestion (Blau et al 2002). Patients with PKU have been treated successfully for more than 5 years and have achieved clinically significant reductions in Phe level that allow the patients to reduce their dependence on the restrictive medical diet. In BH4 deficiency, administration of BH4 can greatly reduce blood phenylalanine levels and can improve neurotransmitter levels in the cerebrospinal fluid. However, adequate treatment of the brain disease is difficult due to poor CNS penetration by BH4. It is contemplated that the analogs of BH4 disclosed herein may similarly be used like BH4 to treat hyperphenylalanemia.

The present invention describes a pharmaceutical intervention of vascular disorders based on the administration of an analog of BH4. It is further contemplated that an analog, in a stabilized or other form may be used to treat that patient population comprising subjects with various forms of vascular disease in the presence or absence of diabetes, including but not limited to hypertension, recalcitrant or uncontrolled hypertension, pulmonary arterial hypertension, idiopathic pulmonary hypertension, pulmonary hypertension in the newborn (PPHN), and hemolytic anemias including Sickle Cell Disease, coronary artery disease, atherosclerosis of any arteries, including coronary, carotid, cerebral, or peripheral vascular arteries, stroke, post-stroke vasospasm, myocardial infarction, ischemia-reperfusion injury, congestive heart failure, post-transplant ischemia-reperfusion injury, post-transplant vascular injury, vasospasm, thrombogenesis, thrombosis, clotting, coagulation, damaged endothelium, insufficient oxygen flow to organs and tissues, elevated systemic vascular resistance (high blood pressure), vascular smooth muscle proliferation, progression of vascular stenosis (narrowing) and inflammation, ischemia-reperfusion injury, hypertension, diabetes, diabetic vasculopathy, cardiovascular disease, peripheral vascular disease, intermittent claudication, vascular disease associated with hypercholesterolemia, vascular disease associated with smoking, or neurodegenerative conditions stemming from ischemia and/or vascular inflammation.

Thus, treatment of any of these conditions is contemplated according to methods of the invention. Such BH4-based compositions may be administered alone or in combination with any other therapeutic agent and/or intervention that is commonly used for the treatment of relevant clinical symptoms or underlying disorders, including diabetes, vascular disease, hypertension, and hyperlipidemia, including the known therapeutic agents described herein.

Certain embodiments of the present invention are directed to treating vascular dysfunction administering to the subject a composition comprising an analog of BH4 or a precursor or derivative thereof alone or in combinations with conventional vascular treatment, wherein the administration of analog alone or in combination with conventional vascular therapy is effective to improve clinically relevant endpoints of said subject as compared to said concentration in the absence of the analog alone or in combination with conventional vascular therapy.

In exemplary embodiments, the analog of BH4 or precursor or derivative is administered in an amount effective to decrease blood pressure by about 5 mm Hg on average in BH4-responsive patients, or increases NO serum or urine levels by about 5%, 10%, 15%, 20%, or 30%, or up to about 200% on average in BH4-responsive patients.

It has also been suggested that the enhancement of nitric oxide synthase activity also results in reduction of elevated superoxide levels, increased insulin sensitivity, and reduction in vascular dysfunction associated with insulin resistance, as described in U.S. Pat. No. 6,410,535, incorporated herein by reference. Thus, treatment of diabetes (type I or type II), hyperinsulinemia, or insulin resistance is contemplated according to the invention. Diseases having vascular dysfunction associated with insulin resistance include those caused by insulin resistance or aggravated by insulin resistance, or those for which cure is retarded by insulin resistance, such as hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases or the like so far as they are associated with insulin resistance. It is contemplated that when administered to patients with these diseases, BH4 can prevent or treat these diseases by activating the functions of NOS, increasing NO production and suppressing the production of active oxygen species to improve disorders of vascular endothelial cells. It is also contemplated that downstream complications of diabetes, e.g. retinopathy or nephropathy may be reduced.

NO overproduction by nNOS has been implicated in strokes, migraine headaches, Alzheimer's disease, and with tolerance to and dependence on morphine. BH4 derivatives may be administered for any of these conditions. Other exemplary neuropsychiatric disorders for which BH4 derivatives may be administered include Parkinson's disease, Alzheimer's disease, schizophrenia, schizophreniform disorder, schizoaffective disorder, brief psychotic disorder, delusional disorder, shared psychotic disorder, psychotic disorder due to a general medical condition, substance-induced psychotic disorder, other psychotic disorders, tardive dyskinesia, Machado-Joseph disease, spinocerebellar degeneration, cerebellar ataxia, dystonia, chronic fatigue syndrome, acute or chronic depression, chronic stress syndrome, fibromyalgia, migraine, attention deficit hyperactivity disorder, bipolar disease, and autism. The neuropsychiatric disorder may be associated with reduced tyrosine hydroxylase function or reduced tryptophan hydroxylase function. Neuropsychiatric disorders herein optionally exclude Parkinson's disease, depression, and Alzheimer's disease BH4 derivatives may be co-administered according to the method of the invention with one or more other neuropsychiatric active agents, including antidepressants, neurotransmitter precursors such as tryptophan, tyrosine, serotonin, agents which activate noradrenergic systems, such as lofepramine, desipramine, reboxetine, tyrosine, agents which act prefentially on serotonin, combined inhibitors of both noradrenaline and serotonin uptake, such as venlafaxine, duloxetine or milnacipran, and drugs which are combined inhibitors of both dopamine and noradrenaline reuptake such as bupropion.

In exemplary embodiments, the amount of BH4 or precursor or derivative administered increases tyrosine hydroxylase function or tryptophan hydroxylase function by at least 5, 10, 15, 20, 25, 30, 35, 40%, 50, 75, or 100%, or increases neurotransmitter levels of L-Dopa or serotonin by at least 5, 10, 15, 20, 25, 30, 40%, 50, 75, or 100% in BH4-responsive patients.

Exemplary metabolic disorders include hyperphenylalanemia, e.g., mild phenylketonuria, classic phenylketonuria, severe phenylketonuria, atypical or malignant phenylketonuria associated with BH4 deficiency, hyperphenylalanemia associated with liver disorder, and hyperphenylalanemia associated with malaria. Exemplary patient populations include infants, children, teenagers, adults, females of childbearing age, and pregnant females. The individual can have a plasma phenylalanine concentration of greater than 1000 μM in the absence of treatment with (e.g., pre-treatment) the analog or precursor or derivative, and administration of the compound is in an amount effective to decrease the plasma phenylalanine concentration in the individual to less than about 1000 μM, or less than about 800 μM, or less than about 700 μM, or less than about 600 μM, or less than about 500 μM, or less than about 450 μM±15 μM.

EXAMPLES

The following examples are provided to illustrate the invention, but are not intended to limit the scope thereof.

Synthesis of BH4 Analogs

Example 1

BH4 Didodecanoate

This example describes the synthesis of an analog of BH4. BH4 is dissolved in a suitable solvent and reacted with a molar excess of dodecanoic acid chloride in the presence of imidazole. The reaction is stirred at room temperature overnight and the resulting diacyl BH4 analog is isolated and recrystallized.

Example 2

Acetic acid 2-acetoxy-1-(5-acetyl-2-amino-4-oxo-3,4,5,6,7,8-hexahydro-pteridin-6-yl)-propyl ester (Ac$_3$-BH4)

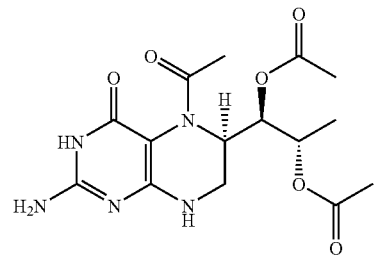

2-Amino-6-(1,2-dihydroxy-propyl)-5,6,7,8-tetrahydro-1H-pteridin-4-one dihydrochloride (0.1 g, 0.32 mmol) was slurried in acetic acid (3 ml). Acetic anhydride (300 uL, 3.2 mmol) was added and the mixture heated to reflux for 12 h. The reaction was concentrated and the crude material was purified by preparative RP-HPLC to give the final product as a white solid (0.096 g, 82%). $^1$H NMR (CD$_3$OD) δ 5.15 (dd, J=2.4 Hz, J=10 Hz, 1H), 4.95-4.90 (m, 1H), 3.36 (d, J=13.6 Hz, 1H), 3.22 (dd, J=4.4 Hz, J=13.2 Hz, 1H), 2.16 (s, 3H), 2.09 (s, 3H), 1.85 (s, 3H), 1.26 (d, J=6.4 Hz, 3H). MS: ESI (positive): 368 (M+H).

Example 3

Propionic acid 1-(2-amino-4-oxo-5-propionyl-3,4,5,6,7,8-hexahydro-pteridin-6-yl)-2-propionyloxy-propyl ester (Pr$_3$-BH4)

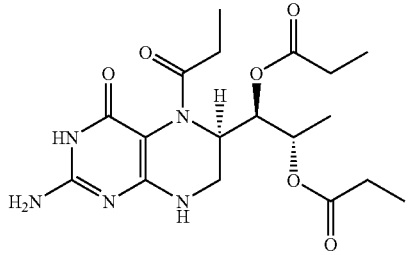

The title compound was prepared by the method described in example 2 using 2-amino-6-(1,2-dihydroxy-propyl)-5,6,7,8-tetrahydro-1H-pteridin-4-one dihydrochloride (0.2 g, 0.64 mmol), propionic anhydride (0.83 ml, 6.4 mmol) and propionic acid (6 ml) to give the product as a white solid (0.20 g, 75%). $^1$H NMR (DMSO-d$_6$) δ 10.11 (s, 1H), 6.99 (d, J=5.0 Hz, 1H), 6.23 (s, 2H), 4.96 (dd, J=2.5 Hz, J=10.1 Hz, 1H), 4.84-4.78 (m, 1H), 4.70 (dd, J=4.1 Hz, J=10.1 Hz, 1H), 3.15 (dd, J=5.3 Hz, J=13 Hz, 1H), 3.03 (dd, J=4.5 Hz, J=13 Hz, 1H), 2.67-2.57 (m, 1H), 2.40-2.35 (m, 2H), 2.27-2.20 (m, 1H), 2.15-2.03 (m, 2H), 1.17 (d, J=6.6 Hz, 3H), 1.05 (t, J=7.5 Hz, 3H), 0.92 (dt, J=1.8 Hz, J=7.5 Hz, 6H). MS: ESI (positive): 410 (M+H).

Example 4

Butyric acid 1-(2-amino-5-butyryl-4-oxo-3,4,5,6,7,8-hexahydro-pteridin-6-yl)-2-butyryloxy-propyl ester (Bu$_3$-BH4)

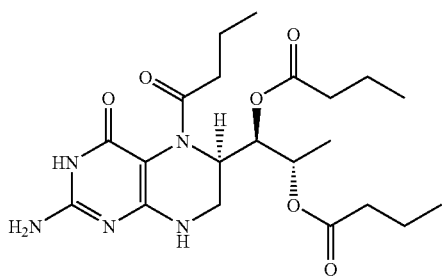

The title compound was prepared by the method described in example 2 using 2-amino-6-(1,2-dihydroxy-propyl)-5,6,7,8-tetrahydro-1H-pteridin-4-one dihydrochloride (0.2 g, 0.64 mmol), butyric anhydride (1.05 ml, 6.4 mmol) and butyric acid (6 ml) to give the product as a white solid (0.21 g, 71%). $^1$H NMR (CD$_3$OD) δ 5.18 (dd, J=2.4 Hz, J=10 Hz, 1H), 4.98-4.93 (m, 1H), 4.89-4.87 (m, 1H), 3.34 (s, 1H), 3.19 (dd, J=4.4 Hz, J=13.2 Hz, 1H), 2.62-2.54 (m, 1H), 2.45-2.39 (m, 1H), 2.36 (t, J=7.2 Hz, 2H), 2.10 (t, J=7.5 Hz, 2H), 1.70-1.47 (m, 6H), 1.27 (d, J=6.6 Hz, 3H), 0.98 (t, J=7.4 Hz, 3H), 0.90-0.85 (m, 6H). MS: ESI (positive): 452 (M+H).

Example 5

2-Amino-4-methyl-pentanoic acid 2-(2-amino-4-oxo-3,4,5,6,7,8-hexahydro-pteridin-6-yl)-2-hydroxy-1-methyl-ethyl ester dihydrochloride (Val-BH4)

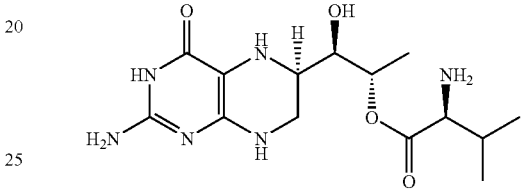

a.) 2-Amino-6-(1,2-dihydroxy-propyl)-4-oxo-4,6,7,8-tetrahydro-1H-pteridine-5-carboxylic acid tert-butyl ester To a stirred suspension 2-amino-6-(1,2-dihydroxy-propyl)-5,6,7,8-tetrahydro-1H-pteridin-4-one dihydrochloride (BH4, 5 g, 15.9 mmol) in pyridine (75 ml) under an atmosphere of nitrogen was added di-tert-butyl dicarbonate (5.2 g, 23.8 mmol). The mixture was stirred before the addition of more BH4 (5 g, 15.9 mmol) and di-tert-butyl dicarbonate (5.2 g, 23.8 mmol). 4-(Dimethylamino)pyridine (catalytic) was also added and the mixture was stirred under an atmosphere of nitrogen for 12 h at room temperature. The solvent was evaporated in vacuo and the residue placed under high vacuum for 24 h. The residue was dissolved in methanol (150 ml) and to the solution was added 30 g of MP-carbonate (Biotage, 3.14 mmol/g). The mixture was gently stirred at room temperature for 12 h. The mixture was filtered through celite and the filtrate evaporated in vacuo to give a yellow solid that was used without further purification. MS: ESI (positive): 342 (M+H).

b.) 6-(1,2-Dihydroxy-propyl)-2-(dimethylamino-methyleneamino)-4-oxo-4,6,7,8-tetrahydro-1H-pteridine-5-carboxylic acid tert-butyl ester The product of step a) was dissolved in 75 mL DMF and treated with N,N-dimethylformamide diethyl acetal (13 mL, 76.2 mmol). The mixture was stirred at room temperature for 2 h. The solvent was evaporated under high vacuum (temperature<50° C.). The residue was purified by silica-gel flash chromatography (gradient elution 0 to 20% methanol in DCM) to give the product as a light yellow solid (5.7 g, 45% yield over two-steps). $^1$H NMR (CD$_3$OD) δ 8.53 (s, 1H), 4.12 (dd, J=4.2 Hz, J=10.5 Hz, 1H), 3.90 (m, 1H), 3.77 (d, J=12.6 Hz, 1H), 3.42 (d, J=10.5 Hz, 1H), 3.26-3.18 (m, 1H), 3.15 (s, 3H) 3.07 (s, 3H), 1.46 (s, 9H), 1.20 (d, J=6.3 Hz, 3H). MS: ESI (positive): 397 (M+H).

c.) 6-[2-(2-tert-Butoxycarbonylamino-3-methyl-butyryloxy)-1-hydroxy-propyl]-2-(dimethylamino-methyleneamino)-4-oxo-4,6,7,8-tetrahydro-1H-pteridine-5-carboxylic acid tert-butyl ester To a stirred solution of N-Boc-L-Valine (19.12 g, 88 mmol) in dichloromethane (DCM, 40 ml) at 0° C. was added a solution of DCC (9.1 g, 44 mmol) in DCM (40 ml). The resulting solution was stirred for 1 h after which a white precipitate formed. The white solid was filtered and filtrate added to a stirred solution of the product of step b) (4.4 g, 11 mmol) dissolved in pyridine (200 mL). The mixture was stirred at room temperature under an atmosphere of nitrogen for 12 h. The reaction mixture was quenched by addition of methanol (20 ml). The solvent was evaporated in vacuo and the residue purified by flash silica-gel chromatography (gradient elution 0 to 6% methanol in DCM) to give the sub-title product as a light yellow solid (3.1 g, 47% yield, of an ~9:1 regioisomeric mixture by HPLC). $^1$H NMR (DMSO-$d_6$) δ 10.61 (s, 1H), 8.38 (s, 1H), 7.04 (d, J=8.7 Hz, 1H), 6.78 (d, J=4.5 Hz, 1H), 5.03 (d, J=3.6 Hz, 1H), 4.77 (d, J=5.7 Hz, 1H), 4.04-3.92 (m, 1H), 3.82-3.72 (m, 1H), 3.66-3.54 (m, 1H), 3.09 (s, 3H), 2.96 (s, 3H), 2.06-1.80 (m, 1H), 1.37 (s, 18H), 1.20 (d, J=6.6 Hz, 3H), 0.92-0.82 (m, 1H), 0.77 (d, J=6.6 Hz, 6H). MS: ESI (positive): 596 (M+H).

d.) 2-Amino-6-[2-(2-tert-butoxycarbonylamino-3-methyl-butyryloxy)-1-hydroxy-propyl]-4-oxo-4,6,7,8-tetrahydro-1H-pteridine-5-carboxylic acid tert-butyl ester The product of step c) (3.1 g, 5.15 mmol) was dissolved in acetonitrile (ACN, 130 ml) and treated with 1N HCl (13 ml, 13 mmol). The mixture was stirred at room temperature until no starting material was present (~18 h). The reaction mixture was neutralized by addition of a saturated solution of sodium bicarbonate. The solvent was then evaporated in vacuo (temp<40° C.) to give a light yellow solid. The solid was slurried in DCM (50 ml) and filtered. The filtrate was evaporated and the residue purified by flash silica-gel chromatography (gradient elution 0 to 20% methanol in DCM) to give the sub-titled product (1.75 g, 63%, ~9:1 regioisomeric mixture). $^1$H NMR (CD$_3$OD) δ 5.10-4.98 (m, 1H), 4.20-4.10 (m, 1H), 4.02-3.90 (m, 1H), 3.72 (d, J=12.3 Hz, 1H), 3.59 (d, J=9.6 Hz, 1H), 3.20 (dd, J=4.5 Hz, J=12.9 Hz, 1H), 2.16-1.96 (m, 1H), 1.46 (s, 9H), 1.42 (s, 9H), 1.30 (d, J=6.6 Hz, 3H), 0.88 (d, J=6.6 Hz, 3H), 0.84 (d, J=6.9 Hz, 3H). MS: ESI (positive): 541 (M+H).

e.) 2-Amino-3-methyl-butyric acid 2-(2-amino-4-oxo-3,4,5,6,7,8-hexahydro-pteridin-6-yl)-2-hydroxy-1-methyl-ethyl ester dihydrochloride The product of step d) (1.75 g, 3.24 mmol) was dissolved in dioxane (10 ml) and treated with 4N HCl/dioxane (80 mL, 320 mmol). The reaction mixture was stirred at room temperature under an atmosphere of nitrogen for 2 h. The product was isolated by filtration and dried in nitrogen purged vacuum oven at 45° C. to give 1.34 g (100%) of the title compound as a white solid. $^1$H NMR (CD$_3$OD) δ 5.11 (t, J=6.6 Hz, 1H), 4.22 (dd, J=2.4 Hz, J=6.9 Hz, 1H), 4.02 (d, J=4.5 Hz, 1H), 3.73 (d, J=11.4 Hz, 1H), 3.66 (s, 2H), 3.61-3.57 (m, 2H), 2.4-2.3 (m, 1H), 1.43 (d, J=6.3 Hz, 3H), 1.12-1.05 (dd, J=7.0 Hz, J=12 Hz, 6H). MS: ESI (positive): 341 (M+H).

f.) 2-Amino-3-methyl-butyric acid 2-(2-amino-4-oxo-3,4,5,6,7,8-hexahydro-pteridin-6-yl)-2-hydroxy-1-methyl-ethyl ester dihydrochloride As an alternative to method e,) the product of step c (0.5 g, 0.8 mmol) was dissolved in dioxane (5 mL) and treated with 4N HCl/dioxane (20 mL, 80 mmol) under an atmosphere of argon. After stirring at room temperature for 15 hours, a white solid was formed. This material was isolated and then dried to give 0.24 g (73%) of the title compound.

Example 6

2-Amino-3-methyl-pentanoic acid 2-(2-amino-4-oxo-3,4,5,6,7,8-hexahydro-pteridin-6-yl)-2-hydroxy-1-methyl-ethyl ester (Ile-BH4)

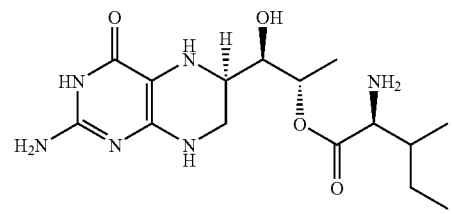

a.) 6-[2-(2-tert-Butoxycarbonylamino-3-methyl-pentanoyloxy)-1-hydroxy-propyl]-2-(dimethylamino-methyleneamino)-4-oxo-4,6,7,8-tetrahydro-1H-pteridine-5-carboxylic acid tert-butyl ester The product of Example 5, step b) was treated by the same method as that described in Example 5, step c) except N-Boc-L-Isoleucine (3.70 g, 16 mmol) was used to give the sub-title compound as a light yellow solid (0.29 g, 40%). The product obtained after chromatography still contained impurities and was used for the next step without further purification. MS: ESI (positive): 610 (M+H).

b.) 2-Amino-6-[2-(2-tert-butoxycarbonylamino-3-methyl-pentanoyloxy)-1-hydroxy-propyl]-4-oxo-4,6,7,8-tetrahydro-1H-pteridine-5-carboxylic acid tert-butyl ester The product of step a) (0.29 g, 0.48 mmol) was treated by the method described in Example 5, step d) except the residue from the reaction was purified by preparative RP-HPLC to give the sub-title compound as an off-white solid (0.10 g, 38%). $^1$H NMR (DMSO-$d_6$) δ 9.83 (s, 1H), 7.04 (d, J=8.7 Hz, 1H), 6.68 (d, J=4.8 Hz, 1H), 5.99 (s, 2H), 5.05 (bs, 1H), 4.74 (d, J=6.0 Hz, 1H), 4.04-3.90 (m, 1H), 3.88-3.78 (m, 1H), 3.56 (dd, J=4.8 Hz and J=12.3 Hz, 1H), 3.48-3.30 (m, 1H), 3.00 (dd, J=4.2 Hz and J=12.3 Hz, 1H), 1.78-1.60 (m, 1H), 1.37 (s, 18H), 1.18 (d, J=6.3 Hz, 3H), 1.16-1.00 (m, 2H) 0.77 (d, J=5.4 Hz, 3H), 0.75 (d, J=5.1 Hz, 3H). MS: ESI (positive): 555 (M+H).

c.) 2-Amino-3-methyl-pentanoic acid 2-(2-amino-4-oxo-3,4,5,6,7,8-hexahydro-pteridin-6-yl)-2-hydroxy-1-methyl-ethyl ester ditrifluoroacetate The product of step b) (0.1 g, 0.18 mmol) was treated with trifluoroacetic acid (2 ml, 27 mmol) in 2 ml of DCM. The mixture was stirred at room temperature under a nitrogen atmosphere for 1 h. The product was precipitated by the addition of 20 ml of diethyl ether. The product was filtered and dried in a nitrogen purged vacuum oven to give the title compound as a white solid (0.10 g, 100%). $^1$H NMR (CD$_3$OD) δ 5.11 (t, J=6.6 Hz, 1H), 4.09-4.07 (m, 1H), 4.05 (d, J=3.8 Hz, 1H), 3.60-3.54 (m, 2H), 3.43-3.38 (m, 1H), 2.07-

2.00 (m, 1H), 1.51-1.44 (m, 1H), 1.42 (d, J=6.3 Hz, 3H), 1.37-1.29 (m, 1H), 1.06 (d, J=7.0 Hz, 3H), 0.96 (t, J=7.4 Hz, 3H). MS: ESI (positive): 355 (M+H).

Example 7

2,6-Diamino-hexanoic acid 2-(2-amino-4-oxo-3,4,5,6,7,8-hexahydro-pteridin-6-yl)-2-hydroxy-1-methyl-ethyl ester tri-hydrochloride (Lys-BH4)

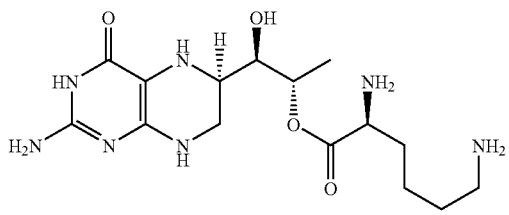

a.) 6-[2-(2,6-Bis-tert-butoxycarbonylamino-hexanoyloxy)-1-hydroxy-propyl]-2-(dimethylamino-methyleneamino)-4-oxo-4,6,7,8-tetrahydro-1H-pteridine-5-carboxylic acid tert-butyl ester The product of Example 5, step b) was treated by the same method as that described in Example 5, step d) except N-Boc-L-Lysine-N-Boc (8.26 g, 23.8 mmol) was used and after solvent evaporation in vacuo the crude material was dissolved in ethyl acetate and washed successively with 1N citric acid (2×), saturated sodium bicarbonate (2×), and brine. The organic layer was dried with sodium sulfate and solvent evaporated in vacuo. The crude product was purified flash silica-gel chromatography (gradient elution 0 to 8% methanol in DCM) to give the sub-title compound as a light yellow solid (2.55 g, 74%). The product obtained after chromatography still contained impurities and was used for the next step without further purification. $^1$H NMR (CD$_3$OD) δ 8.53 (s, 1H), 5.08-4.96 (m, 1H), 4.24-4.12 (m, 1H), 4.10-3.90 (m, 1H), 3.76 (d, J=12.3 Hz, 1H), 3.59 (d, J=11.4 Hz, 1H), 3.28-3.18 (m, 1H), 3.15 (s, 3H), 3.08 (s, 3H), 3.06-2.94 (m, 2H), 1.56-1.36 (m, 33H), 1.31 (d, J=6.6 Hz, 3H). MS: ESI (positive): 725 (M+H).

b.) 2-Amino-6-[2-(2,6-bis-tert-butoxycarbonylamino-hexanoyloxy)-1-hydroxy-propyl]-4-oxo-4,6,7,8-tetrahydro-1H-pteridine-5-carboxylic acid tert-butyl ester The product of step a) (2.55 g, 3.52 mmol) was treated by the method described in Example 5, step d) except the residue from the reaction was purified by preparative RP-HPLC to give the sub-title compound as an off-white solid (1.30 g, 55%). Analytical HPLC indicates the presence of two regioisomers in a ratio of 8:2. $^1$H NMR (CD$_3$OD) δ 5.08-4.96 (m, 1H), 4.22-4.10 (m, 1H), 4.10-3.96 (m, 1H), 3.72 (d, J=12.9 Hz, 1H), 3.61 (d, J=9.6 Hz, 1H), 3.28-3.16 (m, 1H), 3.08-2.94 (m, 2H), 1.86-1.36 (m, 33H), 1.30 (d, J=6.6 Hz, 3H). MS: ESI (positive): 670 (M+H).

c.) 2,6-Diamino-hexanoic acid 2-(2-amino-4-oxo-3,4,5,6,7,8-hexahydro-pteridin-6-yl)-2-hydroxy-1-methyl-ethyl ester tri-hydrochloride The product of step b) (1.30 g, 1.94 mmol) was treated by the method described in Example 5, step e) to give the title compound as a white solid (0.93 g, 100%). $^1$H NMR (CD$_3$OD) δ 5.09-5.04 (m, 1H), 4.24 (dd, J=2.7 Hz, J=7.2 Hz, 1H), 4.17 (t, J=6.3 Hz, 1H), 4.00 (t, J=6.3 Hz, 1H), 3.74-3.56 (m, 3H), 2.96 (t, J=7.7 Hz, 3H), 2.03-1.93 (m, 3H), 1.76-1.68 (m, 3H), 1.61-1.51 (m, 3H), 1.47 (d, J=6.3 Hz, 3H). MS: ESI (positive): 370 (M+H).

Example 8

4-Amino-4-(1-carboxy-ethylcarbamoyl)-butyric acid 2-(2-amino-4-oxo-3,4,5,6,7,8-hexahydro-pteridin-6-yl)-2-hydroxy-1-methyl-ethyl ester dihydrochloride

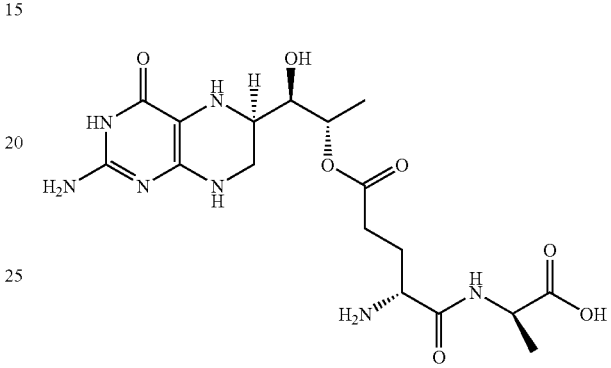

a.) 6-{2-[4-tert-Butoxycarbonylamino-4-(1-tert-butoxycarbonyl-ethylcarbamoyl)-butyryloxy]-1-hydroxy-propyl}-2-(dimethylamino-methyleneamino)-4-oxo-4,6,7,8-tetrahydro-1H-pteridine-5-carboxylic acid tert-butyl ester To a stirred solution of the product of Example 19, step b) (0.45 g, 1.20 mmol) in pyridine (10 ml) was added EDC (0.23 g, 1.20 mmol), and DMAP (0.15 g, 1.20 mmol). The mixture was stirred for 2 h at room temperature under an atmosphere of nitrogen followed by the addition of the product of Example 4, step c) (0.12 g, 0.30 mmol). The mixture was stirred for an additional 48 h. The solvent was evaporated in vacuo and the residue purified by preparative RP-HPLC to give the sub-title compound as a light yellow semi-solid (0.12 g, 55%). The product obtained after chromatography still contained impurities and was used for the next step without further purification. Analytical HPLC indicates a regioisomeric ratio of 10:1. MS: ESI (positive): 753 (M+H).

b.) 2-Amino-6-{2-[4-tert-butoxycarbonylamino-4-(1-tert-butoxycarbonyl-ethylcarbamoyl)-butyryloxy]-1-hydroxy-propyl}-4-oxo-4,6,7,8-tetrahydro-1H-pteridine-5-carboxylic acid tert-butyl ester The product of step a) (0.12 g, 0.16 mmol) was treated by the method described in Example 5, step d) except the residue from the reaction was purified by preparative RP-HPLC to give the sub-title compound as an off-white solid (0.048 g, 44%). $^1$H NMR (CDCl$_3$) δ 9.89 (s, 1H), 5.71 (bd, J=6.0 Hz, 2H), 5.08-4.90 (m, 1H), 4.88-4.68 (m, 1H), 4.66-4.54 (m, 1H), 4.32-4.10 (m, 1H), 4.08-3.96 (m, 1H), 3.88-3.70 (m, 2H), 3.36-3.26 (m, 1H), 2.40-1.76 (m, 6H), 1.74-1.58 (m, 1H), 1.56-1.36 (m, 27H), 1.31 (d, J=6.6 Hz, 3H). MS: ESI (positive): 698 (M+H).

c.) 4-Amino-4-(1-carboxy-ethylcarbamoyl)-butyric acid 2-(2-amino-4-oxo-3,4,5,6,7,8-hexahydro-pteridin-6-yl)-2-hydroxy-1-methyl-ethyl ester dihydrochloride The product of step b) (0.048 g, 0.07 mmol) was treated with trifluoroacetic acid (1 ml, 27 mmol) in 1 ml of DCM. The mixture was stirred at room temperature under an atmosphere of nitrogen for 2 h. The product was precipitated by the addition of 20 ml of diethyl ether. The product was filtered and dried in a nitrogen purged vacuum oven to give the title compound as a white solid (0.051 g, 98%). $^1$H NMR (CD$_3$OD) δ 4.45-4.39 (m, 2H), 4.23-4.20 (m, 2H), 3.94 (t, J=6.3 Hz, 1H), 2.60-2.55 (m, 2H), 2.49-2.24 (m, 2H), 2.17-2.12 (m, 3H), 1.45 (dd, J=7.4 Hz, J=9.7 Hz, 6H). MS: ESI (positive): 442 (M+H).

Example 9

Pyrrolidine-2-carboxylic acid 2-(2-amino-4-oxo-3,4,5,6,7,8-hexahydro-pteridin-6-yl)-2-hydroxy-1-methyl-ethyl ester dihydrochloride (Pro-BH4)

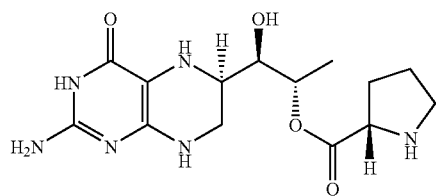

a.) Pyrrolidine-1,2-dicarboxylic acid 2-{2-[5-tert-butoxycarbonyl-2-(dimethylamino-methyleneamino)-4-oxo-3,4,5,6,7,8-hexahydro-pteridin-6-yl]-2-hydroxy-1-methyl-ethyl}ester 1-tert-butyl ester The product of Example 5, step b) was treated by the same method as that described in Example 5, step c) except N-Boc-L-Proline (13.6 g, 63.1 mmol) was used to give the sub-title compound as a tan solid (5.2 g, 69%). MS: ESI (positive): 594 (M+H).

b.) Pyrrolidine-1,2-dicarboxylic acid 2-[2-(2-amino-5-tert-butoxycarbonyl-4-oxo-3,4,5,6,7,8-hexahydro-pteridin-6-yl)-2-hydroxy-1-methyl-ethyl]ester 1-tert-butyl ester The product of step a) (5.2 g, 8.76 mmol) was treated by the same method as that described in Example 5, step d) except the reaction was stirred at room temperature for 24 h before the residue from the reaction was purified by flash silica-gel chromatography (gradient elution from 0-14% methanol in DCM) followed by separation of the regioisomeric mixture by preparative RP-HPLC to give the sub-title compound as a pale yellow solid (1.5 g, 32%). MS: ESI (positive): 539 (M+H). The other regioisomer was obtained as a white solid (0.6 g, 13%). MS: ESI (positive): 539 (M+H).

c.) Pyrrolidine-2-carboxylic acid 2-(2-amino-4-oxo-3,4,5,6,7,8-hexahydro-pteridin-6-yl)-2-hydroxy-1-methyl-ethyl ester dihydrochloride The product of step b) was treated by the same method as that described in Example 5, step e) except the reaction was stirred for 24 h to give the title compound as a pale yellow solid (1.2 g, 90%). $^1$H NMR (CD$_3$OD) δ 5.10 (m, 1H), 4.48 (t, J=7.9 Hz, 1H), 4.17 (dd, J=2.2 Hz, J=7.2 Hz, 1H), 3.73-3.66 (m, 1H), 3.57-3.55 (m, 2H), 3.44-3.36 (m, 3H), 2.51-2.43 (m, 1H), 2.18-2.05 (m, 3H), 1.43 (d, J=6.4 Hz, 3H). MS: ESI (positive): 339 (M+H).

Example 10

2-Amino-3-methyl-butyric acid 2-(2-amino-3-methyl-butyryloxy)-1-(2-amino-4-oxo-3,4,5,6,7,8-hexahydro-pteridin-6-yl)-propyl ester trihydrochloride (Val$_2$-BH4)

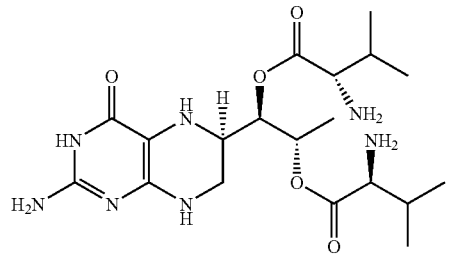

a.) 6-[1,2-Bis-(2-tert-butoxycarbonylamino-3-methyl-butyryloxy)-propyl]-2-(dimethylamino-methyleneamino)-4-oxo-4,6,7,8-tetrahydro-1H-pteridine-5-carboxylic acid tert-butyl ester To a stirred solution of N-Boc-L-Valine (9.08 g, 41.8 mmol) in dichloromethane (DCM, 20 ml) at 0° C. was added a solution of DCC (4.3 g, 20.9 g mmol) in DCM (20 ml). The resulting solution was stirred for 1 h after which a white precipitate formed. The white solid was filtered and filtrate added to a stirred solution of the product of Example 5, step b) (1.8 g, 4.54 mmol) dissolved in pyridine (75 ml). 4-(Dimethylamino)pyridine (catalytic) was added and the mixture was stirred at room temperature under an atmosphere of argon for 12 h. The reaction mixture was quenched by addition of methanol (20 ml) and the solvent was evaporated in vacuo. The crude material was dissolved in ethyl acetate and washed successively with 1N citric acid (2×), saturated sodium bicarbonate (2×), and brine. The organic layer was dried with magnesium sulfate and solvent evaporated in vacuo. The crude product was purified by flash silica-gel chromatography (gradient elution 0 to 5% methanol in DCM) to give the sub-title compound as a yellow solid (1.6 g, 45%). MS: ESI (positive): 795 (M+H).

b.) 2-Amino-6-[1,2-bis-(2-tert-butoxycarbonylamino-3-methyl-butyryloxy)-propyl]-4-oxo-4,6,7,8-tetrahydro-1H-pteridine-5-carboxylic acid tert-butyl ester The product of step a) (1.6 g, 2.02 mmol) was dissolved in acetonitrile (ACN, 50 ml) and treated with 1N HCl (5 ml, 5 mmol). The mixture was stirred at room temperature until no starting material was present (~20 h). The reaction mixture was neutralized by addition of a saturated solution of sodium bicarbonate. The solvent was evaporated in vacuo (temp<40° C.) to give a tan solid. The solid was slurried in methanol and filtered. The filtrate was evaporated and the residue purified by flash silica gel chromatography (gradient elution 0 to 12% methanol in DCM) to give the sub-title compound as a tan solid (0.45 g, 30%). $^1$H NMR (DMSO-$d_6$) δ 9.92 (s, 1H), 7.34 (d, J=7.5 Hz, 1H), 6.90 (d, J=8.4 Hz, 1H), 6.82 (s, 1H), 6.04 (s, 2H), 4.92 (d, J=7.8 Hz, 2H), 4.17 (bs, 1H), 3.84-3.72 (m, 2H), 3.25 (bs, 1H), 2.97 (d, J=8.7 Hz, 1H), 2.07-1.92 (m, 2H), 1.41-1.28 (m, 29H), 0.94 (d, J=6.6 Hz, 6H), 0.75 (d, J=6.6 Hz, 3H), 0.71 (d, J=6.9 Hz, 3H). MS: ESI (positive): 740 (M+H).

c.) 2-Amino-3-methyl-butyric acid 2-(2-amino-3-methyl-butyryloxy)-1-(2-amino-4-oxo-3,4,5,6,7,8-hexahydro-pteridin-6-yl)-propyl ester di hydrochloride The product of step c) (1.0 g, 1.35 mmol) was dissolved in dioxane (10 ml) under an atmosphere of argon and treated with 4 N HCl/dioxane (20 ml, 80 mmol). The reaction mixture was stirred at room temperature for 2 h. The product was isolated by filtration and dried in a nitrogen purged vacuum oven at 45° C. to give 0.78 g (100%) of the title compound as a tan solid. $^1$H NMR (CD$_3$OD) δ 5.50-5.41 (m, 2H), 4.10 (d, J=4.2 Hz, 1H), 4.00 (d, J=4.5 Hz, 1H), 3.66 (s, 2H), 3.61-3.55 (m, 1H), 3.46-3.40 (m, 1H), 2.42-2.32 (m, 2H), 1.47 (d, J=6.3 Hz, 3H), 1.47 (d, J=7.2 Hz, 3H), 1.09 (d, J=6.9 Hz, 6H), 1.05 (d, J=6.9 Hz, 3H). MS: ESI (positive): 440 (M+H).

Example 11

2,6-Diamino-hexanoic acid 2-(2-amino-4-oxo-3,4,5,6,7,8-hexahydro-pteridin-6-yl)-2-(2,6-diamino-hexanoyloxy)-1-methyl-ethyl ester pentahydrochloride (Lys$_2$-BH4)

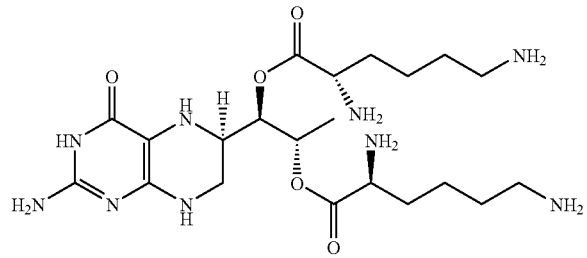

a.) 6-[1,2-Bis-(2,6-bis-tert-butoxycarbonylamino-hexanoyloxy)-propyl]-2-(dimethylamino-methylene-amino)-4-oxo-4,6,7,8-tetrahydro-1H-pteridine-5-carboxylic acid tert-butyl ester The product of Example 5, step b) was treated by the same method as that described in Example 10, step a) except N-Boc-L-Lysine-N-Boc (28.9 g, 83.5 mmol) was used to give the sub-title compound as a pale yellow solid (3.2 g, 33%). $^1$H NMR (CD$_3$OD) δ 8.56 (s, 1H), 7.19 (d, J=6.6 Hz, 1H), 5.13-5.05 (m, 2H), 4.40 (m, 1H), 4.08 (m, 1H), 3.94 (m, 2H), 3.43 (d, J=13.5 Hz, 1H), 3.17 (s, 3H), 3.09 (s, 3H), 3.05-2.95 (m, 4H), 1.82-1.70 (m, 3H), 1.47-1.39 (m, 48H), 1.26 (m, 2H). MS: ESI (positive): 1054 (M+H).

b.) 2-Amino-6-[1,2-bis-(2,6-bis-tert-butoxycarbonylamino-hexanoyloxy)-propyl]-4-oxo-4,6,7,8-tetrahydro-1H-pteridine-5-carboxylic acid tert-butyl ester The product of step a) (3.2 g, 3.03 mmol) was treated by the method described in Example 10, step b) to give the sub-title compound as a tan solid (1.46 g, 48%). $^1$H NMR (DMSO-$d_6$) δ 9.92 (s, 1H), 7.36 (d, J=6.0 Hz, 1H), 6.99 (d, J=8.1 Hz, 1H), 6.77-6.73 (m, 3H), 6.04 (s, 2H), 4.91 (d, J=8.7 Hz, 2H), 4.14 (bs, 1H), 3.87 (d, J=6.9 Hz, 1H), 3.72 (bs, 1H), 3.19 (bs, 1H), 2.97-2.85 (m, 6H), 1.62 (bs, 2H), 1.40-1.22 (m, 58H). MS: ESI (positive): 999 (M+H).

c.) 2,6-Diamino-hexanoic acid 2-(2-amino-4-oxo-3,4,5,6,7,8-hexahydro-pteridin-6-yl)-2-(2,6-diamino-hexanoyloxy)-1-methyl-ethyl ester pentahydrochloride The product of step b) (1.46 g, 1.46 mmol) was treated by the method described in Example 10, step c) to give the title compound as a tan solid (0.99 g, 68%). $^1$H NMR (CD$_3$OD) δ 5.52-5.48 (m, 1H), 5.42-5.39 (m, 1H), 4.32 (t, J=6.2 Hz, 1H), 4.14 (t, J=6.4 Hz, 1H), 3.65 (s, 1H), 3.57-3.50 (m, 1H), 3.25-3.22 (m, 1H), 2.98 (t, J=7.8 Hz, 4H), 2.16-1.89 (m, 4H), 1.79-1.71 (m, 4H), 1.61-1.56 (m, 4H), 1.45 (d, J=6.6 Hz, 3H). MS: ESI (positive): 498 (M+H).

Example 12

Pyrrolidine-2-carboxylic acid 1-(2-amino-4-oxo-3,4,5,6,7,8-hexahydro-pteridin-6-yl)-2-(pyrrolidine-2-carbonyloxy)-propyl ester trihydrochloride (Pro$_2$-BH4)

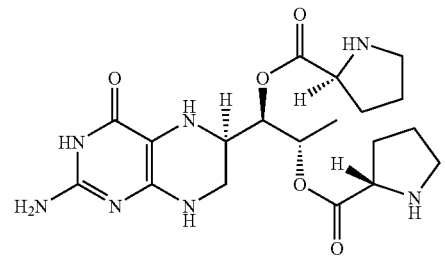

a.) Pyrrolidine-1,2-dicarboxylic acid 2-[2-(2-amino-5-tert-butoxycarbonyl-2-(dimethylamino-methylene-amino)-4-oxo-3,4,5,6,7,8-hexahydro-pteridin-6-yl-1-methyl-2-(1-tert-butoxycarbonyl-pyrrolidine-2-carbonyloxy)-ethyl]ester 1-tert-butyl ester The product of Example 5, step b) was treated by the same method as that described in Example 10, step a) except N-Boc-L-Proline (12.6 g, 5.87 mmol) was used to give the sub-title compound as a pale yellow solid (3.0 g, 60%). MS: ESI (positive): 791 (M+H).

b.) Pyrrolidine-1,2-dicarboxylic acid 2-[2-(2-amino-5-tert-butoxycarbonyl-4-oxo-3,4,5,6,7,8-hexahydro-pteridin-6-yl-1-methyl-2-(1-tert-butoxycarbonyl-pyrrolidine-2-carbonyloxy)-ethyl]ester 1-tert-butyl ester The product of step a) (3 g, 3.79 mmol) was treated by the method described in Example 10, step b) to give the sub-title compound as a tan solid (1.4 g, 50%). $^1$H NMR (CD$_3$OD) δ 5.19-5.14 (m, 2H), 4.31 (dd, J=4.4 Hz, J=8.1 Hz, 2H), 4.09-4.06 (m, 1H), 3.49-3.44 (m, 3H), 3.34 (m, 1H), 3.14 (m, 1H), 2.30 (m, 1H), 2.08-1.96 (m, 4H), 1.89-1.80 (m, 4H), 1.48 (s, 27H), 1.42 (m, 3H). MS: ESI (positive): 736 (M+H).

c.) Pyrrolidine-2-carboxylic acid 1-(2-amino-4-oxo-3,4,5,6,7,8-hexahydro-pteridin-6-yl)-2-(pyrrolidine-2-carbonyloxy)-propyl ester trihydrochloride The product of step b) (1.4 g, mmol) was treated by the method described in Example 10, step c) to give the title compound as a dark tan solid (0.85 g, 82%). $^1$H NMR (CD$_3$OD) δ 5.53-5.46 (m, 2H), 4.62 (t, J=8.4 Hz, 1H), 4.47 (t, J=8.4 Hz, 1H), 3.82-3.79 (m, 1H), 3.65-3.59 (m, 1H), 3.54-3.32 (m, 5H), 2.53-2.44 (m, 2H), 2.31-2.25 (m, 1H), 2.18-2.07 (m, 5H), 1.47 (d, J=6.6 Hz, 3H). MS: ESI (positive): 436 (M+H).

Example 13

2-Amino-5-(2-amino-3-methyl-butyryl)-6-(1,2-dihydroxy-propyl)-5,6,7,8-tetrahydro-1H-pteridin-4-one hydrochloride (N-Val-BH4)

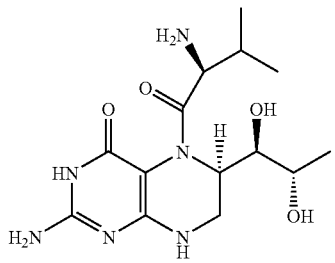

a.) {1-[2-Amino-6-(1,2-dihydroxy-propyl)-4-oxo-4,6,7,8-tetrahydro-1H-pteridine-5-carbonyl]-2-methyl-propyl}-carbamic acid tert-butyl ester To a stirred solution of N-Boc-L-Valine (4.56 g, 21 mmol) in DCM (15 ml) at 0° C. was added a solution of DCC (2.17 g, 10.5 mmol) in DCM (10 ml). The resulting solution was stirred for 1 h after which a white precipitate formed. The white solid was filtered and filtrate added to a stirred solution of 2-amino-6-(1,2-dihydroxy-propyl)-5,6,7,8-tetrahydro-1H-pteridin-4-one dihydrochloride (3.0 g, 9.55 mmol) dissolved in pyridine (80 mL). The mixture was stirred at room temperature under an atmosphere of nitrogen for 1.5 h. The reaction mixture was quenched by addition of methanol (20 ml). The solvent was evaporated in vacuo and the residue purified by preparative RP-HPLC to give the sub-title product as a tan solid (3.2 g, 76%). MS: ESI (positive): 441 (M+H).

b.) 2-Amino-5-(2-amino-3-methyl-butyryl)-6-(1,2-dihydroxy-propyl)-5,6,7,8-tetrahydro-1H-pteridin-4-one hydrochloride The product of step a) (3.13 g, 7.04 mmol) was dissolved in dioxane (10 ml) and treated with 4N HCl/dioxane (60 ml, 240 mmol). The reaction mixture was stirred at room temperature under a nitrogen atmosphere for 4 h. The product was isolated by filtration, recrystallized from isopropanol, and dried in a vacuum oven at 45° C. to give 1.15 g (43%) of the title compound as a tan solid. $^1$H NMR (CD$_3$OD) δ 4.64 (dd, J=4.2 Hz, J=10.2 Hz, 1H), 3.99 (d, J=6.9 Hz, 1H), 3.92 (d, J=13.2 Hz, 1H), 3.71 (m, 1H), 3.45 (dd, J=2.4 Hz, J=10 Hz, 1H), 3.27 (m, 1H), 2.17-2.10 (m, 1H), 1.20 (d, J=6.3 Hz, 3H), 0.95 (dd, J=4.8 Hz, J=6.9 Hz, 6H). MS: ESI (positive): 341 (M+H).

Example 14

2-Amino-5-(2-amino-3-methyl-pentanoyl)-6-(1,2-dihydroxy-propyl)-5,6,7,8-tetrahydro-1H-pteridin-4-one hydrochloride (N-Ile-BH4)

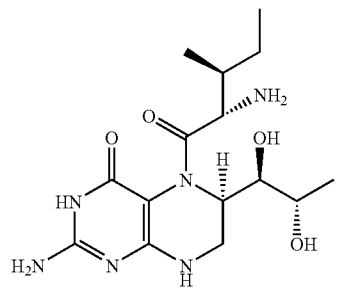

a.) {1-[2-Amino-6-(1,2-dihydroxy-propyl)-4-oxo-4,6,7,8-tetrahydro-1H-pteridine-5-carbonyl]-2-methyl-butyl}-carbamic acid tert-butyl ester The sub-titled compound was prepared by the method described in Example 13, step a) except N-Boc-L-Isoleusine (4.86 g, 21 mmol) was used. The crude material was dissolved in methanol and purified by preparatory RP-HPLC to give the sub-title compound as tan solid (3.48 g, 82%). MS: ESI (positive): 455 (M+H).

b.) 2-Amino-5-(2-amino-3-methyl-pentanoyl)-6-(1,2-di hydroxy-propyl)-5,6,7,8-tetrahydro-1H-pteridin-4-one hydrochloride The product of step a) was treated by the method described in Example 13, step b) to give the title compound as a pale yellow solid (1.67 g, 56%). $^1$H NMR (CD$_3$OD) δ 4.65 (dd, J=4.2 Hz, J=10.2 Hz, 1H), 4.04 (d, J=6.6 Hz, 1H), 3.94 (d, J=12.6 Hz, 1H), 3.70 (m, 1H), 3.45 (dd, J=2.4 Hz, J=10 Hz, 1H), 3.27 (m, 1H), 1.91-1.85 (m, 1H), 1.47-1.40 (m, 1H), 1.21 (d, J=6.3 Hz, 3H), 1.17-1.11 (m, 1H), 0.93-0.87 (m, 6H). MS: ESI (positive): 355 (M+H).

Example 15

2-Amino-5-(2,6-diamino-hexanoyl)-6-(1,2-dihydroxy-propyl)-5,6,7,8-tetrahydro-1H-pteridin-4-one dihydrochloride (N-Lys-BH4)

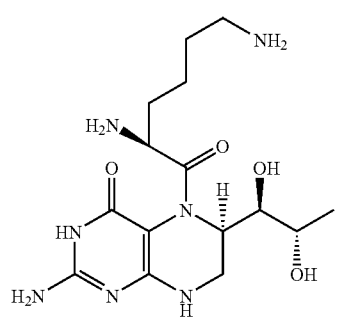

a.) {6-[2-Amino-6-(1,2-dihydroxy-propyl)-4-oxo-4,6,7,8-tetrahydro-1H-pteridin-5-yl]-5-tert-butoxycarbonylamino-6-oxo-hexyl}-carbamic acid tert-butyl ester The sub-titled compound was prepared by the method described in Example 13, step a) except N-Boc-L-Lysine-N-Boc (7.28 g, 21 mmol) was used. The crude material was dissolved in methanol and purified by preparatory RP-HPLC to give the sub-title compound as a tan solid (2.16 g, 40%). MS: ESI (positive): 570 (M+H)

b.) 2-Amino-5-(2,6-diamino-hexanoyl)-6-(1,2-dihydroxy-propyl)-5,6,7,8-tetrahydro-1H-pteridin-4-one hydrochloride The product of step a) was treated by the method described in Example 13, step b) except no recrystallization was needed to give the title compound as a white solid (1.1 g, 48%). ¹H NMR (CD₃OD) δ 4.64 (dd, J=4.2 Hz, J=10.2 Hz, 1H), 4.26 (t, J=6.6 Hz, 1H), 3.94 (d, J=13 Hz, 1H), 3.72-3.66 (m, 1H), 3.46 (dd, J=2.6 Hz, J=10.2 Hz, 1H), 2.90 (t, J=7.5 Hz, 2H), 1.86-1.75 (m, 2H), 1.67-1.59 (m, 2H), 1.40-1.33 (m, 2H), 1.20 (d, J=6.6 Hz, 3H). MS: ESI (positive): 370 (M+H).

Example 16

2-Amino-6-(1,2-dihydroxy-propyl)-5-(pyrrolidine-2-carbonyl)-5,6,7,8-tetrahydro-1H-pteridin-4-one dihydrochloride (N-Pro-BH4)

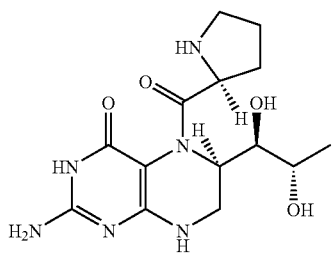

a.) 2-[2-Amino-6-(1,2-dihydroxy-propyl)-4-oxo-4,6,7,8-tetrahydro-1H-pteridine-5-carbonyl]-pyrrolidine-1-carboxylic acid tert-butyl ester The sub-titled compound was prepared by the method described in Example 13, step a) except N-Boc-L-Proline (4.5 g, 21 mmol) was used. The crude material was dissolved in methanol and stirred with MP-carbonate (Biotage, 3.14 g/mmol) before purification by preparatory RP-HPLC to give the product as white solid (2 g, 48%). ¹H NMR (DMSO-d₆) δ 9.87 (s, 1H), 7.00 (d, J=5.4 Hz, 1H), 6.26 (s, 2H), 4.87 (dd, J=3.3 Hz, J=8.7 Hz, 1H), 4.61 (d, J=4.8 Hz, 1H), 4.31 (dd, J=4.5 Hz, J=10.2 Hz, 1H), 4.11 (d, J=5.7 Hz, 1H), 3.62 (t, J=6.0 Hz, 1H), 3.52 (dd, J=5.7 Hz, J=12.3 Hz, 1H), 3.26-3.16 (m, 3H), 2.95 (dd, J=4.8 Hz, J=10 Hz, 1H), 1.89-1.82 (m, 1H), 1.65-1.54 (m, 2H), 1.35 (s, 10H), 0.97 (d, J=6.3 Hz, 3H). MS: ESI (positive): 439 (M+H).

b.) 2-Amino-6-(1,2-dihydroxy-propyl)-5-(pyrrolidine-2-carbonyl)-5,6,7,8-tetrahydro-1H-pteridin-4-one dihydrochloride The product of step a) was treated by the method described in Example 13, step b) except no recrystallization was needed to give the title compound as a white solid (1.63 g, 69%). ¹H NMR (D₂O) δ 4.73 (t, J=8.2 Hz, 1H), 4.58 (dd, J=4.0 Hz, J=10.2 Hz, 1H), 3.79 (d, J=13 Hz, 1H), 3.73 (dd, J=2.5 Hz, J=6.4 Hz, 1H), 3.54 (dd, J=2.5 Hz, J=10.2 Hz, 1H), 3.43-3.35 (m, 3H), 2.33-2.24 (m, 1H), 2.03-1.96 (m, 2H), 1.83-1.75 (m, 1H), 1.17 (d, J=6.5 Hz, 3H). MS: ESI (positive): 339 (M+H).

Example 17

2-Amino-5-butyryl-6-(1,2-dihydroxy-propyl)-5,6,7,8-tetrahydro-1H-pteridin-4-one (N-Bu-BH4)

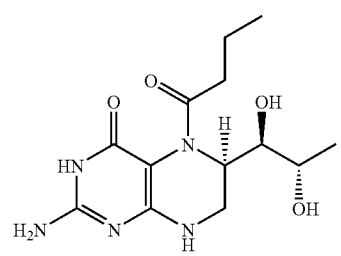

2-Amino-5-butyryl-6-(1,2-dihydroxy-propyl)-5,6,7,8-tetrahydro-1H-pteridin-4-one

The title compound was prepared by the method described in Example 5 using 2-amino-6-(1,2-dihydroxy-propyl)-5,6,7,8-tetrahydro-1H-pteridin-4-one dihydrochloride (0.5 g, 1.59 mmol), butyric anhydride (0.31 ml, 1.91 mmol), pyridine (7.5 ml) and catalytic 4-(dimethylamino)pyridine to give the product as a yellow solid (0.27 g, 55%). ¹H NMR (CD₃OD) δ 4.62 (dd, J=4.0 Hz, J=10.4 Hz, 1H), 3.78 (m, 1H), 3.74 (d, J=12.4 Hz, 1H), 3.44 (dd, J=2.4 Hz, J=10.4 Hz, 1H), 3.18 (dd, J=4.8 Hz, J=12.8 Hz, 1H), 2.56-2.49 (m, 1H), 1.42-1.34 (m, 1H), 1.63-1.52 (m, 2H), 1.15 (d, J=6.8 Hz, 3H), 0.87 (t, J=7.4 Hz, 3H). MS: ESI (positive): 312 (M+H).

Example 18

2-{2-Amino-5-[2-amino-6-(1,2-dihydroxy-propyl)-4-oxo-4,6,7,8-tetrahydro-1H-pteridin-5-yl]-5-oxo-pentanoylamino}-propionic acid trifluoroacetate

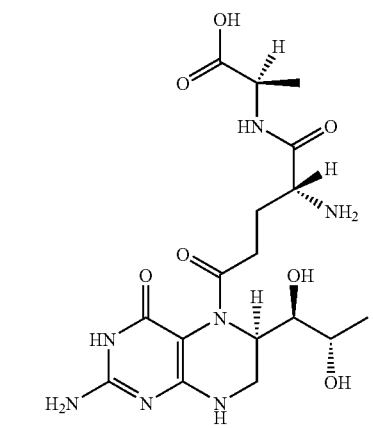

a.) 2-{5-[2-Amino-6-(1,2-dihydroxy-propyl)-4-oxo-4,6,7,8-tetrahydro-1H-pteridin-5-yl]-2-tert-butoxy-carbonylamino-5-oxo-pentanoylamino}-propionic acid To a stirred suspension of 2-amino-6-(1,2-dihydroxy-propyl)-5,6,7,8-tetrahydro-1H-pteridin-4-one dihydrochloride (0.55 g, 1.76 mmol) and the product from Example 19, step b) (0.66 g, 1.76 mmol) in DMF was added HOBt hydrate (0.24 g, 1.76 mmol), EDC (0.51 g, 2.64 mmol), and DIPEA (1.1 ml, 6.17 mmol). The mixture was stirred for 16 h at room temperature under an argon atmosphere. The solvent was evaporated in vacuo and the crude residue was purified by RP-preparatory HPLC to isolate the sub-title compound as a white solid (0.145 g, 14%). $^1$H NMR (DMSO-d$_6$) δ 9.92 (s, 1H), 7.99 (d, J=6.6 Hz, 1H), 6.99 (s, 1H), 6.77 (d, J=9.3 Hz, 1H), 6.23 (bs, 2H), 4.61 (d, J=5.1 Hz, 1H), 4.36 (d, J=6.3 Hz, 1H), 4.11-4.06 (m, 2H), 3.81 (m, 1H), 3.50 (m, 2H), 3.21 (m, 1H), 2.98 (m, 1H), 2.65 (m, 2H), 2.22 (m, 1H), 1.82 (m, 1H), 1.68 (m, 1H), 1.36 (s, 18H), 1.22 (d, J=6.3 Hz, 3H), 0.95 (d, J=6.3 Hz, 3H). MS: ESI (positive): 598 (M+H)

b.) 2-{2-Amino-5-[2-amino-6-(1,2-di hydroxy-propyl)-4-oxo-4,6,7,8-tetrahydro-1H-pteridin-5-yl]-5-oxo-pentanoylamino}-propionic acid The product of step a) was dissolved in 1:1 TFA:DCM and stirred at room temperature for 1.5 h. The solvent was removed in vacuo and the residue dissolved in a small amount of ethanol. Ethyl acetate was added to the solution until solid started to precipitate. The solution was stored in the freezer for 14 h and filtered to isolate the title compound as a white solid (60 mg, 56%). $^1$H NMR (CD$_3$OD) δ 4.61 (dd, J=4.2 Hz, J=10.2 Hz, 1H), 4.39 (q, J=7.2 Hz, 1H), 3.84 (t, J=6.3 Hz, 1H), 3.77-3.71 (m, 2H), 3.45 (dd, J=2.4 Hz, J=10.2 Hz, 1H), 3.25 (dd, J=4.2 Hz, J=12.6 Hz, 1H), 3.01-2.93 (m, 1H), 2.68-2.59 (m, 1H), 2.18-2.09 (m, 2H), 1.43 (d, J=7.2 Hz, 3H), 1.16 (d, J=6.3 Hz, 3H). MS: ESI (positive): 442 (M+H).

Example 19

4-tert-Butoxycarbonylamino-4-(1-tert-butoxycarbonyl-ethylcarbamoyl)-butyric acid

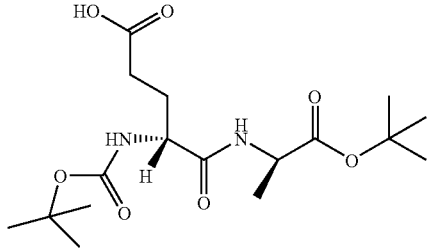

a.) 4-tert-Butoxycarbonylamino-4-(1-tert-butoxycarbonyl-ethylcarbamoyl)-butyric acid 9H-fluoren-9-ylmethyl ester To a stirred solution of Boc-D-Glu(OFm) (2.5 g, 5.88 mmol) and HOBt hydrate (0.79 g, 5.88 mmol) in DMF (50 ml) was added DIPEA (1.1 ml, 6.46 mmol), H-Ala-OtBu HCl (1.07 g, 5.88 mmol), and EDC (1.69 g, 8.81 mmol). The mixture was stirred for 16 h at room temperature under an atmosphere of argon. The solvent was evaporated in vacuo and the crude residue was dissolved in ethyl acetate, washed successively with saturated sodium bicarbonate (3×) and 5% aqueous acetic acid (3×). The organic layer was dried with magnesium sulfate and solvent evaporated in vacuo. The crude product was purified by flash silica-gel chromatography (gradient elution 0-40% ethyl acetate in hexanes) to give the sub-title compound as a white solid (2.3 g, 71%). $^1$H NMR (CDCl$_3$) δ 7.77 (d, J=7.5 Hz, 2H), 7.60 (d, J=6.9 Hz, 2H), 7.41 (t, J=7.5 Hz, 2H), 7.30 (t, J=7.5 Hz, 2H), 6.69 (d, J=7.2 Hz, 1H), 5.27 (d, J=7.8 Hz, 1H), 4.46-4.37 (m, 3H), 4.22 (t, J=7.2 Hz, 2H), 2.62-2.54 (m, 2H), 2.18-2.14 (m, 1H), 1.96-1.91 (m, 1H), 1.45 (d, J=7.5 Hz, 18H), 1.38 (d, J=7.2 Hz, 3H). MS: ESI (positive): 553 (M+H).

b.) 4-tert-Butoxycarbonylamino-4-(1-tert-butoxycarbonyl-ethylcarbamoyl)-butyric acid The product of step a) (2.3 g, 4.16 mmol) was dissolved in DCM (17 ml) and treated with TEA (2.9 ml, 20.8 mmol). The mixture was stirred at room temperature for 16 h. The mixture was diluted with DCM and washed with 1M HCl (2×). The organic layer was dried with magnesium sulfate and the solvent removed in vacuo. The crude product with slurried with ether and filtered to isolate the title compound as a white solid (0.72 g, 46%). $^1$H NMR (CDCl$_3$) δ 6.95 (d, J=9.2 Hz, 1H), 5.40 (d, J=7.5 Hz, 1H), 4.42 (t, J=6.6 Hz, 1H), 4.30 (d, J=6.6 Hz, 1H), 2.52 (m, 2H), 2.12 (m, 1H), 1.93 (m, 1H), 1.45 (d, J=9.2 Hz, 18H), 1.38 (d, J=7.2 Hz, 3H). MS: ESI (positive): 397 (M+Na).

Example 20

2-Amino-6-(1,2-dihydroxy-propyl)-4-oxo-4,6,7,8-tetrahydro-1H-pteridine-5-carboxylic acid benzyl ester

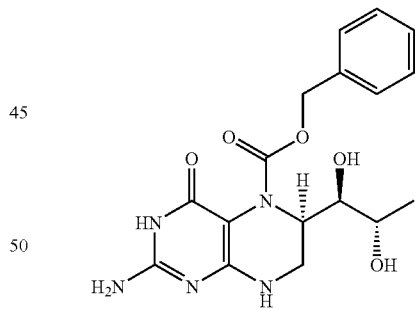

2-Amino-6-(1,2-dihydroxy-propyl)-5,6,7,8-tetrahydro-1H-pteridin-4-one dihydrochloride (1.63 g, 5.2 mmol) was dissolved in 50 mL of pyridine under a nitrogen atmosphere. To this solution was added benzyl chloroformate (1.93 ml, 13.5 mmol). The reaction mixture was degassed under vacuum and placed under an atmosphere of nitrogen. The mixture was stirred for 12 h at room temperature. The solvent was evaporated in vacuo and the residue purified by preparative RP-HPLC to give the sub-titled compound as a white solid (0.93 g, 48% yield). $^1$H NMR (DMSO-d$_6$) δ 10.02 (s, 1H), 7.41-7.30 (m, 5H), 6.84 (s, 1H), 6.12 (s, 2H), 5.10-4.99 (m, 2H), 3.93 (d, J=6.0 Hz, 1H), 3.66 (dd, J=2.4 Hz, J=6.3 Hz, 1H), 3.56 (dd, J=4.8 Hz, J=12 Hz, 1H), 3.25 (d, J=10.5 Hz, 1H), 3.03 (dd, J=4.5 Hz, J=12.4 Hz, 1H), 1.26 (d, J=6.3 Hz, 1H). MS: ESI (positive): 376 (M+H).

Plasma Stability Studies in Human, Rat, and Simulated Gastric Fluid

Figure 3:
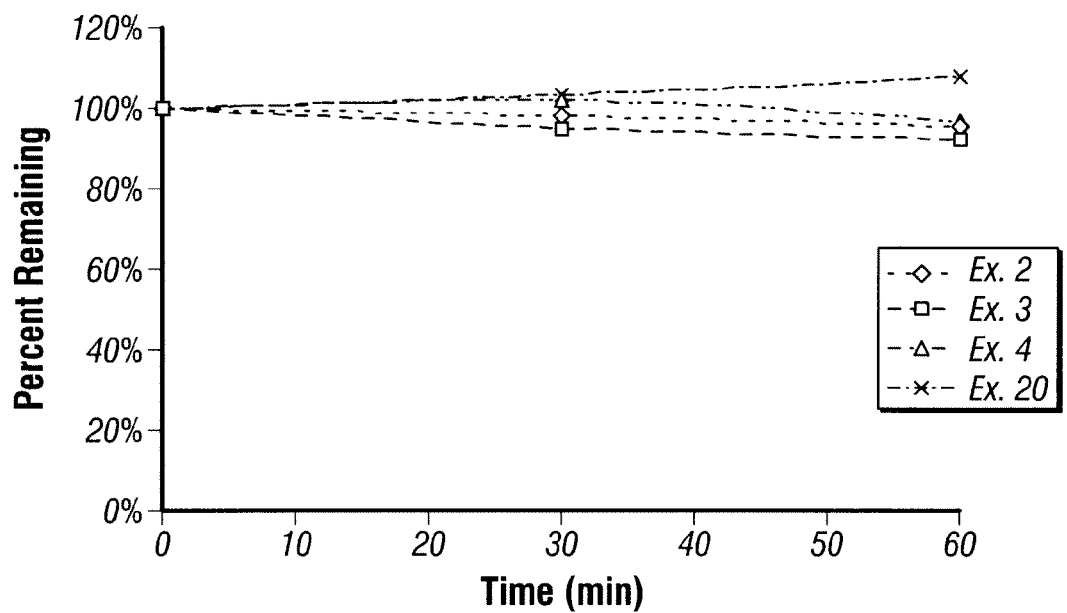
FIG. 3 shows the stability of compounds of Examples 2, 3, 4, and 20 in human plasma over a 60 minute period.
Figure 4:
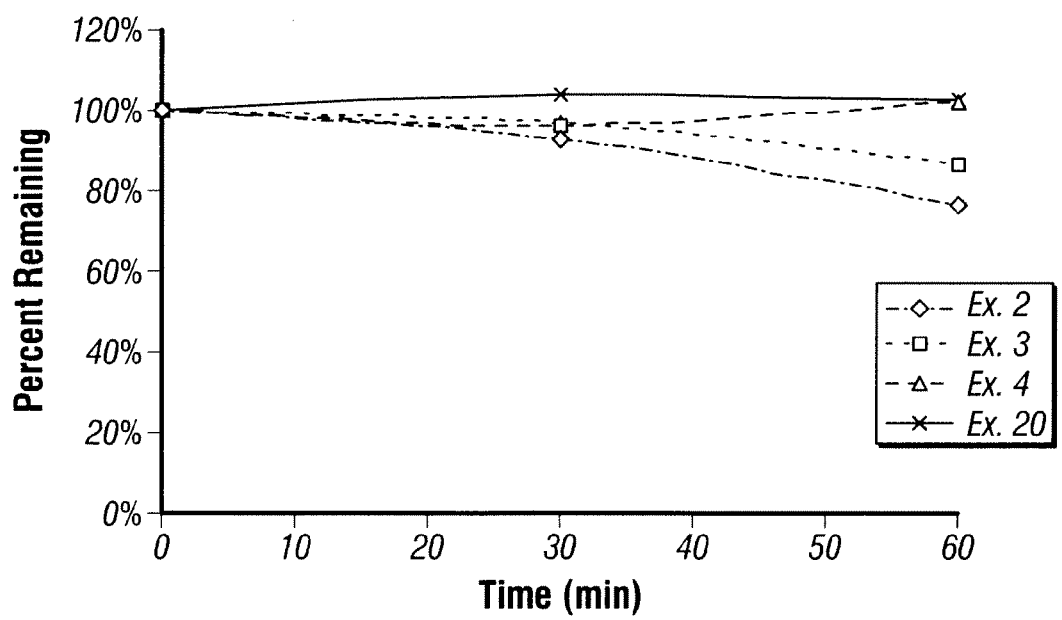
FIG. 4 shows the stability of compounds of Examples 2, 3, 4, and 20 in rat plasma over a 60 minute period.
Figure 5:
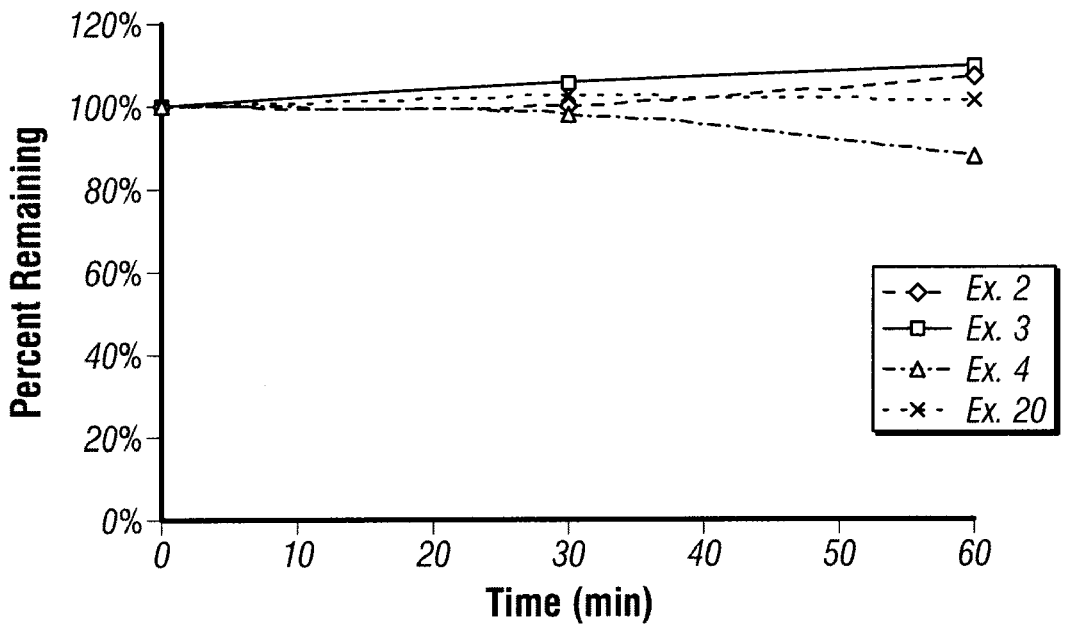
FIG. 5 shows the stability of compounds of Examples 2, 3, 4, and 20 in simulated gastric fluid over a 60 minute period.

The stability of various compounds as disclosed herein was tested in human and rat and in simulated gastric fluid. Each compound was tested over an hour period for concentration of the compound remaining at each time point. The results are shown in FIGS. 3 (human plasma stability), 4 (rat plasma stability), and 5 (simulated gastric fluid stability) for the compounds of Example 2, 3, 4, and 20. As seen in FIGS. 3-5, each of the compounds tested all showed a high level of stability under the various conditions.

Metabolic Study of BH4 Analogs

This example describes an assay for metabolic stability and allows comparison of the stability of an analog of BH4 versus that of BH4.

Test compounds (10 uM) are incubated with mouse, rat and human liver microsomes (protein concentration of 0.5 mg/mL) and 1 mM NADPH in phosphate buffer at 37° C. Experiments are conducted in triplicate. The incubations are initiated by the addition of the microsomes and quenched by the addition of an equal volume of methanol. Samples are taken at two to three timepoints (typically at time zero, 30 minutes, 60 minutes) for analysis. The appropriate positive and negative control incubations are performed. The quantitation of the disappearance of the test compound or % turnover of the test article is determined utilizing LC-MS/MS.

Solubility of BH4 Analogs

This example describes an assay for solubility and allows comparison of the solubility of an analog of BH4 versus that of BH4. The test articles are dissolved in DMSO and serially diluted in phosphate buffered saline pH 7.4 (PBS) in a 96-well plate. The diluted compounds have a final concentration range of 1 to 1000 mg/mL and contain ≦1% DMSO. After a 30-minute incubation at room temperature, precipitation is measured by detecting light scattering on a Lab Systems nephelometer. Solubility is determined by comparing the NU (nephelometer units) of four replicates of a sample concentration to the NU of the solvent blank wells. Insolubility is defined as the concentration at which the blank corrected NU is significantly greater than the solvent blank. A 1% difference calculated by Student's T Test is considered to be significant.

Permeability of BH4 Analogs

This example describes the permeability screen using Caco-2 cell monolayers and allows comparison of the permeability of an analog of BH4 versus that of BH4. Monolayer cultures of Caco-2 cells, suitable for investigation of compound permeability, are grown on either 24- or 96-well polycarbonate membrane inserts for 21 to 30 days. The monolayers are maintained at 37° C. in a 5% $CO_2$ atmosphere at 95% relative humidity until confluent. The maturity and membrane integrity of the monolayers are confirmed by measurement of the trans-epithelial electrical resistance (TEER) or the apparent permeability of the fluorescent marker compound lucifer yellow.

Apparent permeabilities of a series of test and selected marker compounds are determined in duplicate at a single concentration of 10 mM in the apical to basolateral direction. The transport investigations are initiated by the addition of the test compound to the apical compartment and the plates are maintained under culture conditions during the course of the experiment. The basolateral compartments following 30 and 60 minutes of exposure and the final apical compartments are collected and analyzed for test compound content by LC-MS/MS. The recovery and apparent permeability of each test compound are calculated from these data. Appropriate controls are included to characterize the monolayers. The transport experiment from the basolateral to the apical side will also be performed in the presence and absence of a P-gp inhibitor such as verapamil.

Bioavailability of BH4 Analogs

This example describes a study of the bioavailability/pharmacokinetics profile as performed with an analog of BH4 and BH4. The purpose of pharmacokinetic studies is to provide information on systemic exposure of a drug and any metabolites. This data can be used to explain pharmacological or toxicological issues and can also aid in the design of toxicokinetic studies. Pharmacokinetic parameters, such as AUC, half-life, clearance and volume of distribution, are also determined.

The purpose of the study is to evaluate the potential oral availability of the analog compounds, estimate the pharmacokinetic parameters via statistical approximation, and compare such values to those obtained with unaltered BH4. A simple, non-GLP extraction and LC-MS/MS analytical method is developed for plasma analysis. The formula and structural information of the test compounds are reviewed and plasma stability is presumed. If the test compound is unstable in the plasma, methods are modified as necessary. The study involves three healthy rats of either sex per test compound. Dose formulations are prepared by solution or suspension of the test compounds in water, saline, Tween, PEG, or similar vehicle. For each test compound, three rats are dosed at one time via oral gavage and blood collected at four timepoints (1, 2, 4, 8 hours). Concentrations of drug in plasma are measured using LC-UV or LC-MS (/MS) to define plasma concentration-time curve. Pharmacokinetic parameters such as Cmax, Tmax, and Area Under the Curve (AUC) are estimated using WinNonlin (Pharsight Corp.).

If mice are used instead of rats, 12 mice are used for each test compound. Samples are taken from three mice per timepoint, and pharmacokinetics are estimated using mean plasma concentration data per timepoint.

Using in vitro metabolism data, concentrations of major metabolites can also be estimated. Collecting excreta during the in vivo study period and analysis of these samples for parent and metabolites gives an estimate of elimination.

Calculations for % Bioavailability are performed using the following equations:

% Bioavailability of BH4=AUC of BH4 (oral)/AUC of BH4 (IV)×Dose of BH4 (IV)/Dose of BH4 (oral)

% Bioavailability of BH4 analog=AUC of BH4 analog (oral)/AUC of BH4 (IV)×Dose of BH4 (IV)/Dose of BH4 analog (oral)

Hydrolysis of BH4 Analogs

This example describes an assay to determine whether hydrolysis of BH4 analogs (e.g., Compound I) occurs in vivo, whether desired products (including BH4) are formed, and whether the kinetics of hydrolysis are reasonable.

A test compound, e.g., a diester of BH4, (50 uM) is dissolved in a buffer (pH 6.8, 20 mM NaPhos, 150 mM NaCl) and diluted to a total volume of 2 mL. Esterase (0.1 units, Sigma-Aldrich, Carboxyl esterase E.C. 3.1.1.1) is added. At 5-minute time points, 50 ul samples are withdrawn from the reaction solution and extracted with an equal volume of chloroform. After 12 chloroform samples are collected, each sample is injected separately into an HPLC with a standard C4 column using a standard acetonitrile/water/trifluoroacetic acid gradient. The production of the acid used for esterification is calculated by comparison with a pure standard curve of the acid used for esterification, allowing the calculation of the acid used for esterification as a function of time. The slope of this line is the reaction rate. Alternatively, the aqueous phase is assayed using a reverse-phase HPLC method on a C18 column to detect free BH4. Given the oxidation propensities of BH4, this may be an appropriate alternative since detection of the acid used for esterification would occur regardless of the state of the BH4.

The hydrolysis of esterified forms of BH4 spiked into blood or tissue samples obtained from humans or animals depends on endogenous esterases from the tissues and will not use commercially obtained esterases. This method helps determine the probability of the ester hydrolysis in the desired location in vivo. The solvent extraction of reaction products followed by HPLC analysis is required.

Serum samples are taken from humans or animals, and the pH is controlled by diluting the serum with 0.5 M sodium phosphate, pH 6.8, to a total of 20 uM. Diesterified BH4 (50 uM) is dissolved in pH controlled serum and esterase (0.1 units) is added. At 5 minute time points, 50 ul samples are withdrawn from the reaction solution and extracted with an equal volume of chloroform. The chloroform phase is collected for the acid used for esterification analysis and/or aqueous phase for BH4 analysis. After 12 samples are collected, each sample is injected into an HPLC with a standard C4 column using an acetonitrile/water/trifluoroacetic acid gradient for butanoic acid analysis, or a C18 column for BH4 analysis. The production of the acid used for esterification or BH4 is calculated by comparison with a pure standard, allowing the calculation of the acid used for esterification or BH4 as a function of time. The slope of this line is the reaction rate.

Calculations for % conversion of BH4 analogs are done using the following equations:

% BH4 analog of BH4, BH2, and B of total biopterins=(Total biopterins−(BH4+BH2+B)/total biopterins)*100%

BH4 analog of BH4, BH2, and B of dose=(Total biopterins−(BH4+BH2+B)/dose)*100%

BH4 analog of dose=% BH4 analog/Dose

The calculations can be determined using analyte sample concentrations or AUC values.

Pharmacokinetics of BH4 Analogs Administered to Rats

This example allows for comparison of the pharmacokinetics of the analog (Compound I) versus that of BH4 following single oral administration in rats.

Single doses of BH4 (10 and 100 mg/kg) were administered orally to a first group of male Sprague Dawley rats (6 weeks old) under fasting conditions. Single doses of Compound I were administered orally to a first group of male Sprague Dawley rats (6 weeks old) under fasting conditions.

With respect to the administered BH4, the maximum total biopterin concentrations in plasma 2 hrs and 1 hr post-dosing were 108 ng/ml (i.e., about 3 fold the endogenous level) and 1227 ng/ml (i.e., about 30 fold the endogenous level), respectively. Thereafter, biopterin had an elimination half-life ($t_{1/2}$) of about 1.1 hr, returning to the endogenous level 9 hrs post-dosing for the 10 mg/kg dose and 24 hrs post-dosing for the 100 mg/kg dose. The bioavailability (F) after a 10 and 100 mg/kg oral administration were 6.8% and 11.8%, respectively, based on the area under the plasma concentration-time curve (AUC) obtained by subtracting the endogenous level during a 10 mg/kg intravenous administration. The ratio of reduced biopterin to total biopterins in plasma (i.e., the reduced-form ratio) was relatively static (73%-96%).

The analog of BH4 was similarly tested and evaluated. The AUC and the peak (Cmax) is about 50% better than that of BH4, due to its increased bioavailability. The bioavailability is at least 15, 20, or 30% or above, and up to 500% above that of BH4, depending upon the analog.

Pharmacokinetics of BH4 Analogs Administered to Monkeys

Figure 6:
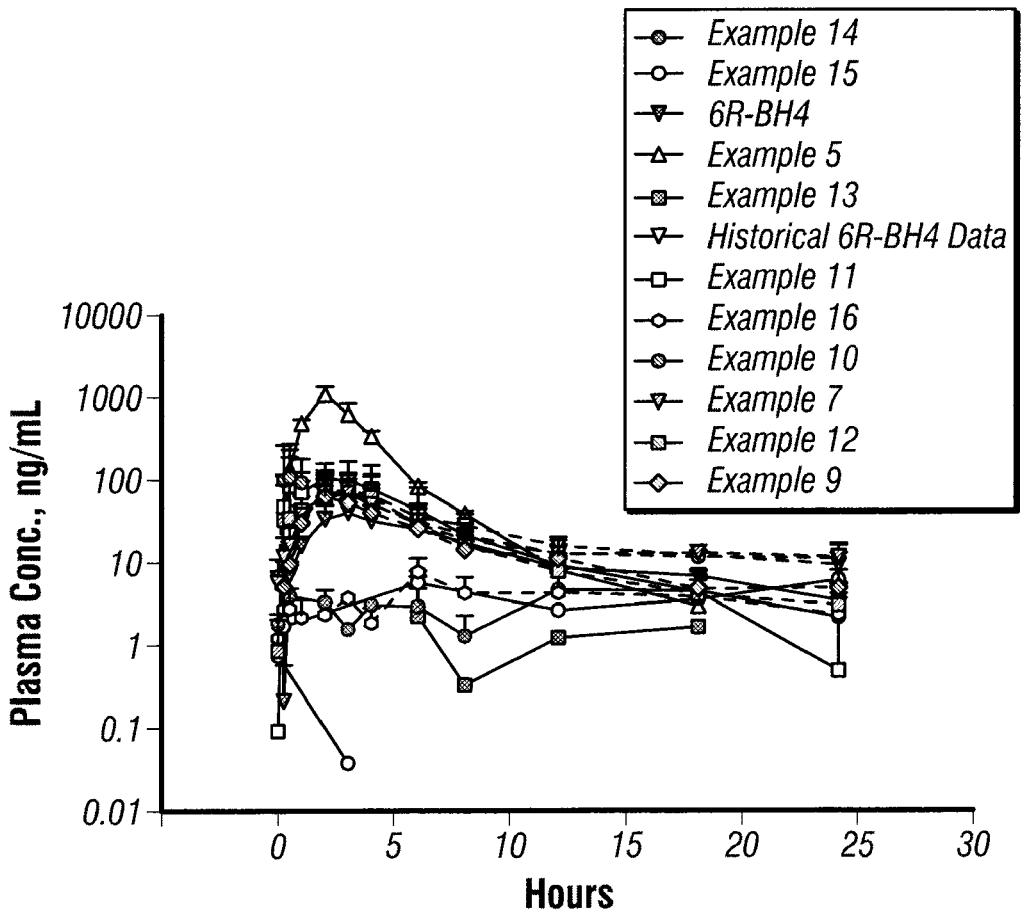
FIG. 6 shows BH4 plasma levels over a 25 hour time period after oral administration of various BH4 analogs to fasted monkeys, compared with BH4.
Figure 7:
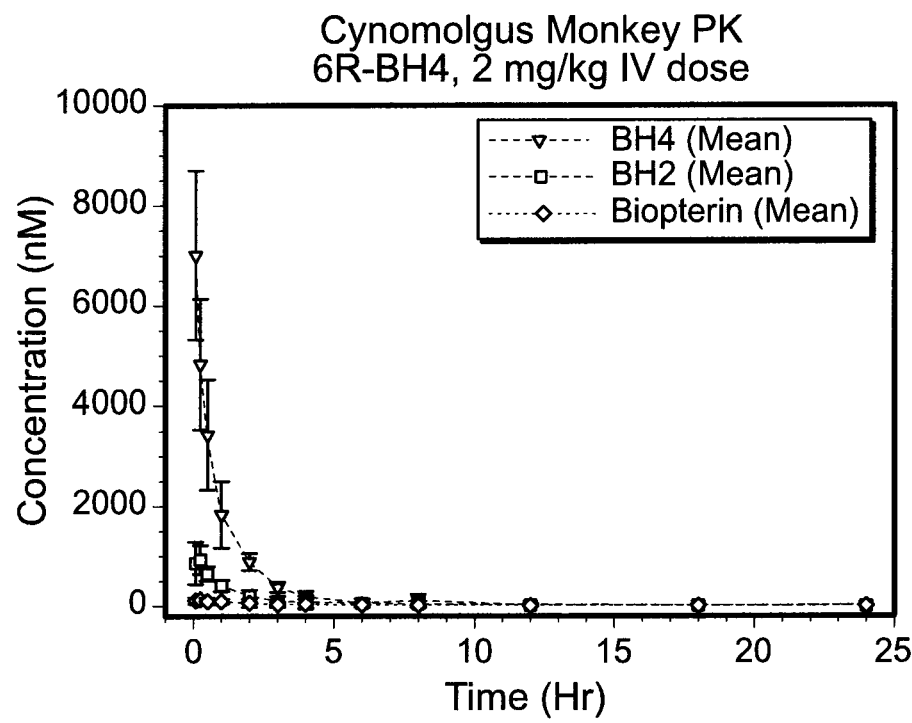
FIG. 7 shows the pharmacokinetics of BH4, BH2 and biopterin after an intravenous administration of BH4 (2 mg/kg) in Cynomolgus monkeys.

Fasted cynomolgus monkeys were given BH4 and BH4 analogs by oral gavage (n=3), such that the amount of the analog administered was the equivalent of 80 mg of BH4. The plasma concentrations of the BH4, when administered directly, or the analogs was measured at various time points over a 25 hour period. The resulting PK data is shown in FIG. 6. The PK data is also shown in the following table, wherein the number in parenthesis is the standard deviation.

TABLE

Pharamacokinetics and Relative Bioavailability of the BH4 Analogs to 6R-BH4[a]

| Compound | $AUC_{0-t}$ (ng*hr/mL) | $C_{max}$ (ng/mL) | $T_{max}$ (hr) | Relative Bioavailability to 6R-BH4 |
|---|---|---|---|---|
| BH4 | 288 (15.5) | 42.0 (12.6) | 3.0 (0) | na[b] |
| Ex. 5 | 2669 (552) | 1016 (228) | 2 (0) | 9.3 (2.1) |
| Ex. 7 | 572 (148) | 82.3 (27.2) | 2.7 (0.6) | 2.0 (0.5) |
| Ex. 9 | 384 (214) | 61.9 (34.8) | 2.0 (0) | 1.3 (0.7) |
| Ex. 10 | 625 (294) | 138 (123) | 1.8 (1.3) | 2.1 (0.9) |
| Ex. 11 | 617 (336) | 115 (65.4) | 1.5 (0.09) | 2.1 (1.0) |
| Ex. 12 | 438 (211) | 73.6 (42.9) | 3.0 (1.0) | 1.5 (0.7) |
| Ex. 13[c] | 13.7 | 2.2 | 6.0 | 0.045 |
| Ex. 14 | 63.2 (25.6) | 5.2 (2.1) | 12.1 (11.9) | 0.22 (0.10) |
| Ex. 15 | 36.8 (37.6) | 5.7 (1.7) | 12.0 (10.4) | 0.13 (0.14) |
| Ex. 16 | 88.1 (31.5) | 7.6 (2.7) | 6.0 (0) | 0.31 (0.12) |

[a]Measured as total biopterin
[b]Not applicable.
[c]n = 2

The previous study showed increased bioavailability of BH4 following administration of BH4 analogs compared to administration of 6R-BH4, especially with the compound of Example 5 based on total biopterin. This study was to determine the pharmacokinetics and relative bioavailability of BH4 when given as parent BH4 or an analog of BH4 to male cynomolgus monkeys as single intravenous or oral doses in a partial Latin square crossover design.

Six, male, non-naïve cynomolgus monkeys were fasted overnight prior to dosing through approximately 4 hours post-dose. Individual doses were calculated based on body weights recorded on each day of dose administration. Five experimental groups of monkeys were evaluated using a partial Latin square crossover design: Group 1-2 mg/kg BH4 by IV; Group 2-40 mg/kg BH4 by oral gavage; Group 3-2 mg/kg BH4 analog by IV; Group 4-5 mg/kg BH4 analog by oral gavage; Group 5-20 mg/kg BH4 analog by oral gavage. The doses of BH4 analog were prepared as mg/kg equivalents of BH4 (calculated using BH4 and BH4 analog 2HCl molecular weights). The partial Latin square crossover design was used to minimize dose sequence effect on interanimal variability for statistical purposes. The monkeys received their respective dose of BH4 intravenously (2 mL/kg, dissolved in 100 µM ascorbic acid and 5% mannitol in sterile water for injection, SWFI), Example 5 intravenously (2 mL/kg, dissolved in 100 µM ascorbic acid and 5% mannitol in citrate buffer, pH 3) or BH4 or Example 5 by oral gavage (4 mL/kg, dissolved in 100 µM ascorbic acid in SWFI). Prior to use, all intravenous dose formulations were filtered into the final dosing container using a 0.22-micron syringe filter (Millex GS or GV; Millipore).

For intravenous administration, blood (approximately 1 mL) was collected from each animal predose and at 0.083, 0.25, 0.5, 1, 2, 3, 4, 6, 8, 12, 18, and 24 hours postdose. For oral administration, blood (approximately 1 mL) was collected from each animal predose and at 0.25, 0.5, 1, 2, 3, 4, 6, 8, 12, 18, and 24 hours postdose. Blood was collected into tubes containing K2-EDTA anticoagulant, which was maintained in chilled condition, and centrifuged to obtain plasma. Centrifugation began within 30 minutes of collection. Three, 100-µL aliquots of each plasma sample were promptly transferred following centrifugation into individual tubes containing 0.1% (w/v) dithioerythritol (DTE) for storage. Once the plasma aliquot was added, each tube was vortexed briefly to mix then immediately placed on dry ice.

The resulting PK data is shown in the following tables, wherein the number in parenthesis is the standard deviation. The PK data is also shown in FIGS. 7-15.

TABLE

Oral Bioavailability of 6R-BH4 and the BH4 analog (compound of Example 5) based on 6R-BH4 IV in Cynomolgus Monkeys[a]

| Drug | Dose, mg/kg[b] | Total Biopterin | | BH4 | |
|---|---|---|---|---|---|
| | | Absolute Bioavailability (%) | Relative Bioavailability to 6R-BH4 | Absolute Bioavailability (%) | Relative Bioavailability to 6R-BH4 |
| 6R-BH4 | 40 | 8.2 (4.4) | na[c] | 9.2 (4.2) | na |
| VAL-BH4 | 5 | 40.7 (8.2) | 5.7 (2.0) | 19.6 (8.8) | 2.3 (0.8) |
| VAL-BH4 | 20 | 25.6 (5.3) | 3.6 (1.6) | 13.7 (4.4) | 1.7 (0.6) |

[a]n = 6
[b]The doses of BH4 analog were prepared as mg/kg equivalents of BH4 (calculated using BH4 and BH4 analog 2HCl molecular weights).
[c]Not applicable.

The absolute bioavailability of 6R-BH4, Val-BH4 at 5 mg/kg and Val-BH4 at 20 mg/kg based on total biopterin measurements in monkey plasma was 8.2, 40.7 and 25.6%; bioavailability relative to 6R-BH4 was 5.7 and 3.6. Based on BH4 measurements, absolute bioavailability was 9.8, 19.7 and 14.0%, respectively; relative bioavailability was 2.3 and 1.7. The total biopterin measurements might include Val-BH4, Val-BH2, Val-B, BH4, BH2 and B.

TABLE

% BH4 Analog (compound of Example 5, Val-BH4) Remaining in Systemic Circulation after Oral Administration in Cynomolgus Monkeys[a]

| Dose[b] (mg/kg) | Val-BH4/BH4 (%) | Val-BH4/ (BH4 + BH2 + B) (%) | Val-BH4/total biopterin[c] (%) |
|---|---|---|---|
| 5 mg/kg | 56.3 (25.2) | 36.4 (16.0) | 23.5 (5.6) |
| 20 mg/kg | 81.0 (18.1) | 51.6 (11.6) | 40.7 (11.1) |

[a]n = 6, Determined from AUC$_{0-t}$
[b]The doses of BH4 analog (compound of Example 5) were prepared as mg/kg equivalents of BH4 (calculated using BH4 and BH4 analog 2HCl molecular weights).
[c]Total biopterin was adjusted to BH4 analog

TABLE

Absolute Bioavailability of the BH4 Analog (compound of Example 5) in Cynomolgus Monkeys[a]

| Dose, mg/kg[b] | Absolute Bioavailability (%) |
|---|---|
| 5 | 36.2 (26.3) |
| 20 | 33.2 (29.2) |

[a]n = 6
[b]The doses of BH4 analog were prepared as mg/kg equivalents of BH4 (calculated using BH4 and BH4 analog 2HCl molecular weights).

The percent of Val-BH4 remaining in systemic circulation after oral administration of Val-BH4 at 5 and 20 mg/kg was greater than 23.5±5.6% based on total biopterin measurements adjusted to Val-BH4. The absolute bioavailability of oral Val-BH4 at 5 and 20 mg/kg in Cynomolgus monkeys was 36% and 33%, respectively.

TABLE

Pharmacokinetics for 6R-BH4 and the BH4 analog (5 mg/kg) after Intravenous Administration in Cynomolgus Monkeys[a]

| Drug | AUC$_{0-t}$ (nM*hr) | AUC$_{inf}$ (nM*hr) | T$_{max}$ (hr) | C$_{max}$ (nM) | t$^{1/2}$ (hr) | Vz (L/kg) | Vdss (L/kg) | CL (L*hr/kg) |
|---|---|---|---|---|---|---|---|---|
| 6R-BH4 | 6762 (1224) | 6955 (1203) | 0.11 (0.07) | 7053 (1599) | 2.3 (0.8) | 3.1 (1.2) | 2.0 (0.8) | 0.9 (0.1) |
| Val-BH4 | 4166 (3484) | 5241 (4983) | 0.08 (0) | 13055 (10414) | 1.50 (2.07) | 6.35 (8.43) | 3.78 (6.35) | 2.48 (1.76) |

[a]n = 6

TABLE

Pharmacokinetics for 6R-BH4 and BH4 analog (Val-BH4) after Oral Administration in Cynomolgus Monkeys[a]

| Drug | Dose[b] (mg/kg) | $AUC_{0-t}$ (nM*hr) | $AUC_{inf}$ (nM*hr) | $T_{max}$ (hr) | $C_{max}$ (nM) | $t^{1/2}$ (hr) |
|---|---|---|---|---|---|---|
| 6R-BH4 | 40 | 11944 (4602) | 13361 (5353) | 3.7 (1.4) | 2328 (1182) | 5.9 (4.9) |
| Val-BH4 | 5 | 1671 (534) | 1734 (457) | 1.0 (0.5) | 1140 (580) | 5.2 (8.2)[c] |
| Val-BH4 | 20 | 7235 (1956) | 7596 (2386) | 1.2 (0.4) | 2903 (267) | 9.1 (20)[c] |

[a] n = 6
[b] The doses of BH4 analog were prepared as mg/kg equivalents of BH4 (calculated using BH4 and BH4 analog 2HCl molecular weights).
[c] The extreme difference with $t_{1/2}$ may be due to measuring $t_{1/2,\alpha}$ versus $t_{1/2,\beta}$ for the individual animals, but there is not enough data to determine $t_{1/2,\beta}$ in most cases.

The pharmacokinetics for Val-BH4 and 6R-BH4 after IV administration at 2 mg/kg show that mean Cmax was higher for Val-BH4 and mean AUC was greater for 6R-BH4 with a slightly longer $t_{1/2}$. The Cmax may be higher for Val-BH4 due to active transport across the intestinal wall. The AUC maybe lower for Val-BH4 due to faster distribution into the tissues. The pharmacokinetics for Val-BH4 and 6R-BH4 after oral administration indicate a longer time to Cmax and a longer $t_{1/2}$ for 6R-BH4.

The above bioavailability data demonstrates that oral Val-BH4 at 5 mg/kg provided 6-fold systemic exposure of BH4 compared to 6R-BH4 based on total biopterin. Based on BH4, Val-BH4 bioavailability was greater than 2-fold systemic exposure of BH4 compared to 6R-BH4. The data also indicates that high concentrations of Val-BH4 were present in plasma with absolute bioavailability at about 33 to 36%.

Figure 8:
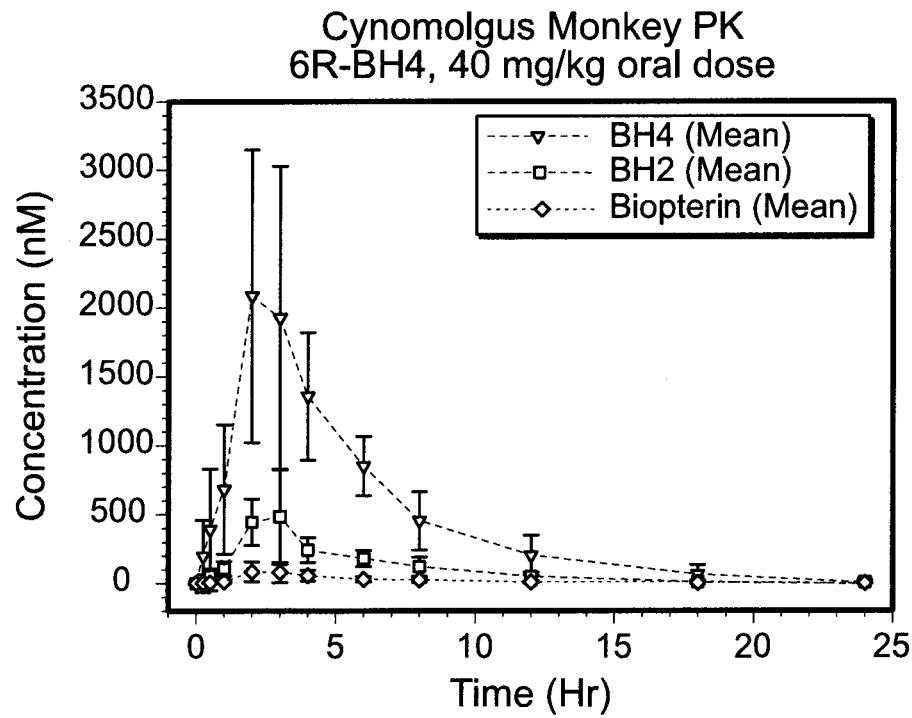
FIG. 8 shows the pharmacokinetics of BH4, BH2 and biopterin after an oral administration of BH4 (40 mg/kg) in Cynomolgus monkeys.
Figure 9:
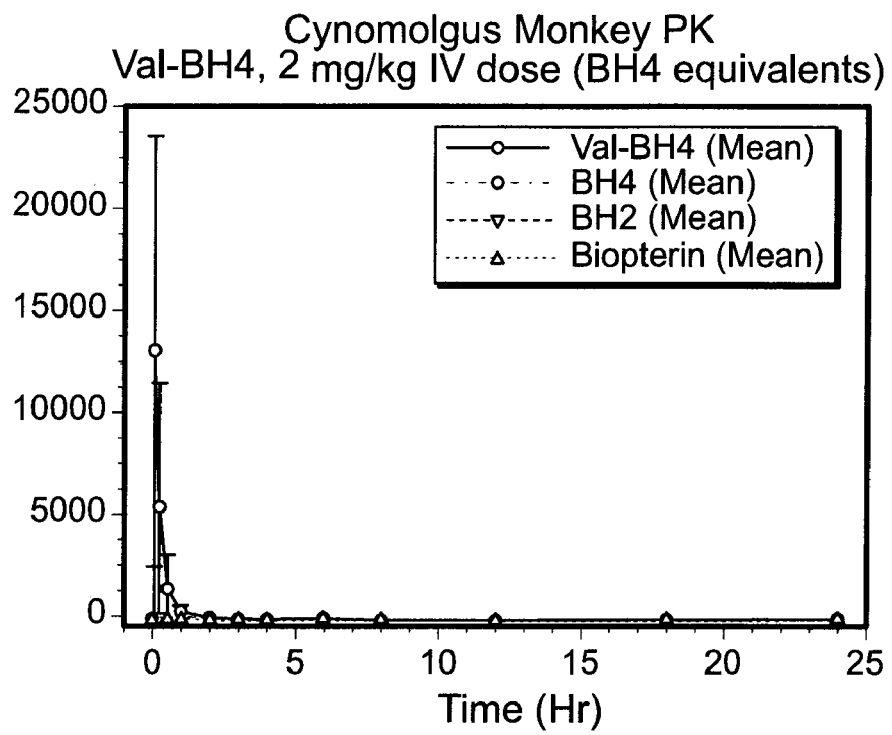
FIG. 9 shows the pharmacokinetics of the compound of Example 5, BH4, BH2 and biopterin after an intravenous administration of the compound of Example 5 (2 mg/kg in BH4 equivalents) in Cynomolgus monkeys.
Figure 10:
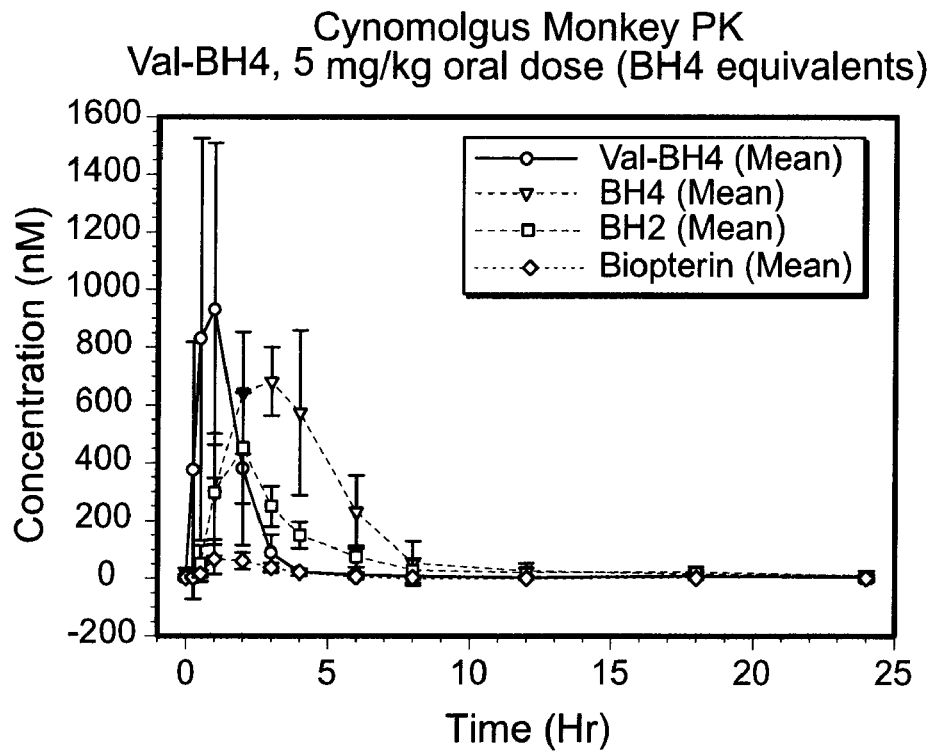
FIG. 10 shows the pharmacokinetics of the compound of Example 5, BH4, BH2 and biopterin after an oral administration of the compound of Example 5 (5 mg/kg in BH4 equivalents) in Cynomolgus monkeys.
Figure 11:
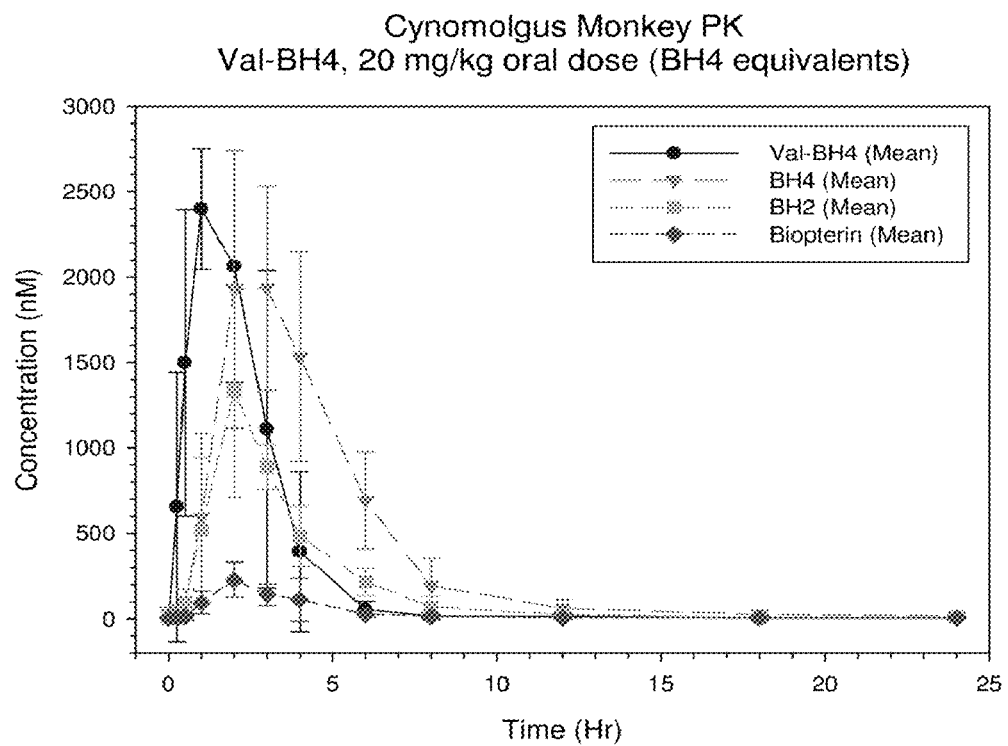
FIG. 11 shows the pharmacokinetics of the compound of Example 5, BH4, BH2 and biopterin after an oral administration of the compound of Example 5 (20 mg/kg in BH4 equivalents) in Cynomolgus monkeys.

FIGS. 7-11 show the PK data in plasma for the five dose conditions: 2 mg/kg BH4 or BH4 analog by IV and 40 mg/kg BH4, 5 mg/kg BH4 analog or 20 mg/kg BH4 analog by oral gavage. After an oral 40 mg/kg dose of BH4, more BH4 was detected than BH2 and biopterin and the Tmax of BH4, BH2 and B were approximately the same (FIG. 8). After an oral 5 mg/kg dose of the BH4 analog (compound of Example 5), the analog was absorbed quickly and was rapidly distributed by 4 hr (FIG. 10). Tmax was later for BH4 than for BH2 and biopterin, which suggests that BH2 may be generated through Val-BH2.

Figure 12:
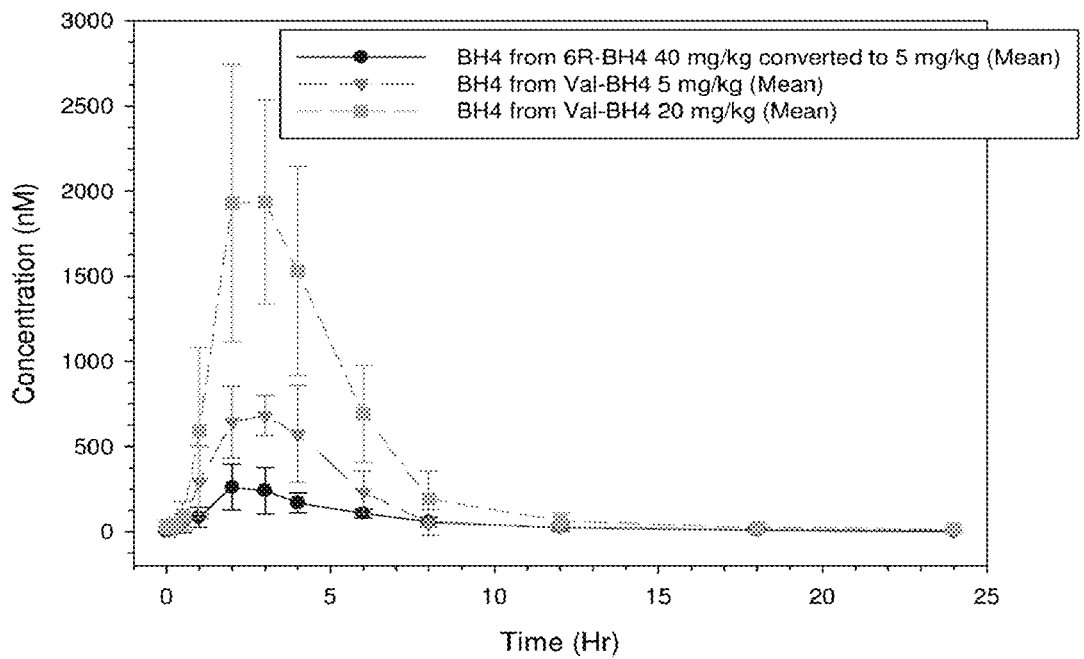
FIG. 12 shows the comparison of BH4 pharmacokinetics after oral administrations of BH4 (40 mg/kg, converted to 5 mg/kg for comparison) or the compound of Example 5 at 5 mg/kg or 20 mg/kg (in BH4 equivalents).

Comparing the oral doses of BH4 (adjusted to 5 mg/kg for comparison) and BH4 analog (5 and 20 mg/kg) with respect to BH4, more BH4 was detected in the plasma after BH4 analog administrations than after BH4 itself (FIG. 12).

Figure 13:
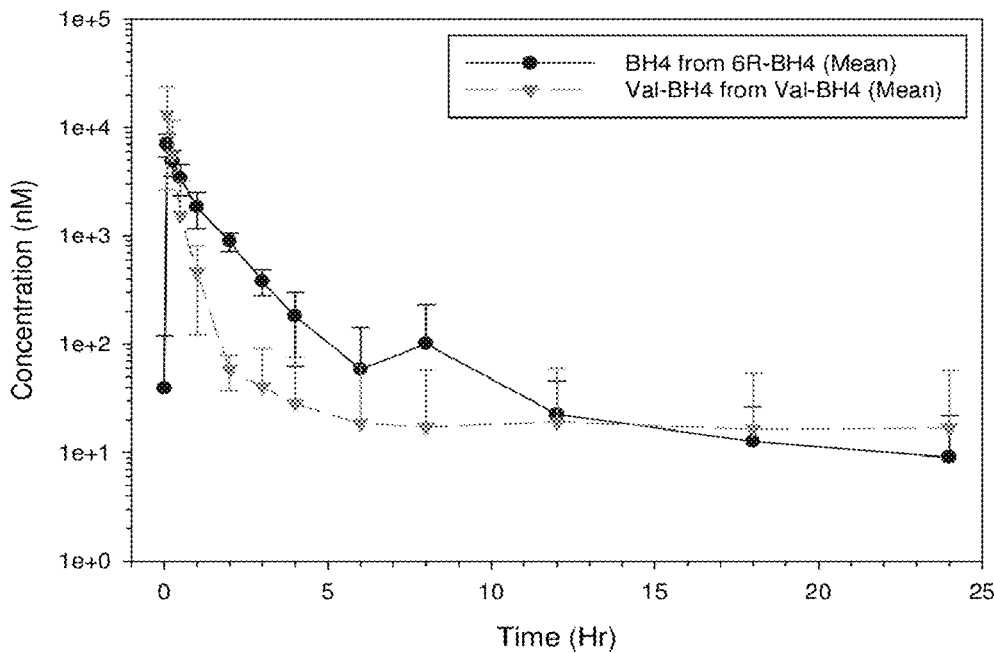
FIG. 13 shows the pharmacokinetics after intravenous administration of BH4 (2 mg/kg) or the compound of Example 5 (2 mg/kg in BH4 equivalents).
Figure 14:
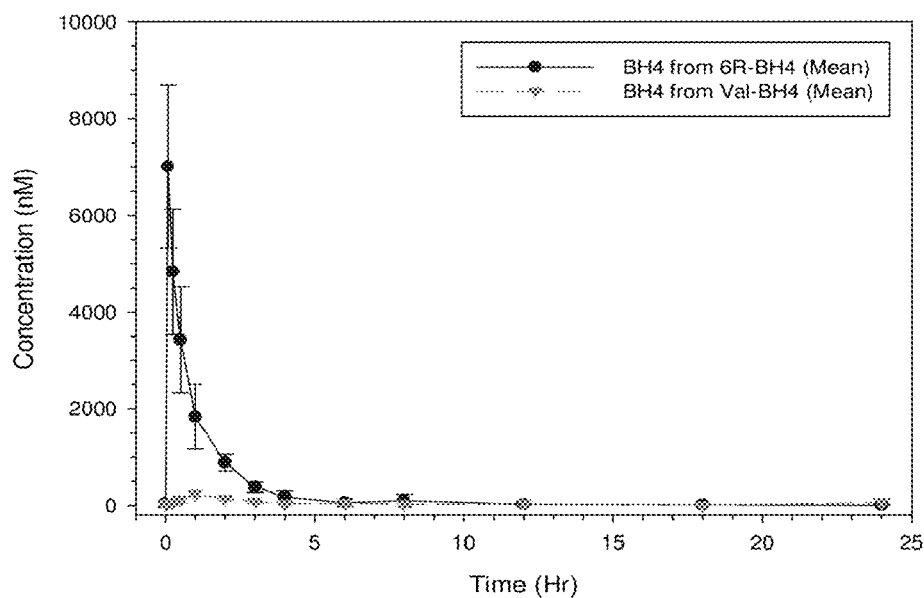
FIG. 14 shows the BH4 pharmacokinetics after intravenous administration of BH4 (2 mg/kg) or the compound of Example 5 (2 mg/kg in BH4 equivalents).
Figure 15:
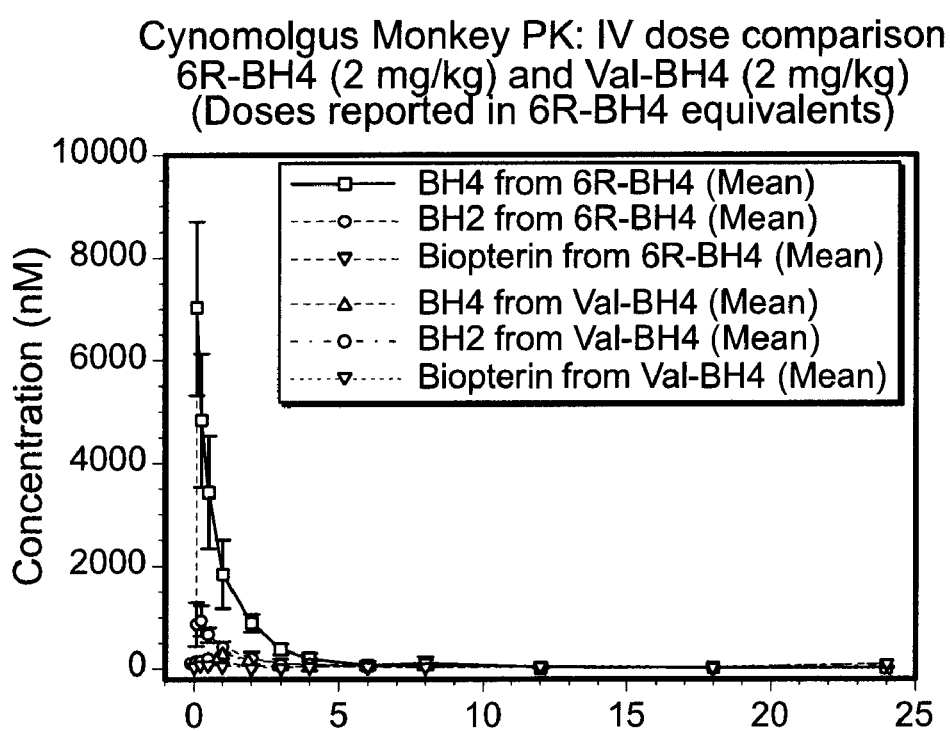
FIG. 15 shows the pharmacokinetics of BH4, BH2 and biopterin after intravenous administration of BH4 (2 mg/kg) or the compound of Example 5 (2 mg/kg in BH4 equivalents).

FIG. 13 shows the comparison of the intravenous doses of BH4 and the BH4 analog (2 mg/kg in BH4 equivalents) in log scale. FIG. 14 compares BH4 after BH4 and BH4 analog intravenous administrations, while FIG. 15 includes BH2 and biopterin also. Interestingly, the concentrations of BH4 along with BH2 and biopterin after intravenous administration of the BH4 analog were very low compared to the concentrations after BH4 administration. This seems to suggest that biotransformation via first pass metabolism is the primary mechanism and blood esterases are not as active.

Without intending to be bound by any particular theory, biotransformation via first pass metabolism is hypothesized to be likely as the primary mechanism. The bioavailability data demonstrates that oral Val-BH4 at 5 mg/kg provided greater than 2-fold systemic exposure of BH4 compared to 6R-BH4 and 6-fold greater systemic exposure based on total biopterin. The data also indicates that high concentrations of Val-BH4 were present in plasma with absolute bioavailability at about 33 to 36%.

Absorption of BH4 Analogs in the Gastrointestinal Tract

Gastrointestinal absorption is evaluated in humans in a blinded cross-over study.

Unless otherwise stated, subjects are given either tetrahydrobiopterin (BH4) or the analog of BH4 at a dose of 1, 5, and 10 mg/kg after a fast of 10 hours. In the fed leg of the study, subjects are administered either BH4 or the analog of BH4. Blood samples are collected in heparinized vials at 0, 0.5, 1, 2, 3, 4, 6, 8, 12, 24, 48, 72, 96, 120, 144 h post dose. For a single dose and relative bioavailability study, plasma samples are also collected 0.25, 0.75 and 1.5 hours after administration and assayed for total biopterin to evaluate the site of gastrointestinal absorption of either BH4 or the BH4 analog.

Subjects are given a 1, 5, and 10 mg/kg oral or intravenous dose of either BH4 or the BH4 analog, followed by serial measurements of plasma total biopterin concentration to determine the rate of BH4 or the BH4 analog absorption from the gastrointestinal tract from the area under the plasma total biopterin concentration increase ($\Delta$Cp)-time curve ($\Delta$AUC). It is anticipated that a lower dose of BH4 will be required when administered intravenously in comparison with BH4 administered orally to achieve the same level of bioavailability. For example, it may require 10 mg/kg of BH4 given orally to achieve the same level of bioavailability as 1 mg/kg BH4 administered intravenously. Because the analog of BH4 serves to enhance bioavailability, it may require only 2.5 mg/kg of the BH4 analog to achieve the same level of bioavailability as a 1 mg/kg IV dose of BH4 to achieve the same percent bioavailability.

The rate of BH4 or BH4 analog absorption from the gastrointestinal tract is estimated from the area under the plasma total biopterin concentration increase ($\Delta$Cp)-time curve ($\Delta$AUC) after the administration of BH4 or BH4 analog using the following formulas:

Absorption rate (%)=($\Delta$AUC after p.o. dose/$\Delta$AUC after i.v. dose)×(i.v. dose/p.o. dose×100)

Some analogs of BH4 may require a longer duration to release the active BH4. Thus, a measurement of free or released BH4 alone in the blood may not accurately reflect the total amount of BH4 that could be available for treatment. Hence, a measurement of the total concentration of the analog and BH4 together is required to accurately or more precisely determine the level of BH4 in the blood for the purposes of evaluating bioavailability and comparing bioavailability of the analog and BH4.

Measurement of Metabolites of BH4

Biopterin assay: The concentration of total biopterin and oxidized biopterin in plasma, blood and other tissues are determined based on the method of Fukishima et al (*Anal. Biochem.* 102:176 (1980)). Biopterin has four different forms including two forms of reduced biopterin, R-tetrahydrobiopterin (BH4) and quinonoid R-dihydrobiopterin (q-BH2) and two forms of oxidized biopterin, dihydrobiopterin (BH2) and biopterin (BP). Of these four forms, only the reduced forms of biopterin have coenzymatic activity. Reduced biopterin is converted to BP by iodylation under acidic conditions, whereas under alkaline conditions, it is converted to pterin. Oxidized biopterin is converted to BP by iodylation under acidic and alkaline conditions. By taking advantage of this property, the amount of total biopterin is determined upon iodylation under acidic conditions and that of oxidized biopterin is determined upon iodylation under alkaline conditions, so that the amount of reduced biopterin is calculated from the difference in quantity thereof. When used as a coenzyme, BH4 is converted to q-BH2. The q-BH2 is immediately converted to BH4 by dihydropterine reductase or if not reduced, it is oxidized to BH2 or DHPT. Because it is difficult for biopterin to exist in the form of q-BH2 in vivo, the reduced biopterin may well be displaced as BH4.

Plasma and whole blood samples collected are immediately subjected to oxidation with acidic oxidizing solution (0.6N HCl solution in water containing 0.6% potassium iodide (KI), 0.3% iodine ($I_2$) and 0.6N trichloroacetic acid (TCA)) and alkaline oxidizing solution (0.7N sodium hydroxide (NaOH)). Determination of BP is performed by HPLC and radioactivity is measured using a liquid scintillation counter.

Measurement of BH4 using Reverse Phase HPLC (RP) Coupled with Tandem Mass Spectrometry (LC/MS/MS): The combined use of reverse phase high performance liquid chromatography (RP) and tandem mass spectrometry (LC/MS/MS) was shown to be selective for BH4 in human plasma, sensitive for BH4 in the range of 5-1000 ng/mL. The method is associated with about 50% conversion of BH4 due to oxidation during collection and storage. Samples are stable for greater than 3 months in dipotassium salt of ethylenediaminetetraacetic acid ($K_2$EDTA) plasma. Recovery from the pre-treatment steps is about 75%. The accuracy and precision of the method was determined to have coefficient of variation (CV) % below 15% (20% at the lower limit of quantitation, LLOQ).

The combined use of HPLC and tandem mass spectrometry was shown to be an improvement over HPLC alone in determining the BH4 test article because of: (1) its increased selectivity for drug-BH4 (whereas HPLC measures total biopterin), (2) broader qualitative range, (3) established conversion ratio, (4) extensive characterization and proven utility in human subjects, and (5) novel and useful measurement in different species and matrices.

The improved method comprises the following steps. Samples of blood, plasma, tissue homogenates, or urine are subjected to acidic or alkaline oxidation. With acidic oxidation, (1) the samples are treated with potassium chloride (KCl), hydrochloric acid (HCl) or TCA for an hour; (2) the acid oxidized samples are then subjected to iodometry; (3) the samples are run through an ion exchange column; (4) total biopterin comprising BH4, q-BH2 (which is immediately reduced in vivo to BH4 such that the measured reduced biopterin is based mainly upon BH4), BH2, and BP are measured using HPLC and tandem mass spectrometry. With alkaline oxidation, (1) the samples are treated with KI, $I_2$ or NaOH for an hour; (2) the alkaline oxidized samples are then subjected to acidification with HCl or TCA; (3) subjected to iodometry; (4) the samples are run through an ion exchange column; (5) oxidized biopterin comprising BH2 and BP are measured; (6) different species are measured using HPLC and tandem mass spectrometry; and (7) the amount of reduced biopterin (BH4+q-BH2) is calculated as the difference between total biopterins less the oxidized form.

The flow chart of biopterin measurement and assay validation summary are provided in FIGS. 1 and 2.

Optimized Assay

An HPLC method using Electrochemical Detection (ECD) and Fluorescence (FL) detection is advantageous as it allows for the measurement of each of the discrete biopterin compounds (BH4, BH2 and B) as well as analog, such as prodrug, forms (e.g., Val-BH4, Val-BH2, and Val-B).

The concentrations of different biopterins (BH4, BH2 and B) and Val-biopterins are determined by initially using reverse phase HPLC for separation, followed by ECD and FL detection. BH4 and Val-BH4 are measured using ECD in which BH4 and Val-BH4 are oxidized by electrode 1 to quinonoid dihydrobiopterin forms (qBH2 or Val-qBH2, respectively), a short-lived dihydrobiopterin intermediate, and then reduced back to BH4 or Val-BH4 at electrode 2. The detector then uses the current generated by this reduction reaction to determine the concentration of BH4 or Val-BH4, respectively. BH2, Val-BH2, B and Val-B are measured by fluorescence detection. Post-column oxidation of BH2 and Val-BH2 using a conditioning guard cell at the optimum potential oxidizes BH2 and Val-BH2 to B and Val-B, respectively. Post-column oxidation is a step wherein the BH2 (and other species) are oxidized to Biopterin (B). This is desirable because BH2 is not fluorescently active or easily measured and must be converted to biopterin, which is easily measured using fluorescence. In total the methods can be used to measure the six species (BH4, BH2, B, Val-BH4, Val-BH2, and Val-B). In one embodiment, the biopterin analogs, such as valine biopterin derivatives, are measured using a 10% MeOH-containing mobile phase whereas the biopterins are measured using a 2% MeOH-containing mobile phase.

Thus, a method for detecting biopterins in a mixture of biopterin species can include (a) separating biopterin species in the mixture by reverse phase HPLC; and in the case of BH4 and analogs thereof, (b1) performing electrochemical detection by oxidizing the BH4 and analogs thereof present by a first electrode to quinonoid dihydrobiopterin forms, followed by reducing the quinonoid forms back to BH4 and analogs thereof present at a second electrode, and measuring current generated by the reduction reaction to determine the concentration of species; and/or (b2) in the case of BH2, analogs thereof, biopterin, or analogs thereof, measuring such species by fluorescence detection following post-column oxidation of BH2 species to biopterin.

Figure 16:
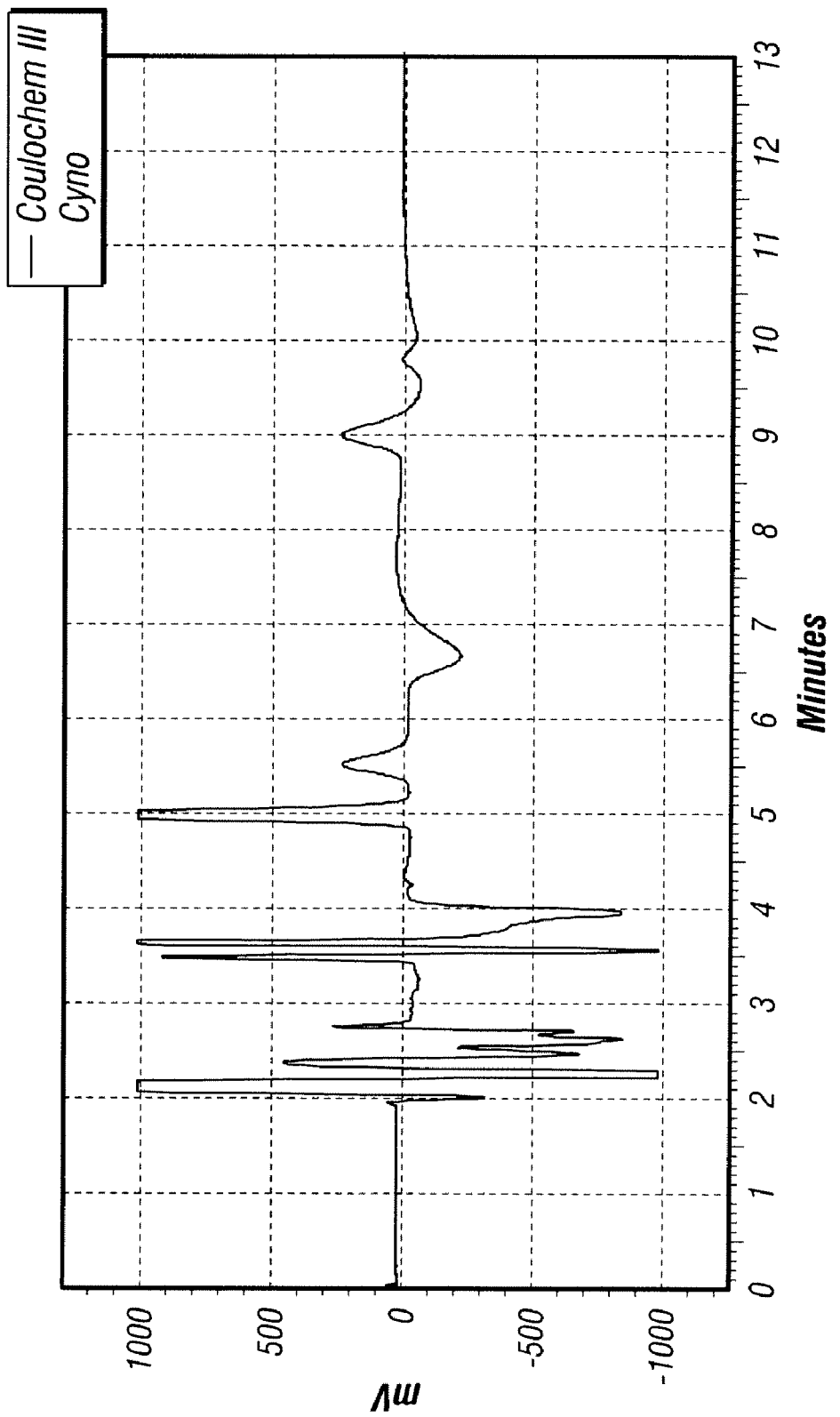
FIG. 16 shows a BH4 chromatogram from plasma of cynomolgus monkeys, 2 hours post-administration of the compound of Example 5 (2% MeOH mobile phase).

The compound of Example 5 can be detected in buffer and by extraction using this assay. Measurement of BH4, BH2, and B using this assay from cynomolgus monkeys dosed with the compound of Example 5 indicates greatly increased bioavailability (see FIG. 16). In FIG. 16, the peak at about 5 minutes is characteristic of BH4, and the height of the peak at 5 minutes is several fold higher than what was observed when monkeys were administered BH4. The height and area of the peak are representative of concentration. The compound of Example 5 from monkeys 2 hours post-dosing was also observed after its administration by using a method with a 10% MeOH-containing mobile phase.

Effect of BH4 Analogs on Nitric Oxide Production

Cultured human umbilical vein endothelial cells (HUVEC) were pretreated with 3 mM N-acetylserotonin (NAS), an inhibitor of the enzyme sepiapterin reductase. Inhibition of this pathway typically results in loss of endogenous BH4, depressing the endogenous eNOS activity far below normal and provides an assay to test for restoration of eNOS activity.

Figure 17:
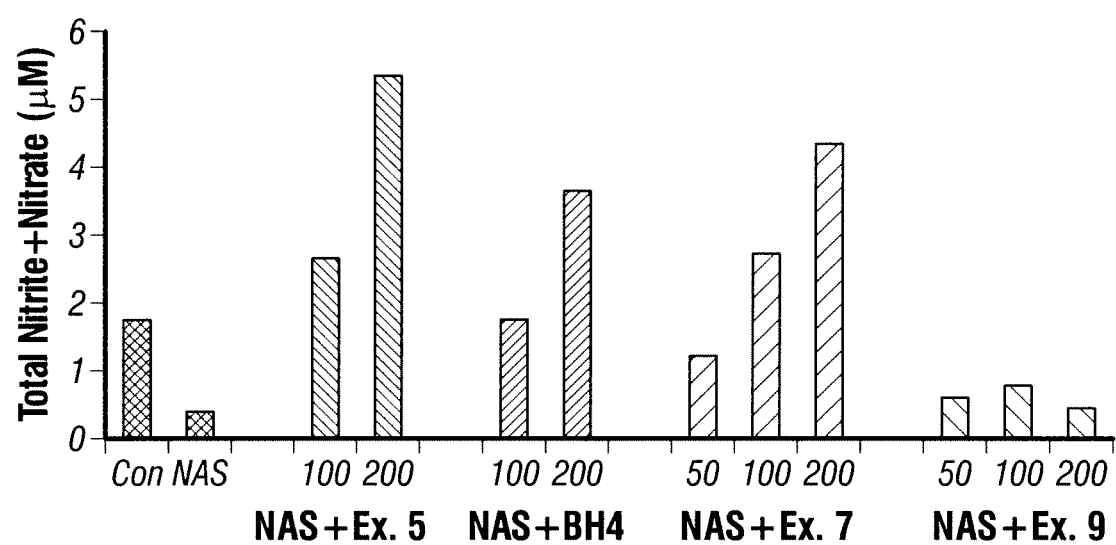
FIG. 17 shows the percentage of nitrite+nitrate increase after 5 hours treatment with BH4 and the compounds of Examples 5, 7, and 9 at various concentrations.
Figure 18:
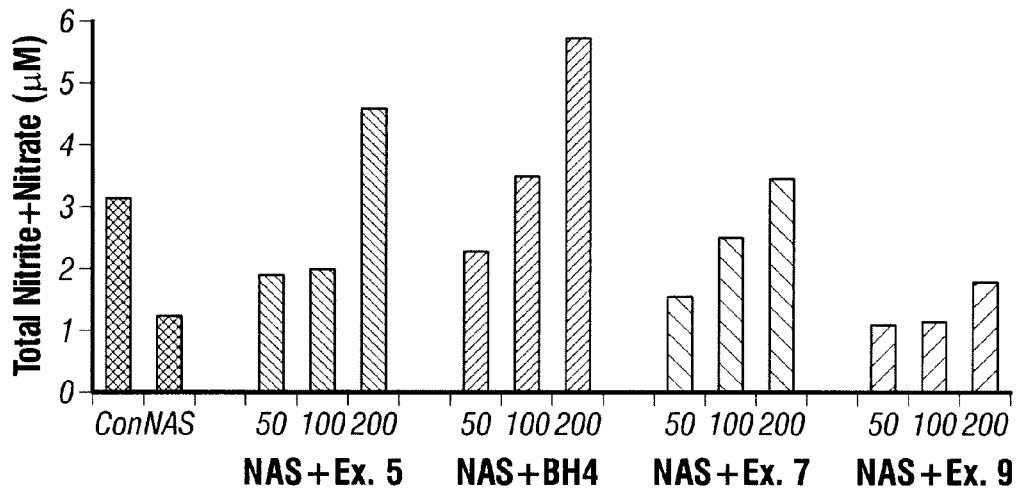
FIG. 18 shows the percentage of nitrite+nitrate increase after 17 hours treatment with BH4 and the compounds of Examples 5, 7, and 9 at various concentrations.
Figure 19:
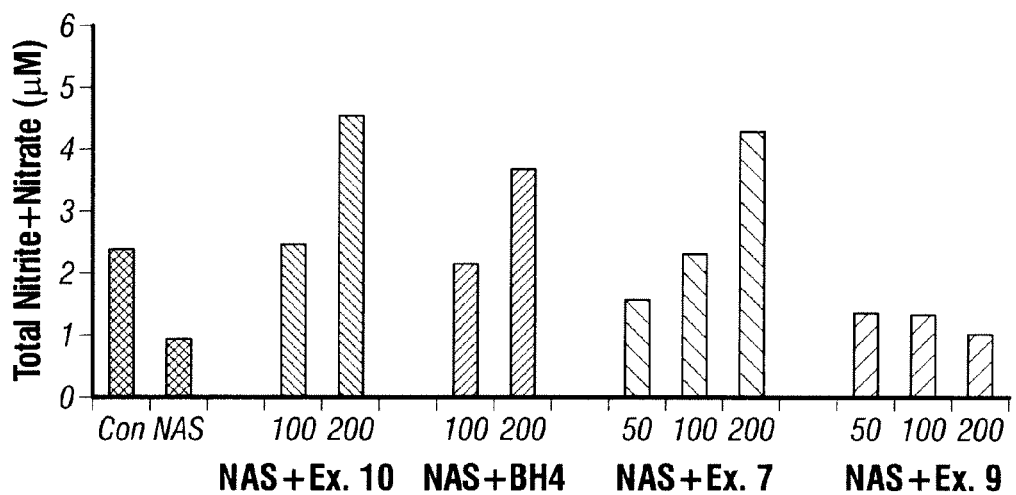
FIG. 19 shows the percentage of nitrite+nitrate increase after 22 hours treatment with BH4 and the compounds of Examples 5, 7, and 9 at various concentrations.
Figure 20:
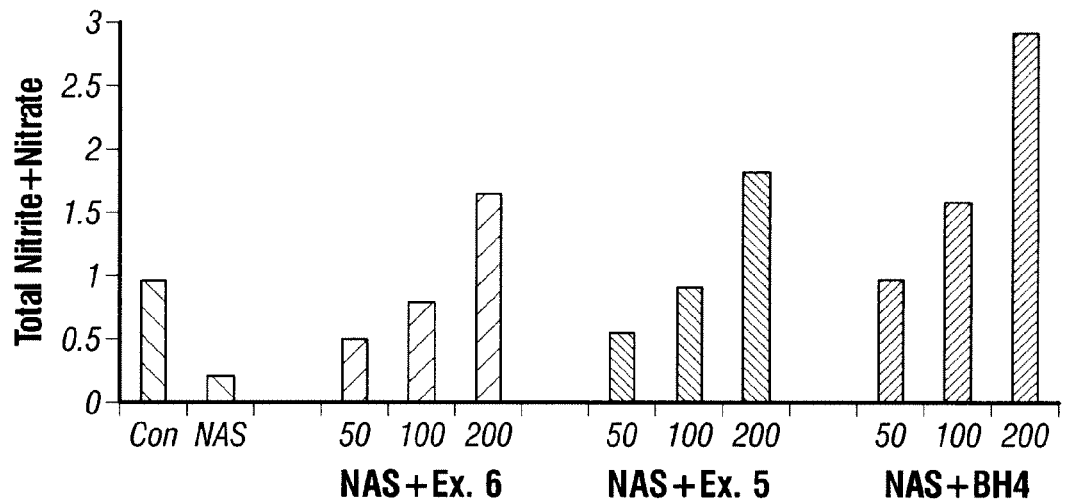
FIG. 20 shows the percentage of nitrite+nitrate increase (as shown by μM concentration) after 5 hours treatment with BH4 and the compounds of Example 5 and 6 at various concentrations.
Figure 21:
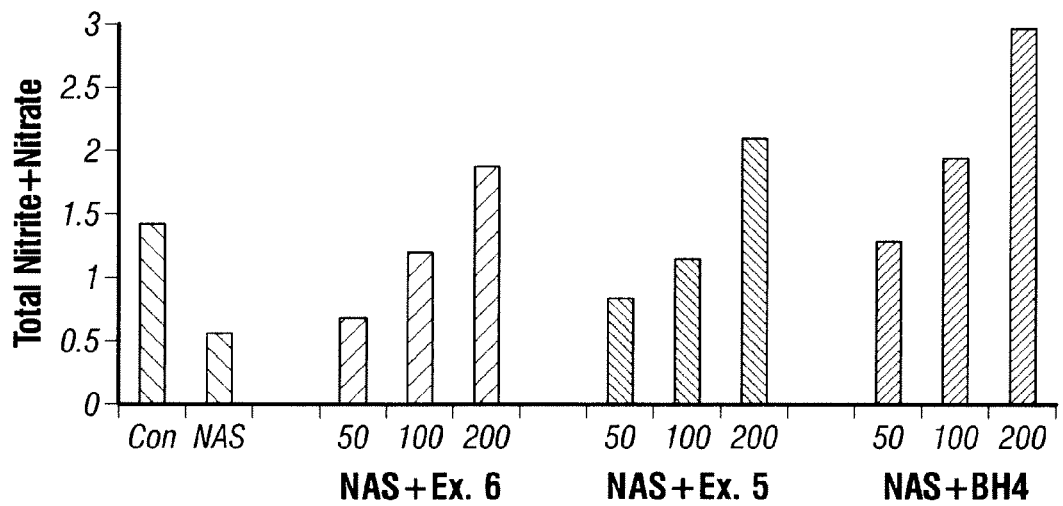
FIG. 21 shows the percentage of nitrite+nitrate increase (as shown by μM concentration) after 20 hours treatment with BH4 and the compounds of Examples 5 and 6 at various concentrations.

Thus, subconfluent HUVECs were seeded in a 24-well plate and grown overnight in EGM2 medium (full growth medium). The next morning, fresh medium was added to the cells (300 µL/well), 3 mM N-acetylserotonin (NAS), an inhibitor of the enzyme sepiapterin reductase (a member of the synthesis pathway for endogenous BH4) was added to the cells to decrease the endogenous BH4 levels. After an incubation of 1.5 hours, 50, 100, or 200 mM BH4 or compound of Example 5, Example 6, Example 7, or Example 9 were added to the cells. The cells were allowed to react with the BH4 or the compound of Example 5, Example 7, or Example 9 for 5-22 hours. The production of NO was then measured as changes in total (nitrite+nitrate) by the Griess reaction subsequent to nitrate reductase treatment. 90 µl of reaction mixture (25 mM Tris-HCL, pH7.4, 1 µM FAD, 1 µM FMN, 100 µM L-Arginine, 2.5 mM $CaCl_2$, 1 mM NADPH, 0.04 mg/ml Calmodulin) was mixed with 5 µl of eNOS (15 units/ml) and 5 µl of BH4 or BH4 analogs (1, 10, 100 µM), followed by incubation in a 37° C. water bath for 90 minutes. Then 100 µl of water and 20 µl of the nitrite fluorescent probe DAN (2,3-diaminonaphthalene, 316 µM) were added to each reaction and incubated at room temperature for 10 minutes. The dye DAN reacts with nitrite to yield the fluorescent product naphthotriazole. The reaction was then stopped by adding 10 µl of NaOH (2.8 M), and the fluorescence of the samples was read using excitation frequency 375 nm and emission frequency 415 nm. The percentage of nitrite+nitrate with BH4 or compound of Example 5, Example 7, or Example 9 is shown in FIG. 17 (after 5 hours); FIG. 18 (after 17 hours); and FIG. 19 (after 22 hours). The results for Example 6 are shown in FIG. 20 (after 5 hours) and FIG. 21 (after 20 hours).

The addition of the compound of Example 5, 6, 7, or 9 to NAS-treated cells increased NO production in a dose-dependent manner. Additionally, treatment of cells with the compound of Example 5 yielded approximately 60%-80% the effect of BH4, suggesting that the analog is de-esterified inside the cells to produce the active BH4. Compounds of Example 6, 7, and 9 had similar, if slightly reduced, effect on the NAS-treated cells.

The compound of Example 5 has the desired in vitro pharmacologic activity (stimulation of nitrite production from endothelial nitric oxide synthase in cultured endothelial cells), and delivers about 60% to 80% of the response given by free BH4 in this cell culture system. Trends were similar after 5 hours or 22 hours exposure; there was a bit more difference between analog and free BH4 after 22 hours. These results suggest that endothelial cells contain esterases that can assist in yielding the active free BH4.

Also tested was the effect of BH4 analogs compared to free BH4 on stimulation of eNOS activity in a cell-free assay system reconstituted from purified components. 90 µl of reaction mixture (25 mM Tris-HCL, pH7.4, 1 µM FAD, 1 µM FMN, 100 µM L-Arginine, 2.5 mM $CaCl_2$, 1 mM NADPH, 0.04 mg/ml Calmodulin) was mixed with 5 µl of eNOS (15 units/ml) and 5 µl of BH4 or BH4 analogs (1, 10, 100 µM), followed by incubation in a 37° C. water bath for 90 minutes. Then 100 µl of water and 20 µl of the nitrite fluorescent probe DAN (2,3-diaminonaphthalene, 316 µM) were added to each reaction and incubated at room temperature for 10 minutes. The dye DAN reacts with nitrite to yield the fluorescent product naphthotriazole. The reaction was then stopped by adding 10 µl of NaOH (2.8 M), and the fluorescence of the samples was read using excitation frequency 375 nm and emission frequency 415 nm.

Figure 22:
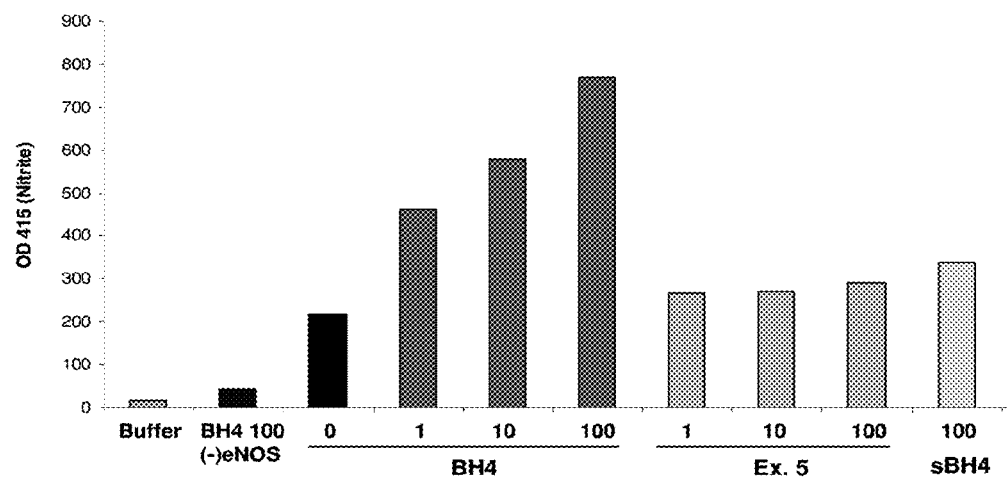
FIG. 22 shows the percentage of nitrate+nitrite increase (as shown by μM concentration) in an in vitro cell-free eNOS potentiation assay after treatment with buffer, control, BH4, Example 5, and 6S-BH4 at various concentrations.

Similar to 6S-BH4 (the less biologically relevant isomer of BH4), which served as a negative control, the compound of Example 5 (val-BH4) did not significantly potentiate eNOS activity in a cell-free purified component assay (see FIG. 22). BH4 did potentiate eNOS activity in a dose-dependent manner. Since Example 5 did potentiate eNOS in cultured endothelial cells, this result indicates that Example 5 is an analog that appears to require cellular processing (e.g., de-esterification) for efficacy, i.e., Example 5 may function as a pro-drug.

Figure 23:
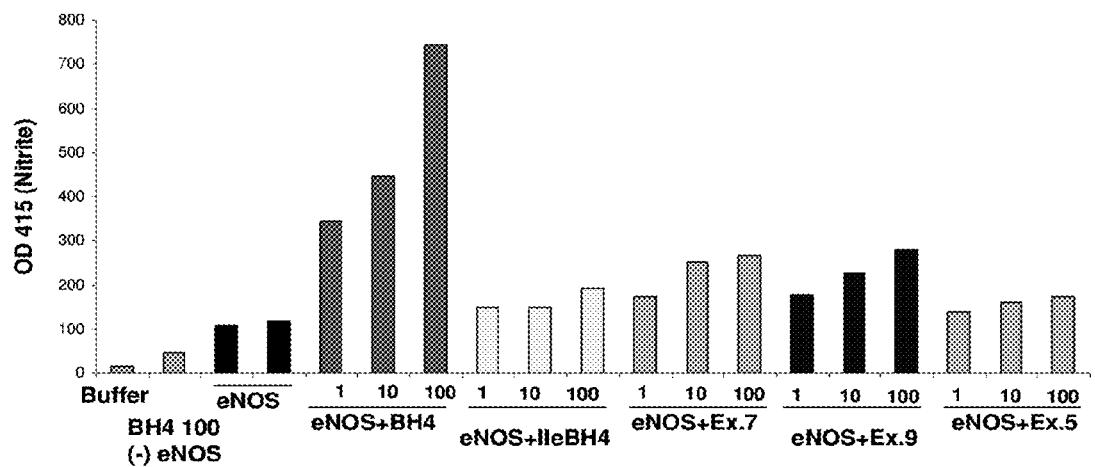
FIG. 23 shows the percentage of nitrate+nitrite increase (as shown by μM concentration) in an in vitro cell-free eNOS production assay after treatment with buffer, control, BH4, Example 5, Example 6, Example 7, and Example 9 at various concentrations.

A second cell-free assay was performed to assess the lysine (example 7), proline (example 9), and isoleucine (example 6) esters of BH4. The results are shown in FIG. 23. The lysine ester and proline ester had a slight effect on eNOS activity, but these responses were not comparable to that of BH4. Two possible explanations are that the presence of impurities such as small amounts of free BH4 in the ester samples could cause a small amount of eNOS potentiation; or that the space filling structure of the lysine ester or proline ester permits a minor degree of interaction between the BH4 portion of the molecule and the eNOS active site.

Anti-Hypertensive Properties of BH4 Analogs

In previous studies, it was determined that doses of 10, 100, and 500 mg/kg/day BH4 reduced the blood pressure of Spontaneously Hypertensive rats (SHR) after two weeks of oral administration. This study was to determine if the BH4 analogs have a similar hypotensive effect and to determine the steady state pharmacokinetics (PK) profiles of plasma BH4 concentrations.

Male Wistar-Kyoto (WKY) rats and SHR rats (Elevage Janvier, France, 7 weeks old) were housed seven days prior to the beginning of experiments with free access to standard chow and water and maintained on an inversed 12 h dark/light cycle (10:00/22:00). After a one week acclimation period, the animals were trained to the tail-cuff system during one week (3 sessions). The following week, two baseline measurements of blood pressure were performed.

The rats (10 weeks old) then received respective treatments of water, vehicle, 2, 10, or 30 mg/kg/day of BH4 analog (Example 5, Val-BH4) or 100 mg/kg/day BH4 by oral gavage (8 mL/kg, dissolved in 100 µM ascorbic acid) performed once a day during 21 days of treatment. The doses of BH4 analog were prepared as mg/kg equivalents of BH4 (calculated using BH4 and BH4 analog 2HCl molecular weights). Body weight was monitored 3 times per week and the most recent body weight was used to adjust drug and vehicle daily intake. Seven experimental groups of rats were evaluated: Group 1—normotensive WKY rats and water gavage; Group 2—hypertensive SHR rats and water gavage; Group 3—hypertensive SHR rats and vehicle gavage; Group 4—hypertensive SHR rats and BH4 100 mg/kg/day gavage; Group 5—hypertensive SHR rats and BH4 analog 2 mg/kg/day gavage; Group 6—hypertensive SHR rats and BH4 analog 10 mg/kg/day gavage; Group 7—hypertensive SHR rats and 30 mg/kg/day BH4 analog gavage. To account for animal loss or animal disqualification during experimental handling, 10 rats were used in each group, with the expectation to obtain interpretable results for at least 8. Systolic blood pressure (SBP) and heart rate (HR) were measured twice weekly during the 3-week treatment period.

Systolic blood pressure (SBP) and heart rate (HR) were measured using the tail-cuff method, twice before the beginning of the treatment and twice weekly during the 3 week treatment period (6 measurements during the treatment period). Rats were placed in a plastic restraint and warmed to 20-30° C. A pneumatic pulse sensor was attached to the tail. After cuff inflation, SBP was measured and HR was determined by counting pulse numbers per minute. Data for each rat was taken an average of at least 4 stable readings. At least 10 cuff inflations were performed for each BP measurement.

Figure 24:
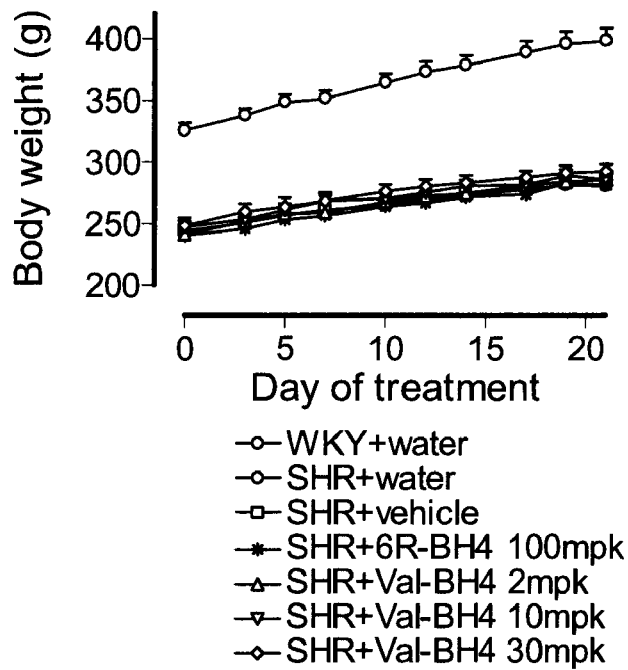
FIG. 24 shows the evolution of body weights during the 3-week treatment period comparing the effect of hypertension with water administration (Wistar-Kyoto rats versus Spontaneously Hypertensive rats (SHR)), vehicle administration in SHR, administration of BH4 and administration of the compound of Example 5 at various concentrations.
Figure 25:
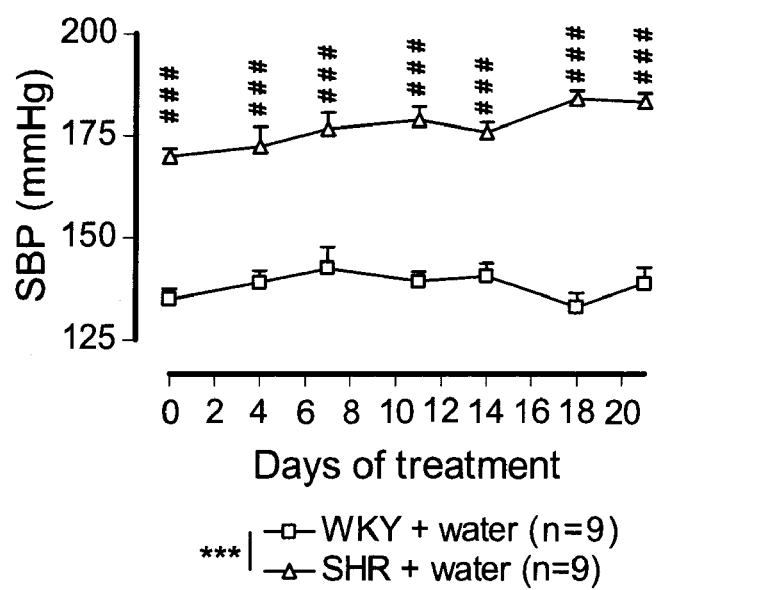
FIG. 25 shows the evolution of systolic blood pressure during the 3-week treatment period with water administration comparing the Wistar-Kyoto rats (WKY) and age-matched Spontaneously Hypertensive rats (SHR).
Figure 26:
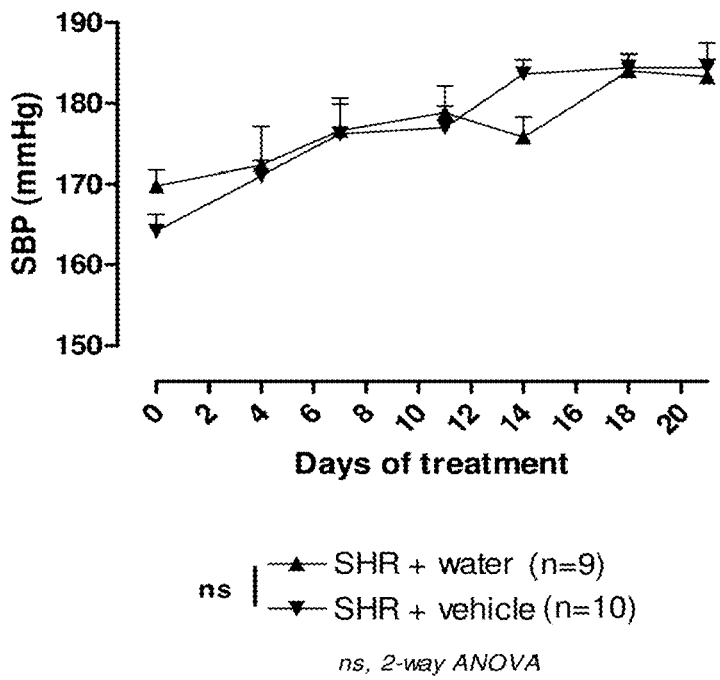
FIG. 26 shows the evolution of systolic blood pressure during the 3-week treatment period in SHR treated with either water or vehicle.
Figure 27:
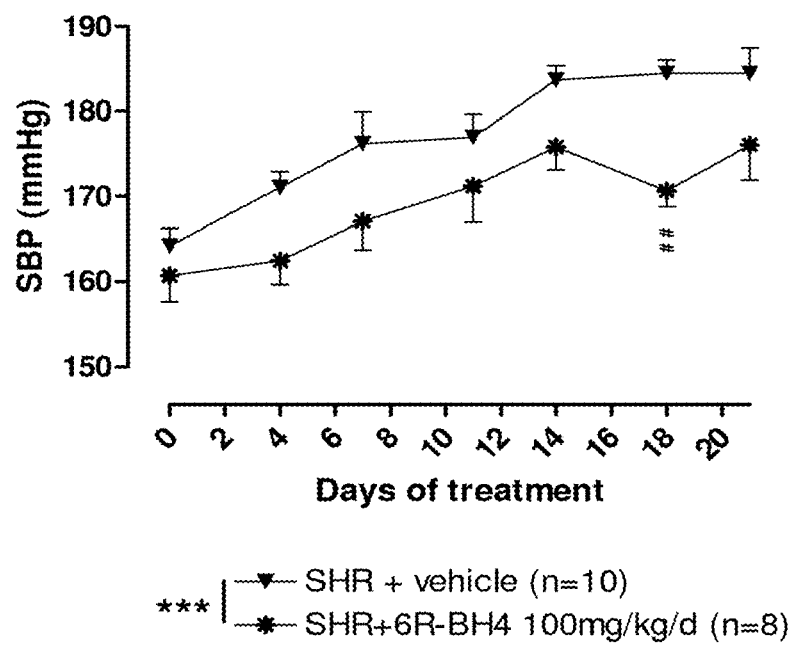
FIG. 27 shows the evolution of systolic blood pressure during the 3-week treatment period in SHR treated with vehicle or BH4 at 100 mg/kg/day.
Figure 28:
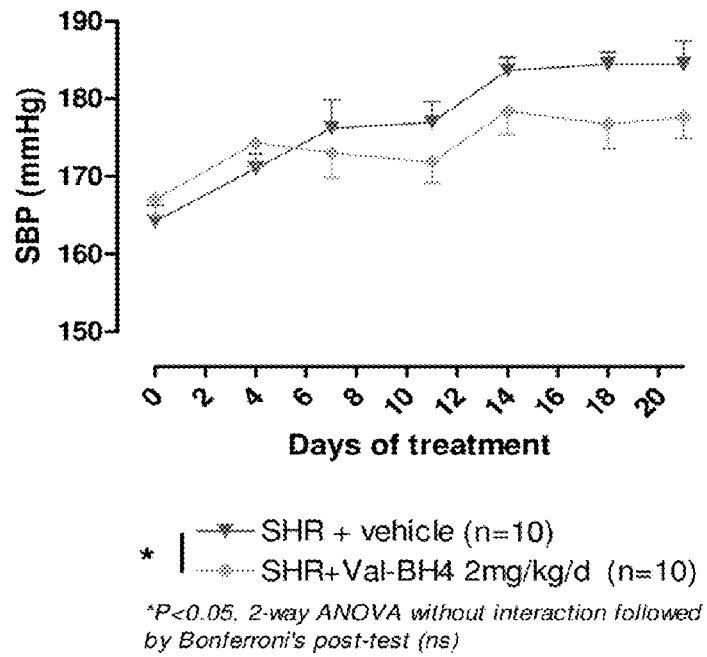
FIG. 28 shows the evolution of systolic blood pressure during the 3-week treatment period in SHR treated with vehicle or the compound of Example 5 at 2 mg/kg/day.
Figure 29:
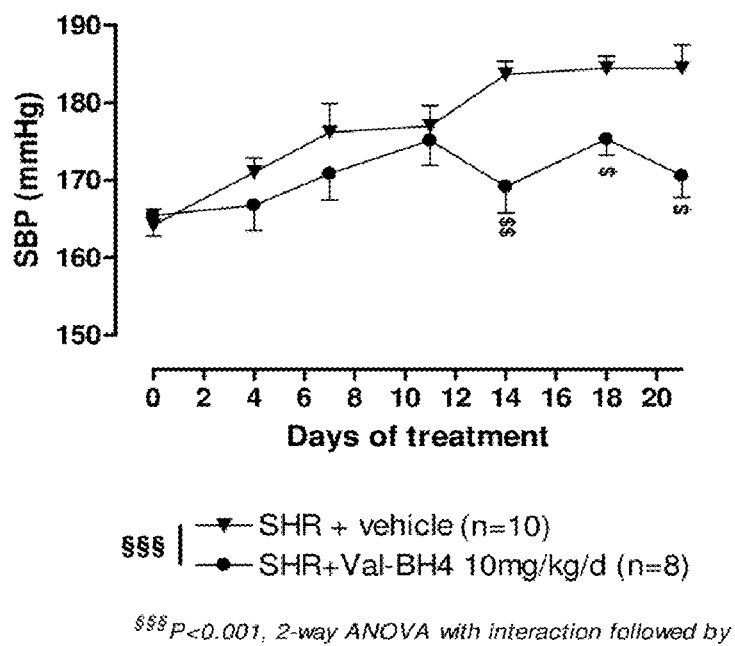
FIG. 29 shows the evolution of systolic blood pressure during the 3-week treatment period in SHR treated with vehicle or the compound of Example 5 at 10 mg/kg/day.
Figure 30:
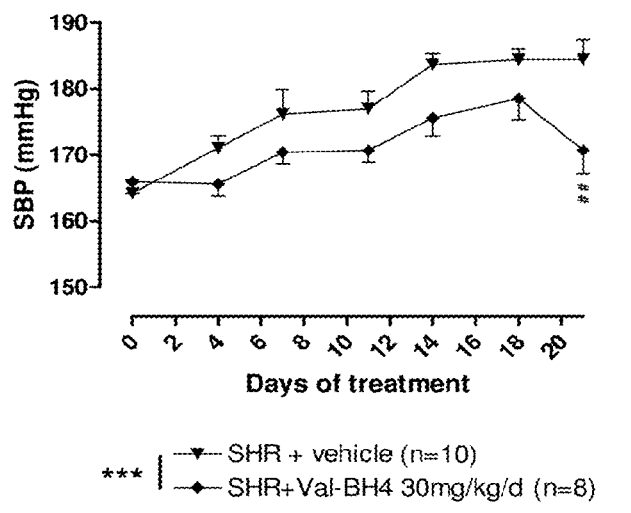
FIG. 30 shows the evolution of systolic blood pressure during the 3-week treatment period in SHR treated with vehicle or the compound of Example 5 at 30 mg/kg/day.
Figure 31:
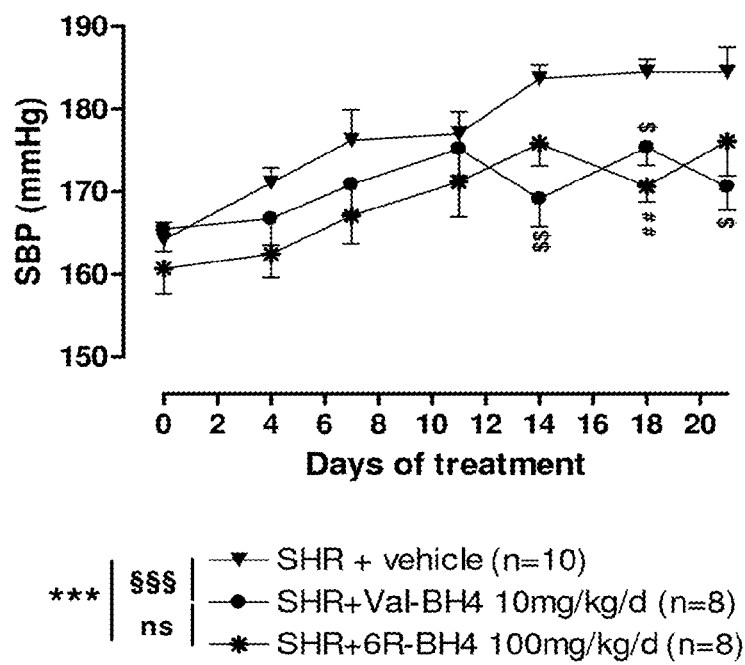
FIG. 31 shows the comparison of the evolution of systolic blood pressure during the 3-week treatment period in SHR treated with vehicle, BH4 (100 mg/kg/day) or the compound of Example 5 at 10 mg/kg/day.

The body weight measurements of each of the groups of rats are shown in FIG. 24. None of the treatments resulted in any modification in body weight. FIG. 25 shows the SBP of the SHR group treated with water versus the control WKY group treated with water. The SBP of the SHR rat was significantly higher than that of the control WKY rat. FIG. 26 shows the SBP of the SHR rat treated with water versus the SHR rat treated with vehicle. The vehicle had no significant effect on SBP of the SHR. FIG. 27 shows the SBP of the SHR rat treated with vehicle versus treatment with 100 mg/kg/day 6R-BH4. The 6R-BH4 treatment resulted in a lowering of the SBP by about 8.4 mmHg after 3 weeks of treatment. FIGS. 28-30 show the effect of treatment with 2, 10, and 30 mg/kg/day of Example 5, respectively on SBP of the SHR. Daily administration of Example 5 (Val-BH4) caused a dose-dependent decrease in SBP of 6.8, 13.9 and 13.7 mmHg following 3 weeks of treatment with 2, 10 and 30 mg/kg/day of Example 5, respectively. FIG. 31 shows a comparison of the effect of daily treatment of 100 mg/kg/day of 6R-BH4 and 10 mg/kg/day of Example 5 (Val-BH4) on SBP of the SHR. Daily administration of 10 mg/kg/day of Example 5 during 3 weeks decreased SBP to the same extent as a 10-fold greater dose of BH4 (100 mg/kg).

A subset of 12 animals (n=3 per group, aged 13.5 to 14.5 weeks) received a final oral dose for PK assessment at steady state after 4 to 5 weeks of treatment in four experimental groups: Group 1—hypertensive SHR rats and BH4 100 mg/kg/day gavage; Group 2—hypertensive SHR rats and BH4 analog 2 mg/kg/day gavage; Group 3—hypertensive SHR rats and BH4 analog 10 mg/kg/day gavage; Group 4—hypertensive SHR rats and 30 mg/kg/day BH4 analog gavage. Before treatment (Day-3 to Day-1), at similar timing to one hour before gavage, a blood sample was drawn for plasma BH4 determination on the 12 animals in which pharmacokinetics were evaluated and on 32 rats not designated for PK assessment. About 250 µl of whole blood was drawn from the tail vein under isoflurane anesthesia at each of the following time points: before treatment, and 0.5, 1, 2, 4, 6, 8, and 12 hours after oral gavage. The blood was collected in potassium EDTA microtubes. The blood was then centrifuged for 5 minutes at 4° C. and 8000 RPM. Two aliquots of 45 µl plasma were transferred to two new cooled microtubes containing 5 µl of 10 mM DTE in PBS and mixed. The samples were then snap-frozen with liquid nitrogen and stored at −80° C. until analyzed.

All publications cited above are, in relevant part, incorporated herein by reference. The citation of any publication is not to be construed as an admission that it constitutes prior art relative to the disclosed invention.

The foregoing description is given for clearness of understanding only, and no unnecessary limitations should be understood therefrom, as modifications within the scope of the invention may be apparent to those having ordinary skill in the art.

What is claimed is:

1. A method of treating a BH4-responsive condition or disorder, comprising administering to a subject a compound having a formula

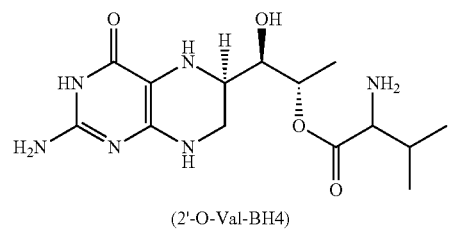

(2'-O-Val-BH4)

or a tautomer or a pharmaceutically acceptable salt thereof, or a pharmaceutical composition comprising 2'-O-Val-BH4 or a tautomer or a pharmaceutically acceptable salt thereof, and a pharmaceutically acceptable excipient, diluent or carrier; wherein the BH4-responsive condition or disorder is autism or hypertension.

2. The method of claim 1, wherein the 2'-O-Val-BH4, or a tautomer or a pharmaceutically acceptable salt thereof, is administered in a daily dose of about 0.1 mg/kg to about 50 mg/kg in terms of BH4-equivalent amount.

3. The method of claim 1, wherein the compound or pharmaceutical composition is administered daily in a single dose, in two doses, or in more than two doses.

4. The method of claim 1, wherein the compound or pharmaceutical composition is administered orally.

5. The method of claim 1, wherein the 2'-O-Val-BH4 has a formula

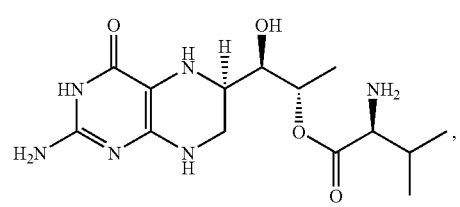

or a tautomer or a pharmaceutically acceptable salt thereof.

6. The method of claim 1, wherein the 2'-O-Val-BH4 is a hydrochloride salt of 2'-O-Val-BH4.

7. The method of claim 1, wherein the hypertension is recalcitrant or uncontrolled hypertension, pulmonary arterial hypertension, idiopathic pulmonary hypertension, or pulmonary hypertension in the newborn (PPHN).

* * * * *